United States Patent
Ootsuki

(10) Patent No.: US 10,581,022 B2
(45) Date of Patent: Mar. 3, 2020

(54) POLYMERIZABLE LIQUID CRYSTAL COMPOUND, COMPOSITION, LIQUID CRYSTAL POLYMERIZATION FILM-KIND THEREOF AND USE THEREOF

(71) Applicants: JNC CORPORATION, Tokyo (JP); JNC PETROCHEMICAL CORPORATION, Tokyo (JP)

(72) Inventor: Daisuke Ootsuki, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 297 days.

(21) Appl. No.: 15/383,861

(22) Filed: Dec. 19, 2016

(65) Prior Publication Data

US 2017/0174992 A1 Jun. 22, 2017

(30) Foreign Application Priority Data

Dec. 21, 2015 (JP) ................. 2015-248226

(51) Int. Cl.
| | | |
|---|---|---|
| *H01L 51/52* | (2006.01) | |
| *C07D 241/42* | (2006.01) | |
| *C07D 241/38* | (2006.01) | |
| *C07D 215/06* | (2006.01) | |
| *C07D 409/04* | (2006.01) | |
| *C07D 409/14* | (2006.01) | |
| *C09K 19/34* | (2006.01) | |
| *G02B 5/30* | (2006.01) | |
| *C09K 19/04* | (2006.01) | |

(52) U.S. Cl.
CPC ........ *H01L 51/5281* (2013.01); *C07D 215/06* (2013.01); *C07D 241/38* (2013.01); *C07D 241/42* (2013.01); *C07D 409/04* (2013.01); *C07D 409/14* (2013.01); *C09K 19/3447* (2013.01); *C09K 19/3452* (2013.01); *C09K 19/3486* (2013.01); *C09K 19/3491* (2013.01); *C09K 19/3497* (2013.01); *G02B 5/3016* (2013.01); *C09K 2019/0448* (2013.01)

(58) Field of Classification Search
CPC . H01L 51/5281; C07D 215/06; C07D 241/38; C07D 241/42; C07D 409/04; C07D 409/14; C09K 19/3447; C09K 19/3452; C09K 19/3486; C09K 19/3491; C09K 19/3497; C09K 2019/0448; G02B 5/3016
See application file for complete search history.

(56) References Cited

U.S. PATENT DOCUMENTS

| | | |
|---|---|---|
| 2006/0182900 A1 | 8/2006 | Kim |
| 2009/0189120 A1 | 7/2009 | Takeuchi |
| 2013/0239110 A1 | 9/2013 | Koseki |

FOREIGN PATENT DOCUMENTS

| | | |
|---|---|---|
| JP | 8321381 A | 12/1996 |
| JP | 2002-372623 A | 12/2002 |
| JP | 2005289980 A | 10/2005 |
| JP | 2009-179563 A | 8/2009 |
| JP | 2010031223 A | 2/2010 |
| JP | 2010-522893 A | 7/2010 |
| JP | 2012060011 A | 3/2012 |
| JP | 1068816 A | 12/2016 |
| WO | 2005-38517 A1 | 4/2005 |
| WO | 2005085222 A1 | 9/2005 |
| WO | 2008-119427 A1 | 10/2008 |

OTHER PUBLICATIONS

M.S. Park, et al., A New Polarizer with Wide Viewing Angle and Low Color Shift Characteristics designed for In-Plane-Switching Liquid Crystal Display (IPS-LCD), IDW '04 pp. 655-658.
M. Nakata, et al., "P-58: Novel IOptical Compensation Films for IPS-LCDs," SID 06 Digest, pp. 420-423.
K.J. Kim, et al., "New Structure of IPS Mode with In-Cell Retarder for TV Application," SID 06 Digest, pp. 1158-1161.

*Primary Examiner* — Robert S Walters, Jr.
(74) *Attorney, Agent, or Firm* — Hogan Lovells US LLP

(57) ABSTRACT

An object is to provide a polymerizable liquid crystal compound, a polymerizable liquid crystal composition containing the compound and liquid crystal polymerization film-kind capable of controlling chromatic dispersion characteristics and having low positive chromatic dispersion characteristics.
An aspect can be exemplified in which the polymerizable liquid crystal compound is represented by formula (1):

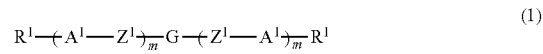

in which, in formula (1), G is a group composed of a quinoline skeleton, an isoquinoline skeleton, a quinoxaline skeleton or a quinazoline skeleton, $A^1$ is 1,4-phenylene or 1,4-cyclohexylene, $Z^1$ is a connecting group, m is an integer from 0 to 3, and $R^1$ is a group containing a polymerizable group.

12 Claims, No Drawings

POLYMERIZABLE LIQUID CRYSTAL COMPOUND, COMPOSITION, LIQUID CRYSTAL POLYMERIZATION FILM-KIND THEREOF AND USE THEREOF

TECHNICAL FIELD

The invention relates to a polymerizable liquid crystal compound having a quinoline skeleton, an isoquinoline skeleton, a quinoxaline skeleton or a quinazoline skeleton, a polymerizable liquid crystal composition containing the compound, and liquid crystal polymerization film-kind obtained by the composition, and use thereof.

A phase difference film having homogeneous alignment can be used, for example, in the form of a ½ wavelength plate, a ¼ wavelength plate, or a composite phase difference plate and a circular polarizing plate in combination with a film having any other optical function (see Patent literature No. 1).

A phase difference film having homeotropic alignment has an optical axis in an $n_z$ direction, in which a refractive index in a direction of the optical axis is larger than a refractive index in a direction perpendicular thereto, and therefore is classified into a positive C-plate in an index ellipsoid. The positive C-plate is combined with the film having any other optical function. Thus, such a combined positive C-plate can be applied to optical compensation of a homogeneously aligned liquid crystal mode or a so-called in-plane switching (IPS) mode, for example, an improvement of viewing angle characteristics of a polarizing plate (Non-patent literature Nos. 1 to 3, Patent literature Nos. 2 and 3).

Optical characteristics required for the phase difference film are different depending on an application or a purpose, and therefore a variety of polymerizable liquid crystal compounds have been developed as a compound to be used. Moreover, control of the anisotropy and the alignment characteristics is difficult by single use in many cases, and therefore the compound is combined with various compounds and utilized in the form of the polymerizable liquid crystal composition.

Such a polymerizable liquid crystal composition is dissolved into an organic solvent for the purpose of adjusting coating properties or the like, and used as ink. In order to produce the film having optical anisotropy by using the polymerizable liquid crystal composition, a polymerizable liquid crystal compound, a photopolymerization initiator, a surfactant and so forth are dissolved into the organic solvent to prepare the ink in which solution viscosity, leveling properties and so forth are adjusted. The ink is coated onto a substrate, and the solvent is removed by drying to align the polymerizable liquid crystal composition on the substrate. On the above occasion, if a substrate subjected alignment treatment is used, a uniform alignment state can be easily obtained. Next, the liquid crystal composition is irradiated by ultraviolet light to allow polymerization and immobilize the alignment state. A process from removing the solvent by drying to polymerization is ordinarily carried out under room temperature, and during the process, a uniform liquid crystal state is required to be kept without causing precipitation of crystal or the like. Therefore, the polymerizable liquid crystal compound is required to have good compatibility with other compounds and high solubility in the organic solvent. The organic solvent with high safety is preferably used in consideration of an environmental impact or an influence on a human body. The polymerizable liquid crystal composition is required to maintain a liquid crystal phase for a long period of time near room temperature after the solvent is removed.

In addition thereto, a polymer obtained from the liquid crystal composition is also required to have, in addition to the characteristics of the optical anisotropy, characteristics such as high transparency, high mechanical strength, high adhesion to the substrate, low shrinkage, high heat resistance and high chemical resistance.

In an optically anisotropic layer formed of rod-like molecules, an extraordinary refractive index and an ordinary refractive index of anisotropic molecules is ordinarily reduced accordingly as a wavelength increases. On the above occasion, the extraordinary refractive index has a larger ratio of a change of the refractive index relative to the wavelength in comparison with the ordinary refractive index. Thus, birefringence is reduced accordingly as the wavelength applied increases. On the other hand, in a display device such as a liquid crystal display (LCD), a light source is white light composed of light having a wavelength of about 380 to 800 nanometers. However, when a ½λ plate, a ¼λ plate or the like is designed and applied by using an ordinary optical anisotropic layer, a deviation of phase difference is produced depending on the chromatic dispersion characteristics described above as the wavelength is away from a center wavelength. A polarization state is changed in association with the deviation of phase difference to cause a problem of coloring of light or the like. In order to prevent occurrence of such problems, control of the chromatic dispersion characteristics is required to be a designed phase difference in each wavelength, and a desire has been expressed for a material having low positive chromatic dispersion characteristics, and also a material in which the birefringence increases accordingly as the wavelength increases.

In an organic electroluminescence display (OLED), use of a circular polarizing plate formed of a ¼ wavelength plate and a polarizer on a viewing side has been recently known for the purpose of preventing outside light reflection (Patent Literature No. 4). Also in such an application, the deviation of phase difference by the chromatic dispersion characteristics causes a change in the polarization state. Accordingly, such a problem occurs as incapability of effectively obtaining an antireflection function relative to a total wavelength in a visible region, and therefore a desire has been expressed for a material having reverse chromatic dispersion characteristics.

As a method of obtaining the optically anisotropic layer having the reverse chromatic dispersion characteristics, a method in which two sheets of phase difference layers are laminated at each angles in each alignment axis direction thereof, is proposed (Patent literature Nos. 5 and 6). However, such a laminate requires two sheets of the phase difference layers, and adjustment of the angle of the anisotropy of two sheets of the phase difference layers, and has had problems such as complexity in production for forming the laminate, an increased film thickness of the optically anisotropic layer or the like.

In order to solve such a problem, a desire has been recently expressed for the optically anisotropic layer having reverse chromatic dispersion without laminating the layers. A proposal has been made on a polymerizable liquid crystal compound having reverse chromatic dispersion characteristics (Patent literature Nos. 7 to 11).

However, in the compound described in Patent literature No. 7, the birefringence is low, and therefore an increase of film thickness is required in order to obtain a desired phase difference, and an aspect ratio is small, and therefore control of alignment uniformity is difficult. Furthermore, a synthesis route is long, and therefore production is difficult. Such problems are concerned. The compounds described in Patent literature Nos. 8 to 11 each are high in a temperature range of the liquid crystal phase and a clearing point, and therefore such an art requires a complicated process of polymerizing the compound by irradiating with ultraviolet light while the compound is heated. Moreover, the compounds described in Patent literature Nos. 7 to 11 are generally low in solubility in an organic solvent and short in a period of time of holding the liquid crystal phase at room temperature, and therefore have difficulty in handling in a process of producing a substrate-embedded liquid crystal polymerization film and in other stages.

CITATION LIST

Patent Literature

Patent literature No. 1: JP 2002-372623 A.
Patent literature No. 2: WO 2005/38517 A.
Patent literature No. 3: US 2006/182900 A.
Patent literature No. 4: JP H8-321381 A.
Patent literature No. 5: JP H10-68816 A.
Patent literature No. 6: JP 2001-4837 A.
Patent literature No. 7: JP 2010-522893 A.
Patent literature No. 8: JP 2009-179563 A.
Patent literature No. 9: WO 2012/060011 A.
Patent literature No. 10: JP 2005-289980 A.
Patent literature No. 11: JP 2010-31223 A.

Non-Patent Literature

Non-patent literature No. 1: M. S. Park et al, IDW '04 FMC8-4.
Non-patent literature No. 2: M. Nakata et al, SID '06 P-58.
Non-patent literature No. 3: K. J. Kim et al, SID '06 Digest.

SUMMARY OF INVENTION

Technical Problem

One of the problems of the invention is to provide a polymerizable liquid crystal compound serving as a raw material of liquid crystal polymerization film-kind having low positive chromatic dispersion characteristics, a liquid crystal composition serving as a raw material of the liquid crystal polymerization film-kind having low positive chromatic dispersion characteristics, the liquid crystal polymerization film-kind having low positive chromatic dispersion characteristics, a phase difference film formed of the liquid crystal polymerization film-kind, a device and a method of producing the device.

Solution to Problem

The present inventors have found that positive chromatic dispersion characteristics of substrate-embedded liquid crystal polymerization film is low, in which the liquid crystal polymerization film are prepared by using as a raw material a polymerizable liquid crystal composition containing a specific polymerizable liquid crystal compound having a quinoline skeleton, an isoquinoline skeleton, a quinoxaline skeleton or a quinazoline skeleton, and have completed the invention.

The invention includes item 1 to item 20 as described below.

Item 1. A polymerizable liquid crystal compound, represented by formula (1):

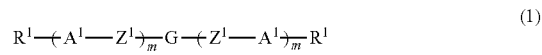

wherein, in formula (1), $A^1$ is independently 1,4-phenylene, 1,4-cyclohexylene, 1-cyclohexene-1,4-ylene, 2-cyclohexene-1,4-ylene, pyridine-2,5-diyl or naphthalene-2,6-diyl, and in the 1,4-phenylene or the naphthalene-2,6-diyl, at least one piece of hydrogen may be replaced by fluorine, chlorine, trifluoromethyl, alkyl having 1 to 5 carbons, alkoxy having 1 to 5 carbons, alkoxycarbonyl having 1 to 5 carbons or alkanoyl having 1 to 5 carbons, $Z^1$ is independently a single bond, —OCH$_2$—, —CH$_2$O—, —COO—, —OCO—, —CF$_2$O—, —OCF$_2$—, —CH$_2$CH$_2$—, —CF$_2$CF$_2$—, —OCH$_2$CH$_2$O—, —CH=CHCOO—, —OCOCH=CH—, —CH$_2$CH$_2$COO—, —OCOCH$_2$CH$_2$—, —CH$_2$CH$_2$OCO—, —COOCH$_2$CH$_2$—, —CH=CH—, —N=CH—, —CH=N—, —N=C(CH$_3$)—, —C(CH$_3$)=N—, —N=N— or —C≡C—, m is each independently an integer from 0 to 3, in which at least one piece of m is not 0, G is a divalent organic group that has a quinoline skeleton, an isoquinoline skeleton, a quinoxaline skeleton or a quinazoline skeleton, and has 10 to 24 π-electrons, and $R^1$ is independently hydrogen, fluorine, chlorine, trifluoromethyl, trifluoromethoxy, cyano, alkyl having 1 to 12 carbons, alkoxy having 1 to 12 carbons, alkenyl having 2 to 12 carbons, alkylester having 1 to 12 carbons or a group represented by formula (2), in which at least one piece of $R^1$ is a group represented by formula (2):

—Y$^1$-Q$^1$-PG     (2)

wherein, in formula (2), $Y^1$ is a single bond, —O—, —COO—, —OCO— or —OCOO—, $Q^1$ is a single bond or alkylene having 1 to 20 carbons, and in the alkylene, at least one piece of —CH$_2$— may be replaced by —O—, —COO—, —OCO—, —CH=CH— or —C≡C—, and PG is a polymerizable group represented by any one of formula (PG-1) to formula (PG-9):

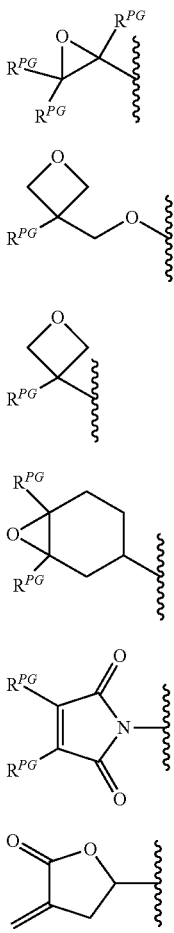

(PG-4)

(PG-5)

(PG-6)

(PG-7)

(PG-8)

(PG-9)

wherein, in formula (PG-1) to formula (PG-9), $R^{PG}$ is independently hydrogen, halogen, methyl, ethyl or trifluoromethyl.

Item 2. The polymerizable liquid crystal compound according to item 1, wherein,

G is (A) a divalent functional group that has a quinoline skeleton, and is connected in 5-position and 8-position of the quinoline skeleton, respectively, (B) a divalent functional group that has an isoquinoline skeleton, and is connected in 5-position and 8-position of the isoquinoline skeleton, respectively, (C) a divalent functional group that has a quinoxaline skeleton, and is connected in 5-position and 8-position of the quinoxaline skeleton, respectively, or (D) a divalent functional group that has a quinazoline skeleton, and is connected in 5-position and 8-position of the quinazoline skeleton, respectively.

Item 3. The polymerizable liquid crystal compound according to item 1, wherein, $A^1$ is independently 1,4-phenylene, 1,4-cyclohexylene, 1-cyclohexene-1,4-ylene or 2-cyclohexene-1,4-ylene, and in the 1,4-phenylene, at least one piece of hydrogen may be replaced by fluorine, chlorine, trifluoromethyl, alkyl having 1 to 5 carbons, alkoxy having 1 to 5 carbons, alkoxycarbonyl having 1 to 5 carbons or alkanoyl having 1 to 5 carbons, and $Z^1$ is independently a single bond, —OCH$_2$—, —CH$_2$O—, —COO—, —OCO—, —CF$_2$O—, —OCF$_2$—, —CH$_2$CH$_2$—, —OCH$_2$CH$_2$O—, —CH$_2$CH$_2$COO—, —OCOCH$_2$CH$_2$—, —CH$_2$CH$_2$OCO— or —COOCH$_2$CH$_2$—.

Item 4. The polymerizable liquid crystal compound according to item 1, wherein both pieces of $R^1$ are a group represented by formula (2).

Item 5. The polymerizable liquid crystal compound according to item 1, wherein G is a group described in formula (G-1), formula (G-2) or formula (G-3):

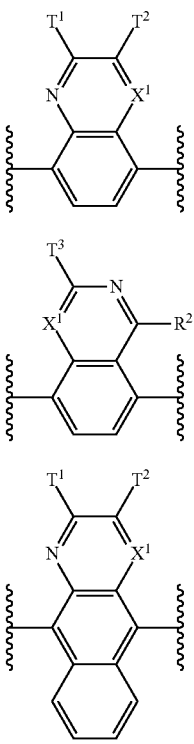

(G-1)

(G-2)

(G-3)

wherein, in formula (G-1) and formula (G-2), and formula (G-3), $X^1$ is —C($R^3$)═ or —N═, in which $R^3$ is independently hydrogen, fluorine, chlorine, trifluoromethyl, trifluoromethoxy, alkyl having 1 to 12 carbons or phenyl, and $T^1$, $T^2$ and $T^3$ are independently hydrogen, fluorine, chlorine, trifluoromethyl, trifluoromethoxy, alkyl having 1 to 12 carbons, alkoxy having 1 to 12 carbons, alkoxycarbonyl having 1 to 12 carbons, alkanoyl having 1 to 12 carbons or an aromatic ring having 6 to 18 π-electrons, and in the alkyl, the alkoxy, the alkoxycarbonyl and the alkanoyl, at least one piece of —CH$_2$— may be replaced by —O—, —CO— or —S—, and $T^1$ and $T^2$ may be bonded to each other to form a ring, and $R^2$ is independently hydrogen, fluorine, chlorine, trifluoromethyl, trifluoromethoxy, alkyl having 1 to 12 carbons or phenyl.

Item 6. The polymerizable liquid crystal compound according to item 5, wherein, in formula (G-1) or formula (G-2), at least either $T^1$ or $T^2$, and $T^3$ are an aromatic ring described in any one of formula (T-1) to formula (T-9):

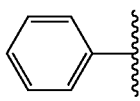

(T-1)

-continued

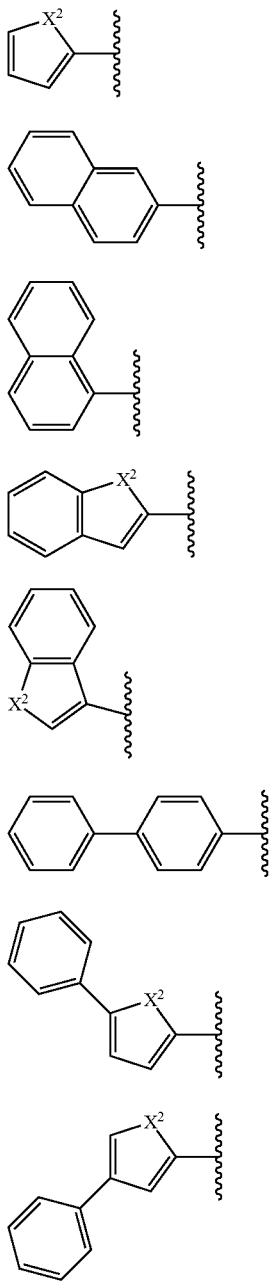

(T-2)
(T-3)
(T-4)
(T-5)
(T-6)
(T-7)
(T-8)
(T-9)

wherein, in formula (T-1) to formula (T-9), $X^2$ is —O—, —S— or —NR$^4$—, in which $R^4$ is hydrogen, alkyl having 1 to 5 carbons, alkanoyl having 1 to 5 carbons or phenyl, and at least one piece of —CH= may be replaced by —N=, and at least one piece of hydrogen may be replaced by fluorine, chlorine, cyano, trifluoromethyl, trifluoroacetyl, alkyl having 1 to 5 carbons, alkoxy having 1 to 5 carbons, alkylester having 1 to 5 carbons or alkanoyl having 1 to 5 carbons.

Item 7. The polymerizable liquid crystal compound according to item 5, wherein, in formula (G-1), $T^1$ and $T^2$ are bonded to each other to form a ring, and a structure of the ring is a condensed ring formed of a 5-membered ring, a six-membered ring or a combination of 5-membered ring and six-membered ring.

Item 8. The polymerizable liquid crystal compound according to item 1, wherein PG is a polymerizable group represented by formula (PG-1), and $R^{PG}$ is hydrogen or methyl.

Item 9. The polymerizable liquid crystal compound according to item 1, wherein at least one piece of $A^1$ is 1,4-cyclohexylene.

Item 10. The polymerizable liquid crystal compound according to item 1, wherein at least one piece of $Z^1$ is —CH$_2$CH$_2$COO— or —OCOCH$_2$CH$_2$—, and m is 2.

Item 11. A polymerizable liquid crystal composition, containing at least one polymerizable liquid crystal compound according to item 1.

Item 12. The polymerizable liquid crystal composition according to item 11, wherein a total of content of the polymerizable liquid crystal compound according to any one of item 1 to item 9 is 4 to 50% by weight.

Item 13. Liquid crystal polymerization film-kind, produced by polymerizing the polymerizable liquid crystal composition according to item 11 or 12.

Item 14. The liquid crystal polymerization film-kind according to item 13, wherein a uniform alignment state of liquid crystal molecules is immobilized.

Item 15. The liquid crystal polymerization film-kind according to item 13, satisfying, in the liquid crystal polymerization film, conditions of an expression: $\Delta n(450)/\Delta n(550) \leq 1.05$ and an expression: $\Delta n(650)/\Delta n(550) \geq 0.97$.

Item 16. A polarizing plate, having the liquid crystal polymerization film-kind according to item 13.

Item 17. A display device, having the liquid crystal polymerization film-kind according to item 13.

Item 18. A display device, having the polarizing plate according to item 16.

Item 19. A method of producing a substrate-embedded liquid crystal polymerization film, including a step of coating the polymerizable liquid crystal composition according to item 11 onto the substrate, and polymerizing the polymerizable liquid crystal composition.

Item 20. A method of producing a substrate-embedded liquid crystal polymerization film, including a step of coating the polymerizable liquid crystal composition according to item 11 onto the substrate, and irradiating the liquid crystal composition with light after heat treatment to cure the liquid crystal composition.

Advantageous Effects of Invention

According to the invention, effects described below can be realized.

(A) Realization of an intended hue in an optical device such as a liquid crystal display, in which a change of a polarization state is suppressed in response to a wavelength of light emitted from a light source of the optical device, (B) an effective antireflection function to light having a total in a visible region in an optical device such as an organic electroluminescence display, (C) facilitation of handling of a substrate-embedded liquid crystal polymerization film in a production process and other stages, caused by high compatibility, with an organic solvent, of a raw material of the liquid crystal polymerization film, the raw material capable of being provided for (A) and (B) described above, or (D) facilitation of handling of the substrate-embedded liquid crystal polymerization film in the production process and other stages, caused by a long period of time of holding a liquid crystal phase, under room temperature, of the raw material of the liquid crystal polymerization film, the raw material capable of being provided for (A) and (B) described above.

DESCRIPTION OF EMBODIMENTS

In the invention, "chromatic dispersion characteristics" is a distribution of birefringence in a substrate-embedded liquid crystal polymerization film for each wavelength in a visible light region.

In the invention, "positive chromatic dispersion characteristics" means magnitude of an increase of retardation in a substrate-embedded liquid crystal polymerization film, accompanied by an increase of the wavelength in the visible light region.

In the invention, "low positive chromatic dispersion characteristics" is lowness of an increase of retardation of the substrate-embedded liquid crystal polymerization film, accompanied by the increase of the wavelength in the visible light region, or a decrease of substrate-embedded liquid crystal polymerization film accompanied by the increase of the wavelength in the visible light region.

In the invention, "$\Delta n$" represents the birefringence of the substrate-embedded liquid crystal polymerization film.

In the invention, "$\Delta n(550)$" represents $\Delta n$ at a wavelength of 550 nanometers.

In the invention, "Re" is retardation, or a phase lag of extraordinary light relative to ordinary light. Re is represented by an equation: $Re = \Delta n \times d$, wherein d is a thickness of the liquid crystal polymerization film.

In the invention, "$Re_{450}$" means retardation when light having a wavelength of 450 nanometers is entered perpendicularly to a film surface.

In the invention, "$Re_{550}$" means retardation when light having a wavelength of 550 nanometers is entered perpendicularly to the film surface.

In the invention, "$Re_{650}$" means retardation when light having a wavelength of 650 nanometers is entered perpendicularly to the film surface.

In the invention, "aromatic ring" is a moiety having a ring structure including a condensed ring or ring assemblies, wherein the moiety has a more stable state in terms of energy by delocalization of a valence electron in comparison with one by localization of the valence electron. The moiety includes an atom of oxygen, nitrogen or sulfur.

In the invention, "number of $2\pi$-electrons" in an organic compound is number calculated by a formula: {number of double bonds in structural formula in terms of bond of organic compound}×2, in the structural formula by the bond of the organic compound which is shown by regarding that the valence electron of the organic compound is localized.

In the invention, "Compound (X)" means a compound represented by formula (X). X in "compound (X)" herein is a text, a number, a symbol or the like.

In the invention, "liquid crystal compound" is a generic term of (A) a compound having a liquid crystal phase as a pure substance, and of (B) a compound serving as a component of a liquid crystal composition.

In the invention, "polymerizable group" means a functional group that provides a compound having an capability of causing polymerization by light, heat, a catalyst or other means into a compound having a larger molecular weight.

In the invention, "polymerizable compound" means a compound having a capability of being polymerized by light, heat, the catalyst or other means into the compound having the larger molecular weight.

In the invention, "polymerizable liquid crystal compound" is a compound being liquid crystal compound and polymerizable compound.

In the invention, "monofunctional compound" means a compound having one functional group having a capability of changing the compound into a polymer having a larger molecular weight, by light, heat, the catalyst and other means.

In the invention, "polyfunctional compound" means a compound having a plurality of functional groups having a capability of changing the compound into the polymer having larger molecular weight, by light, heat, the catalyst and other means.

In the invention, "X-functional compound" means a compound having X pieces of functional groups having a capability of changing the compound into the polymer having the larger molecular weight, by light, heat, the catalyst and other means. X in "X-functional compound" herein is an integer.

In the invention, "polymerizable liquid crystal composition" is a composition containing the polymerizable compound and the liquid crystal compound, and a composition containing "polymerizable liquid crystal compound."

In the invention, "substrate-embedded liquid crystal polymerization film" is a matter comprising: a substrate and a product obtained by polymerizing the polymerizable liquid crystal composition on the substrate.

In the invention, "liquid crystal polymerization film" is a part of a product obtained by polymerizing the polymerizable liquid crystal composition on a substrate, excluding the substrate.

In the invention, "liquid crystal polymerization film-kind" is a generic term of "substrate-embedded liquid crystal polymerization film" and "liquid crystal polymerization film."

In the invention, "phase difference film" is a polarization conversion device having optical anisotropy, and being a material mainly utilized for an optical device.

In the invention, "film surface" is a surface between air and the polymerizable liquid crystal composition on which the polymerizable liquid crystal composition is coated.

In the invention, "tilt angle" is an angle between a direction of alignment of liquid crystal molecules and a surface of the substrate.

In the invention, "homogeneous alignment" is alignment with the tilt angle from 0 degrees to 5 degrees.

In the invention, "homeotropic alignment" is alignment with the tilt angle of 85 degrees to 90 degrees.

In the invention, "tilt alignment" means a state in which a direction of a major axis of the liquid crystal molecules rises up vertically from parallel relative to the substrate accordingly as the liquid crystal molecules are separated from the substrate.

In the invention, "twist alignment" means a state in which a direction of alignment of the liquid crystal molecules the direction of the major axis thereof is parallel to the substrate, and a state in which the liquid crystal molecules are twisted stepwise with a perpendicular line on a substrate surface as an axis with departing from the substrate.

In the invention, "immobilization" means that alignment of the liquid crystal compound is immobilized by polymerization.

In the invention, "room temperature" is from 15 to 35° C.

In the invention, "NI point" is a transition temperature from a nematic phase to an isotropic liquid.

In a chemical formula, when the bond between carbon atoms that constitutes a ring, and the bond that represents the functional group are crossed, in a case where the number of the functional group is 0, substitution by the functional group is absent.

Moreover, when the functional group described below is described in the chemical formula, a wavy line means a position of bonding with the functional group. C described below herein represents an arbitrary atom or functional group.

Compound (1)

The polymerizable liquid crystal composition of the invention contains a compound represented by formula (1) as described below.

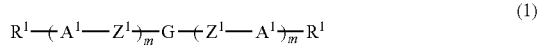

(1)

$A^1$ in Compound (1)

In formula (1), $A^1$ is independently 1,4-phenylene, 1,4-cyclohexylene, 1-cyclohexene-1,4-ylene, 2-cyclohexene-1,4-ylene, pyridine-2,5-diyl or naphthalene-2,6-diyl.

In 1,4-phenylene and naphthalene-2,6-diyl in compound (1), at least one of hydrogen may be replaced by fluorine, chlorine, trifluoromethyl, alkyl having 1 to 5 carbons, alkoxy having 1 to 5 carbons, alkoxycarbonyl having 1 to 5 carbons or alkanoyl having 1 to 5 carbons.

In a viewpoint of prevention of phase separation when compound (1) is mixed with the liquid crystal compound or of an organic solvent, induction of the liquid crystal phase by the polymerizable liquid crystal composition, and reduction of synthesis cost; as $A^1$ in the compound (1), 1,4-phenylene, 1,4-cyclohexylene, 1-cyclohexene-1,4-ylene or 2-cyclohexene-1,4-ylene is preferred.

In a viewpoint of lowness of positive chromatic dispersion characteristics of the liquid crystal polymerization film-kind, as $A^1$ in compound (1) serving as a raw material of the liquid crystal polymerization film-kind, 1,4-cyclohexylene is preferred.

In a viewpoint of magnitude of birefringence of the liquid crystal polymerization film-kind, as $A^1$ in compound (1) serving as the raw material of the liquid crystal polymerization film-kind, a 1,4-phenylene skeleton is further preferred.

In a viewpoint of induction of the liquid crystal phase by the polymerizable liquid crystal composition, when $A^1$ in compound (1) has the 1,4-phenylene skeleton, no more substituted thereto is preferred.

$Z^1$ in Compound (1)

In formula (1), $Z^1$ is independently a single bond, —OCH$_2$—, —CH$_2$O—, —COO—, —OCO—, —CF$_2$O—, —OCF$_2$—, —CH$_2$CH$_2$—, —CF$_2$CF$_2$—, —OCH$_2$CH$_2$O—, —CH=CHCOO—, —OCOCH=CH—, —CH$_2$CH$_2$COO—, —OCOCH$_2$CH$_2$—, —CH$_2$CH$_2$OCO—, —COOCH$_2$CH$_2$—, —CH=CH—, —N=CH—, —CH=N—, —N=C(CH$_3$)—, —C(CH$_3$)=N—, —N=N— or —C≡C—.

For inducing the liquid crystal phase of compound (1), and for reducing production cost of compound (1), as $Z^1$, a single bond, —OCH$_2$—, —CH$_2$O—, —COO—, —OCO—, —CF$_2$O—, —OCF$_2$—, —CH$_2$CH$_2$—, —OCH$_2$CH$_2$O—, —CH$_2$CH$_2$COO—, —OCOCH$_2$CH$_2$—, —CH$_2$CH$_2$OCO— or —COOCH$_2$CH$_2$— is preferred.

In order to prevent phase separation when compound (1) is mixed with the liquid crystal compound or the organic solvent, as at least one of $Z^1$, —CH$_2$CH$_2$COO— or —OCOCH$_2$CH$_2$— is preferred.

In order to decrease a clearing point of the polymerizable liquid crystal composition containing compound (1), as at least one of $Z^1$, —CH$_2$CH$_2$COO— or —OCOCH$_2$CH$_2$— is preferred.

In order to suppress recrystallization in the composition containing compound (1), as at least one of Z, —CH$_2$CH$_2$COO— or —OCOCH$_2$CH$_2$— is preferred.

G in Compound (1)

G is a divalent organic group that has a quinoline skeleton, an isoquinoline skeleton, a quinoxaline skeleton or a quinazoline skeleton, and has 10 to 24 π-electrons.

In a viewpoint of low positive chromatic dispersion characteristics of the liquid crystal polymerization film-kind, G in compound (1) serving as the raw material of the liquid crystal polymerization film-kind is preferably a group described in formula (G-1) to formula (G-3).

For the purpose of induction of the liquid crystal phase by the polymerizable liquid crystal composition, as G in compound (1) serving as the raw material of liquid crystal polymerization film-kind, formula (G-1) to formula (G-3) are preferred.

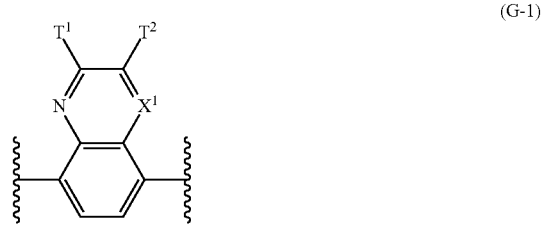

(G-1)

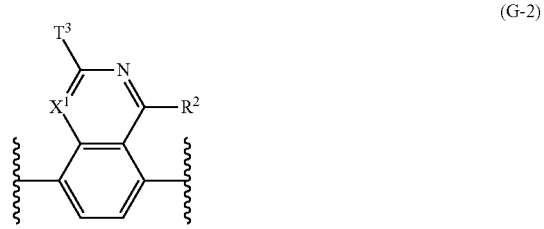

(G-2)

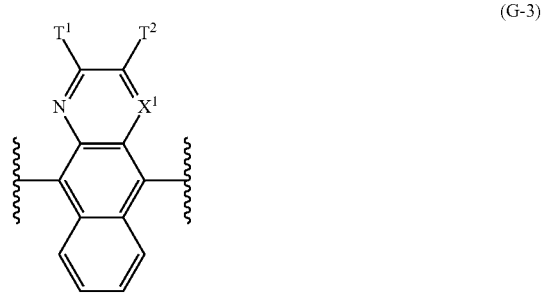

(G-3)

In formula (G-1) to formula (G-3), $X^1$ is —C($R^3$)= or —N=, in which $R^3$ is independently hydrogen, fluorine, chlorine, trifluoromethyl, trifluoromethoxy, alkyl having 1 to 12 carbons or phenyl, $T^1$, $T^2$ and $T^3$ are independently hydrogen, fluorine, chlorine, trifluoromethyl, trifluoromethoxy, alkyl having 1 to 12 carbons, alkoxy having 1 to 12 carbons, alkoxycarbonyl having 1 to 12 carbons, alkanoyl having 1 to 12 carbons or an aromatic ring having 6 to 18 π-electrons, and in the alkyl, the alkoxy, the alkoxycarbonyl and the alkanoyl, at least one piece of —CH$_2$— may be replaced by —O—, —CO— or —S—, and an arbitrary atom in T$^1$ and an arbitrary atom in T$^2$ may form a chemical bond into a ring, and R$^2$ is independently hydrogen, fluorine, chlorine, trifluoromethyl, trifluoromethoxy, alkyl having 1 to 12 carbons or phenyl.

For the purpose of inducing the liquid crystal phase of the polymerizable liquid crystal composition containing compound (1), and of preventing phase separation upon mixing the liquid crystal compound or the organic solvent and achieving low positive chromatic dispersion characteristics of the liquid crystal polymerization film-kind when compound (1) is applied as the raw material, compound (1) in which at least one of T$^1$ and T$^2$, and T$^3$ in formula (G-1) and formula (G-2) are any one of the aromatic rings described in formula (T-1) to formula (T-9) is preferred.

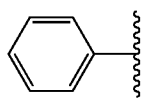
(T-1)

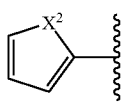
(T-2)

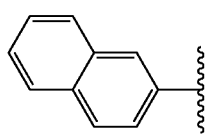
(T-3)

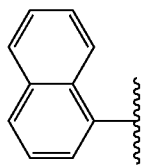
(T-4)

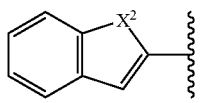
(T-5)

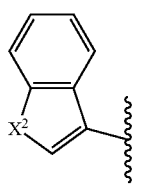
(T-6)

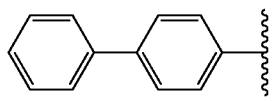
(T-7)

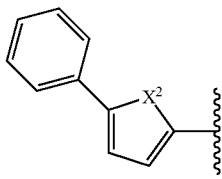
(T-8)

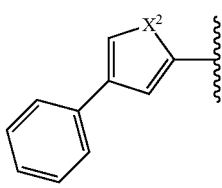
(T-9)

In formula (T-1) to formula (T-9), X$^2$ is —O—, —S— or —NR$^4$—, in which R$^4$ is hydrogen, alkyl having 1 to 5 carbons, alkanoyl having 1 to 5 carbons or phenyl, and at least one of —CH= may be replaced by —N=, and at least one of hydrogen may be replaced by fluorine, chlorine, cyano, trifluoromethyl, trifluoroacetyl, alkyl having 1 to 5 carbons, alkoxy having 1 to 5 carbons, alkylester having 1 to 5 carbons or alkanoyl having 1 to 5 carbons.

R$^1$ in Compound (1)

At least one of R$^1$ in compound (1) is a group represented by formula (2). Another R$^1$ in compound (1) is hydrogen, fluorine, chlorine, trifluoromethyl, trifluoromethoxy, cyano, alkyl having 1 to 12 carbons, alkoxy having 1 to 12 carbons, alkenyl having 2 to 12 carbons, alkylester having 1 to 12 carbons or a group represented by formula (2).

$$—Y^1-Q^1-PG \qquad (2)$$

In formula (2),

Y$^1$ is a single bond, —O—, —COO—, —OCO— or —OCOO—,

Q$^1$ is a single bond or alkylene having 1 to 20 carbons, and in the alkylene, at least one piece of —CH$_2$— may be replaced by —O—, —COO—, —OCO—, —CH=CH— or —C≡C—, and PG is a functional group represented by any one of formula (PG-1) to formula (PG-9).

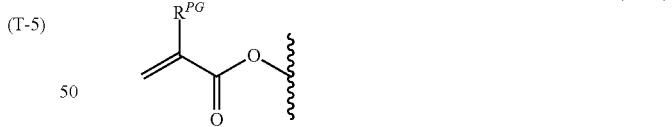
(PG-1)

(PG-2)

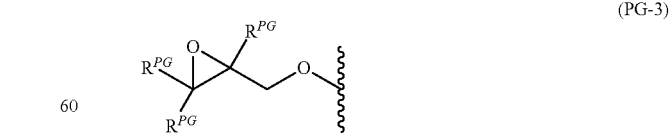
(PG-3)

(PG-4)

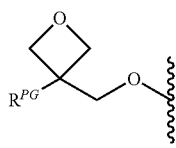 (PG-5)

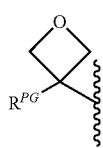 (PG-6)

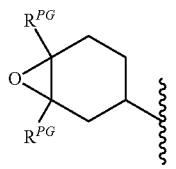 (PG-7)

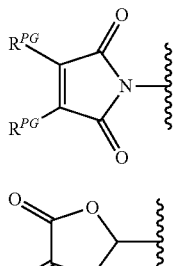 (PG-8)

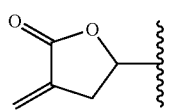 (PG-9)

PG is independently a functional group represented by any one of formula (PG-1) to formula (PG-9).

Each of the functional groups represented by formula (PG-1), formula (PG-8) and formula (PG-9) has an electron withdrawing group adjacent to alkene, and therefore is a polymerizable functional group that is polymerized by various means to change the compound into a polymer having a larger molecular weight.

The functional group represented by formula (PG-2) has an electron donating group adjacent to alkene, and therefore is a polymerizable functional group that is polymerized by various means to change the compound into a polymer having a larger molecular weight.

Each of the functional groups represented by formula (PG-3) to formula (PG-7) has an strained oxa ring, and therefore is a polymerizable functional group that is polymerized by various means to change the compound into a polymer having a larger molecular weight.

Therefore, the functional groups represented by formula (PG-1) to formula (PG-9) are polymerizable groups. Compound (1) has at least one polymerizable group, and therefore is the polymerizable compound.

As the polymerizable group represented by formula (PG-1) to formula (PG-9) in compound (1), an optimum polymerizable group is selected according to conditions of producing a film.

When the liquid crystal polymerization film-kind by applying compound (1) as the raw material are prepared by photo-curing, in viewpoints of adjustment of rate of polymerization, prevention of phase separation upon mixing the compound with the liquid crystal compound or the organic solvent, and reduction of synthesis cost, compound (1) having the polymerizable group represented by formula (PG-1) is preferred.

With Regard to m in Compound (1)

In formula (1), m is independently an integer from 0 to 3. Where, at least one piece of m is not 0.

In a viewpoint of high liquid crystallinity, as m in compound (1) is independently preferably an integer from 0 to 3.

In view of difficulty in causing phase separation upon mixing compound (1) with the liquid crystal compound or the organic solvent, an integer from 0 to 3 of m in compound (1) is independently preferred.

For inducing the liquid crystal phase of the polymerizable liquid crystal composition containing compound (1), m in compound (1) is preferably 2. For preventing phase separation upon mixing the compound with the liquid crystal compound or the organic solvent, m in compound (1) is preferably 2.

Liquid Crystal Compound

A compound inducing the liquid crystal phase ordinarily has a rod-like or disc-like shape. The liquid crystal compound has (A): a plurality of aromatic rings and/or alicyclic rings, and (B): alkylene or any other flexible group connecting the rings, in many cases.

Chromatic Dispersion Characteristics

The chromatic dispersion characteristics of the refractive index are related to an absorption spectrum of a substance as represented by the Lorentz-Lorenz formula. In a neighbor region of a light absorption maximum wavelength of the substance, the refractive index rapidly increases accompanied by closing the light absorption maximum wavelength from the longer wavelength.

In compound (1), a rigid heterocyclic ring having a number of conjugated double bonds is located on the minor axis. The quinoline ring, the isoquinoline ring, the quinoxaline ring, the quinazoline ring or the like are the heterocyclic ring. Because the heterocyclic rings have a sufficient number of conjugated double bonds, light having a longer wavelength, vibrating in minor axis, is able to be absorbed. Therefore, the heterocyclic rings can increase a ratio of a refractive index accomplished with wavelength of the ordinary light.

Compound (1) has a functional group having no conjugated double bond or a small number of conjugated double bonds in the direction of the major axis. A cyclohexane ring, a cyclohexene ring or the like are the functional group. Because the functional group has an insufficient number of conjugated double bonds, light having a short wavelength, vibrating in the major axis, is able to be absorbed. Accordingly, a ratio of refractive index can decreased accomplished with wavelength of extraordinary light.

In an effect on the functional group and on the heterocyclic ring, the polymerizable liquid crystal compound represented by formula (1) has low positive chromatic dispersion characteristics.

Even when compound (1) contains a large amount of polymerizable liquid crystal compound, the crystal is hard to precipitate. In the polymerizable liquid crystal composition containing compound (1), the crystal is hard to precipitate after the solvent is removed. Because a crystal in a polymerizable liquid crystal composition containing compound (1) is hard to precipitate after the solvent is removed, the liquid crystal polymerization film-kind having "no" alignment defect is prepared, easily.

Therefore, if compound (1) is used as the raw material, a phase difference film having a small value of $Re_{450}/Re_{550}$ and a large value of $Re_{650}/Re_{550}$ can be produced. More specifically, the liquid crystal polymerization film-kind having low positive chromatic dispersion characteristics can be produced.

Examples of compound (1) are shown below.
(1-1-1)
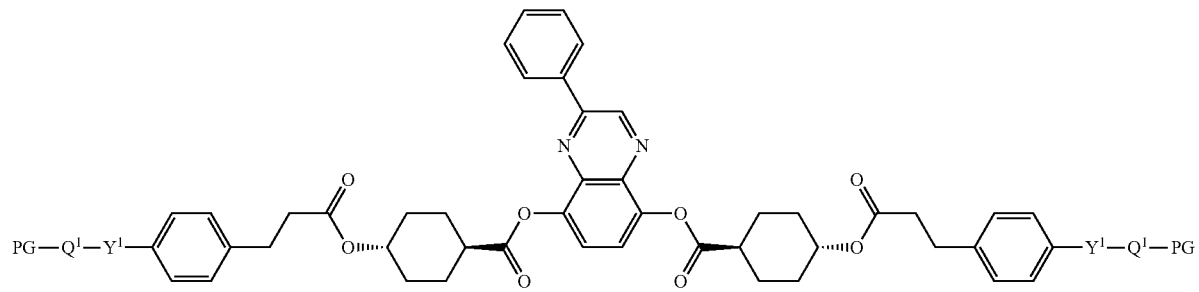
(1-1-2)
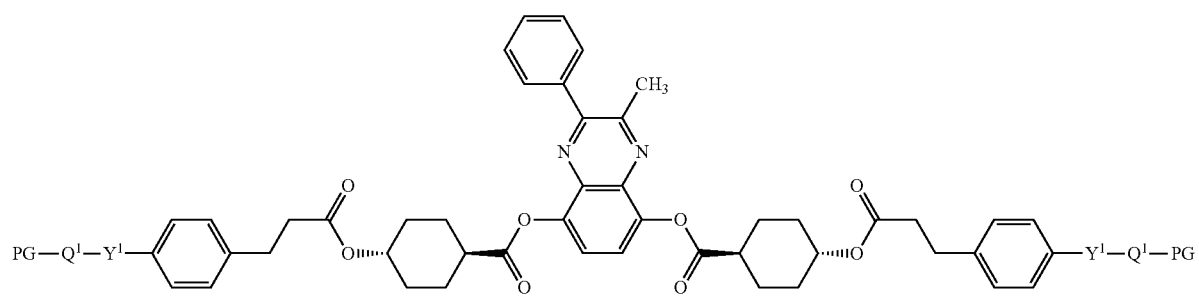
(1-1-3)
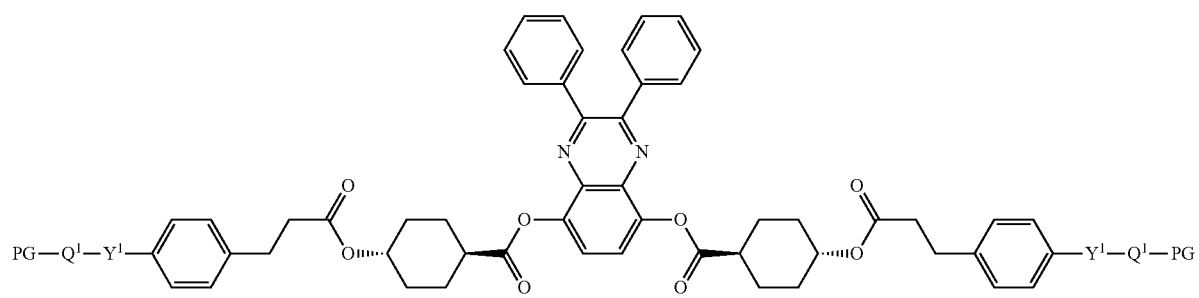
(1-1-4)
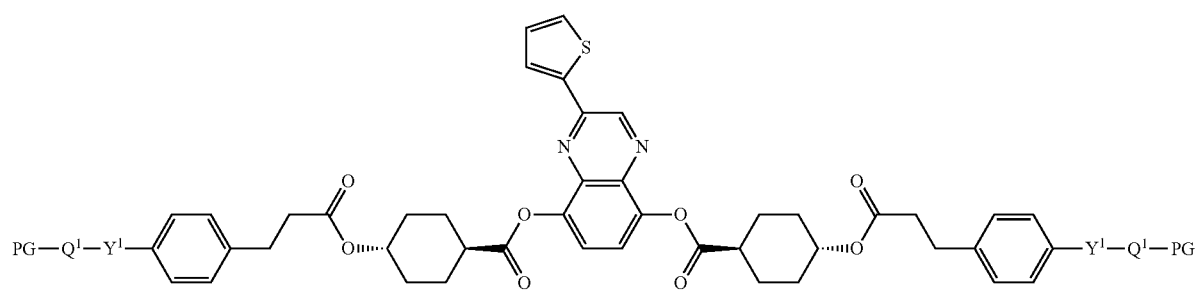
(1-1-5)
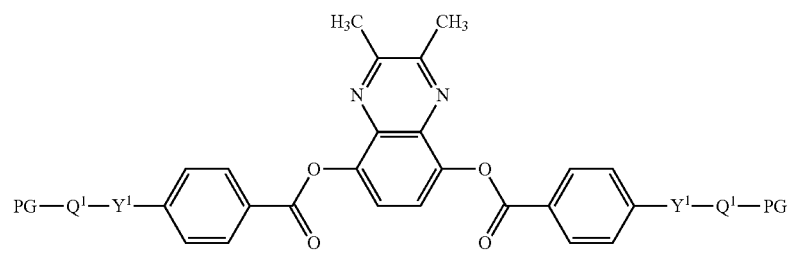

-continued
(1-1-6)
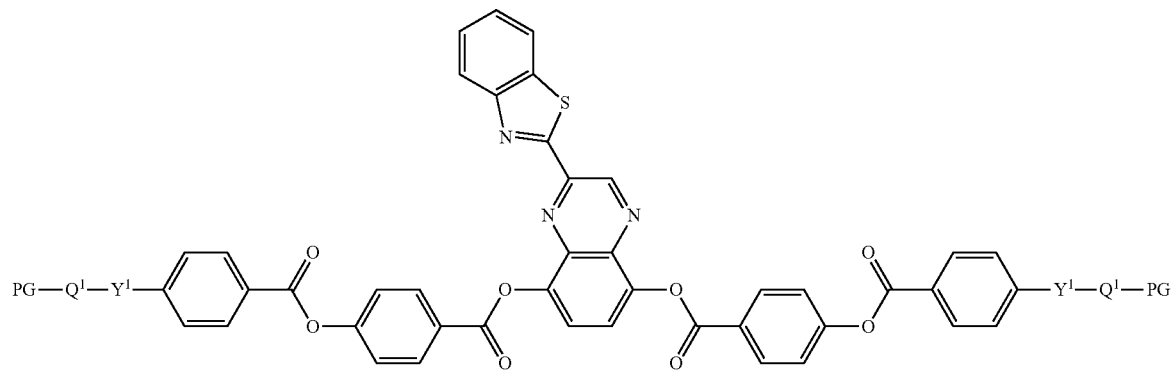
(1-1-7)
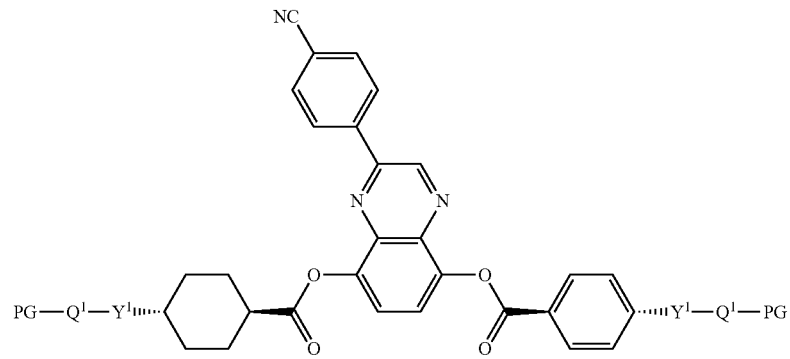
(1-1-8)
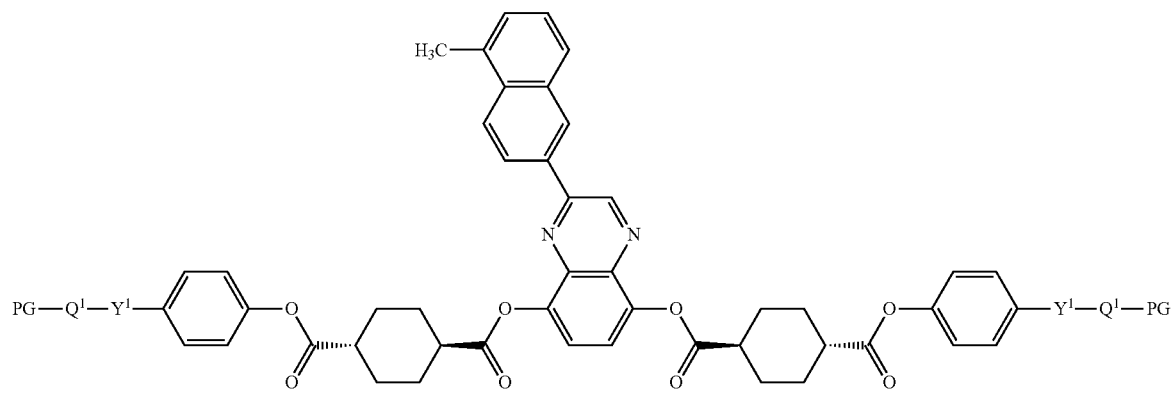
(1-1-9)
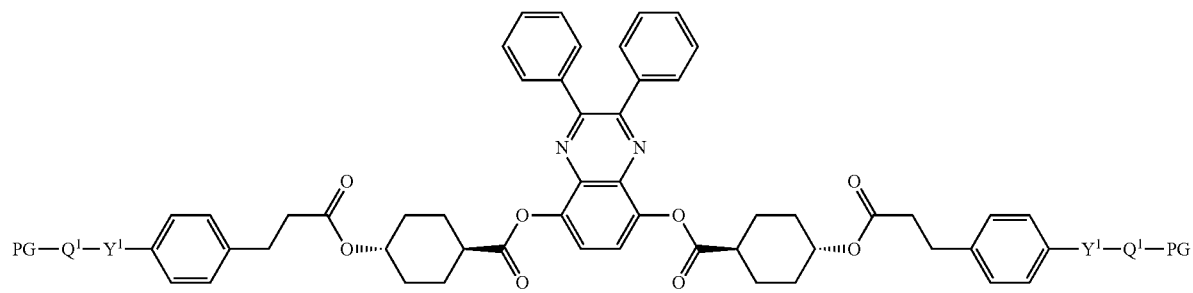

-continued
(1-1-10)
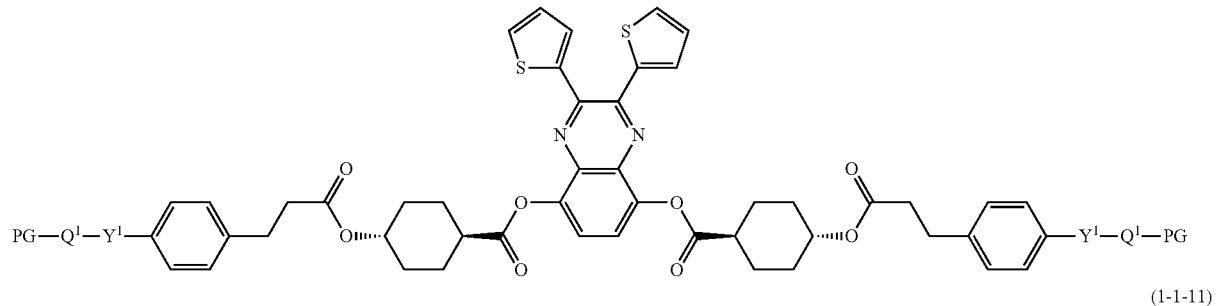
(1-1-11)
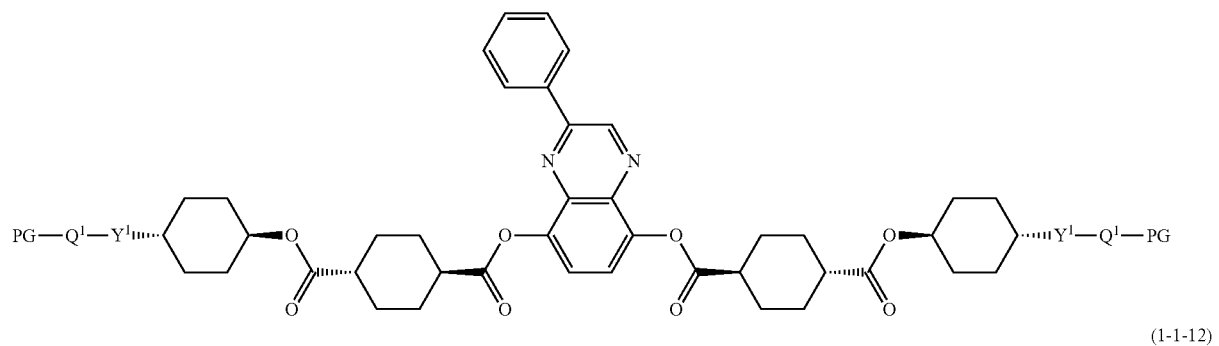
(1-1-12)
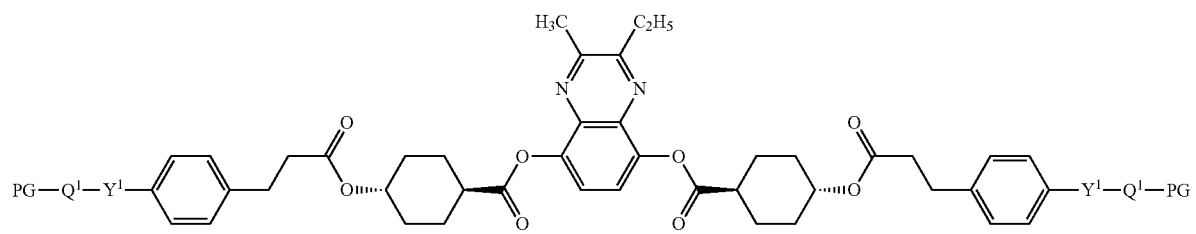
(1-2-1)
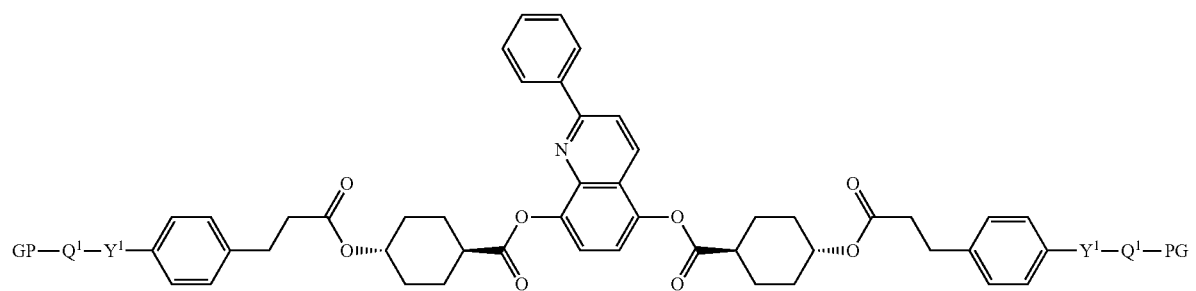
(1-2-2)
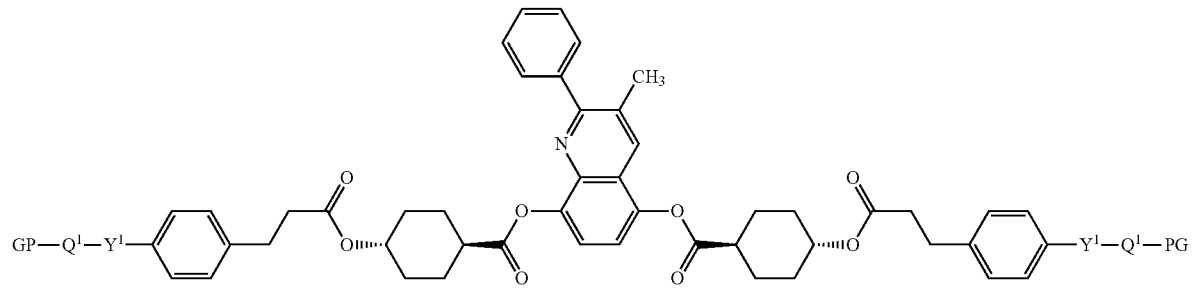

(1-2-3)
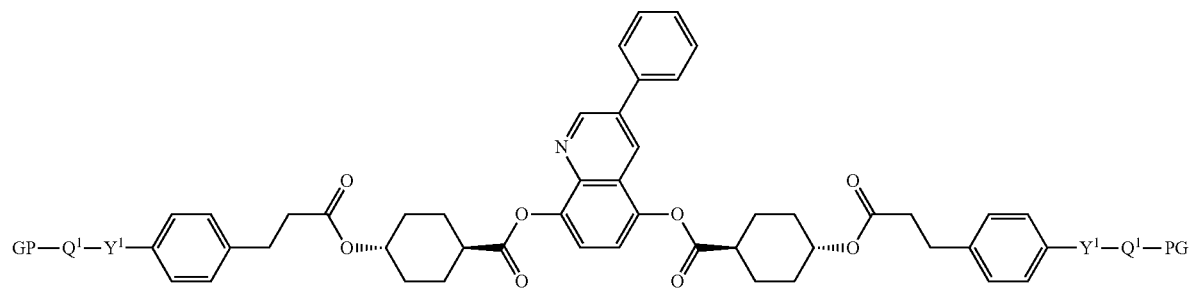
(1-2-4)
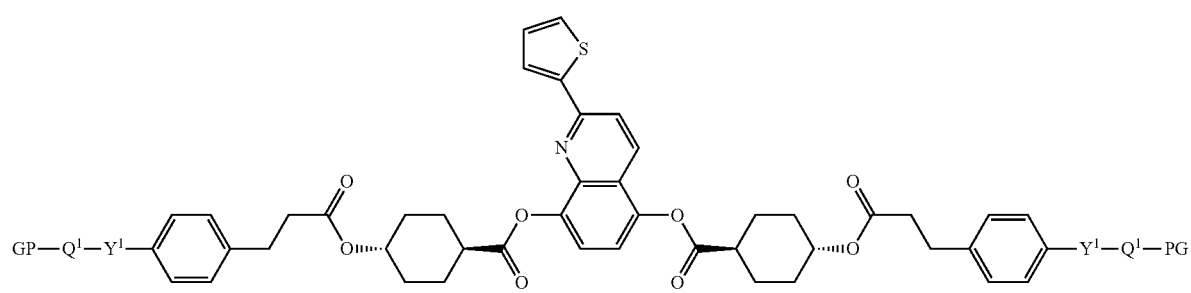
(1-2-5)
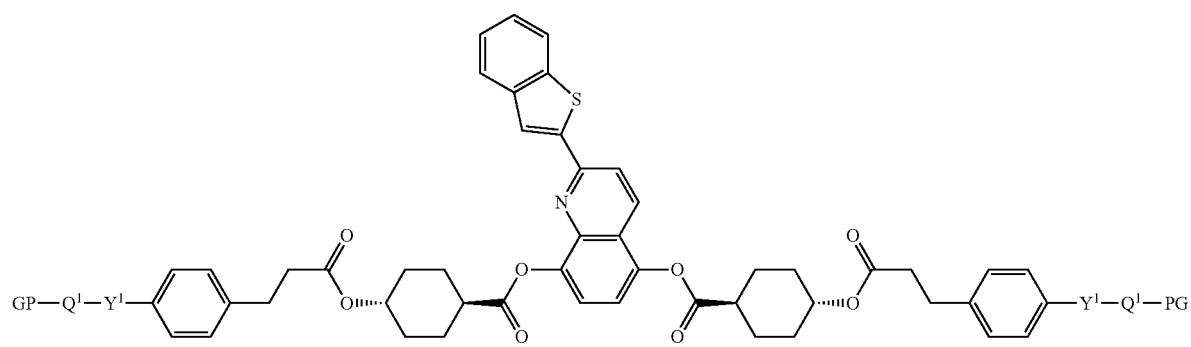
(1-2-6)
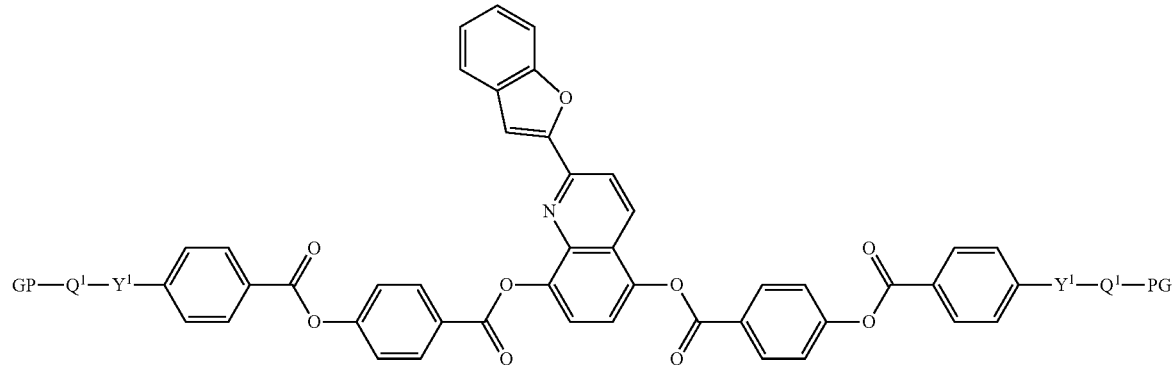

-continued
(1-2-7)
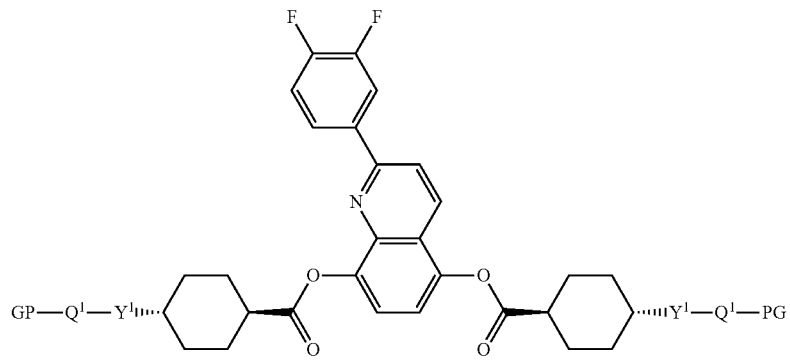
(1-2-8)
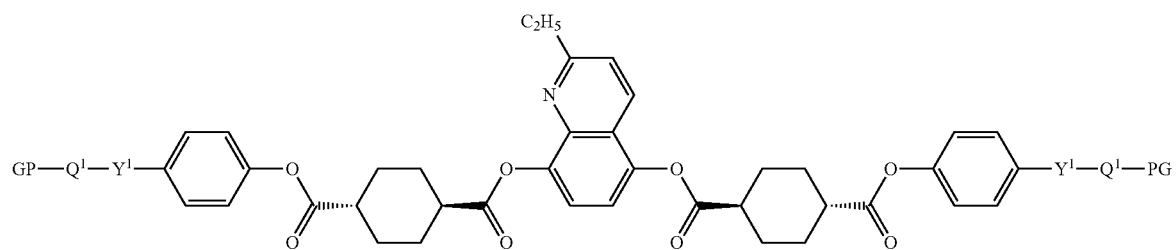
(1-2-9)
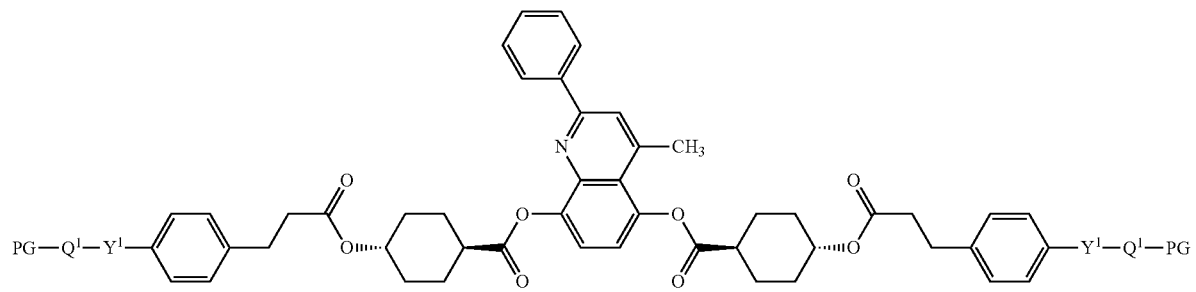
(1-2-10)
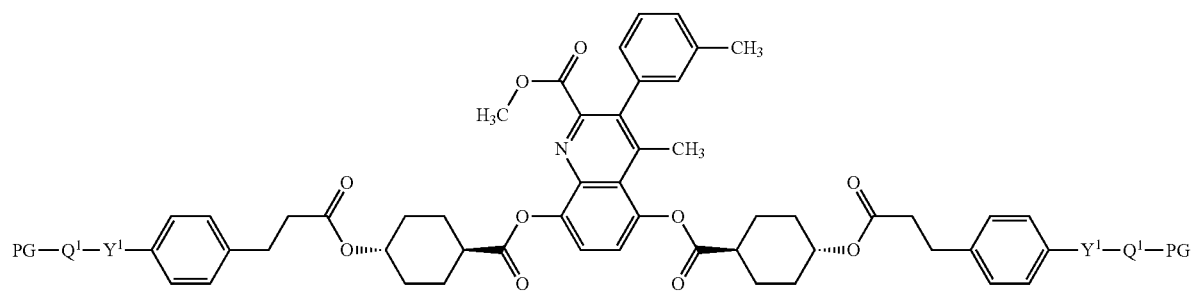

(1-2-11)
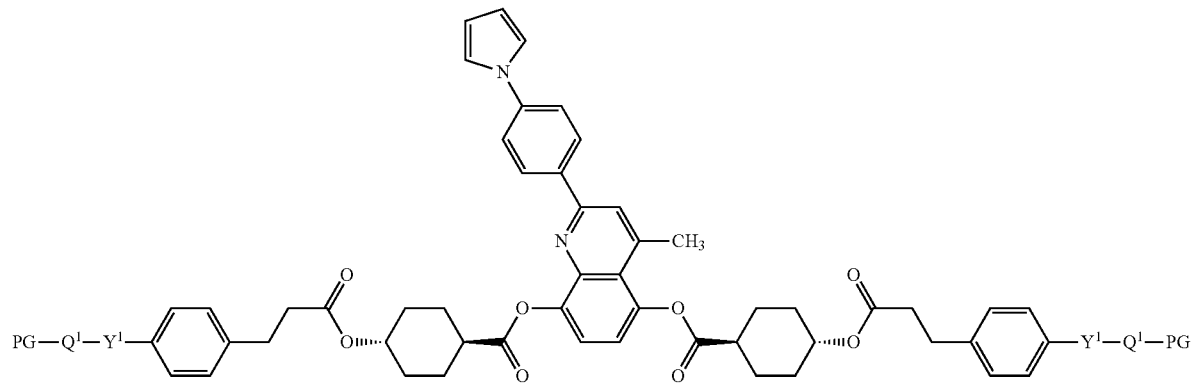
(1-2-12)
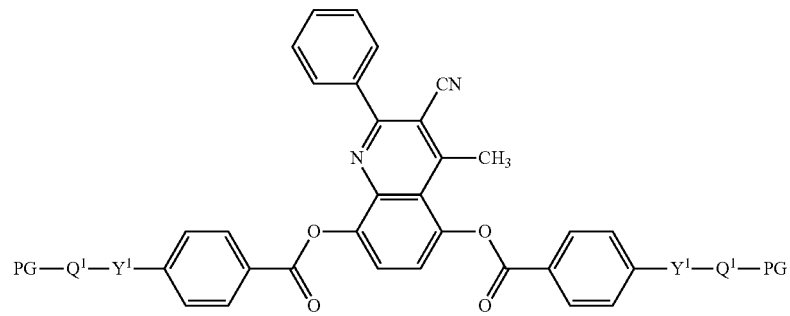
(1-2-13)
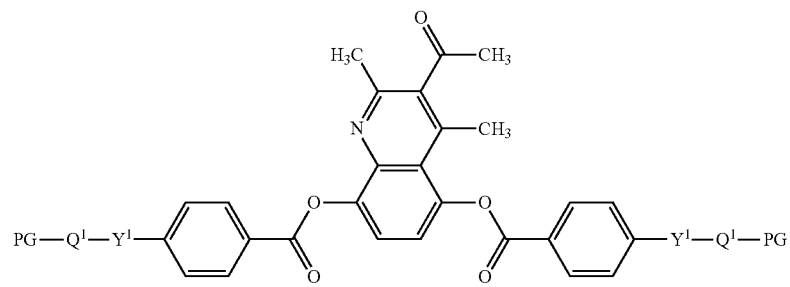
(1-2-14)
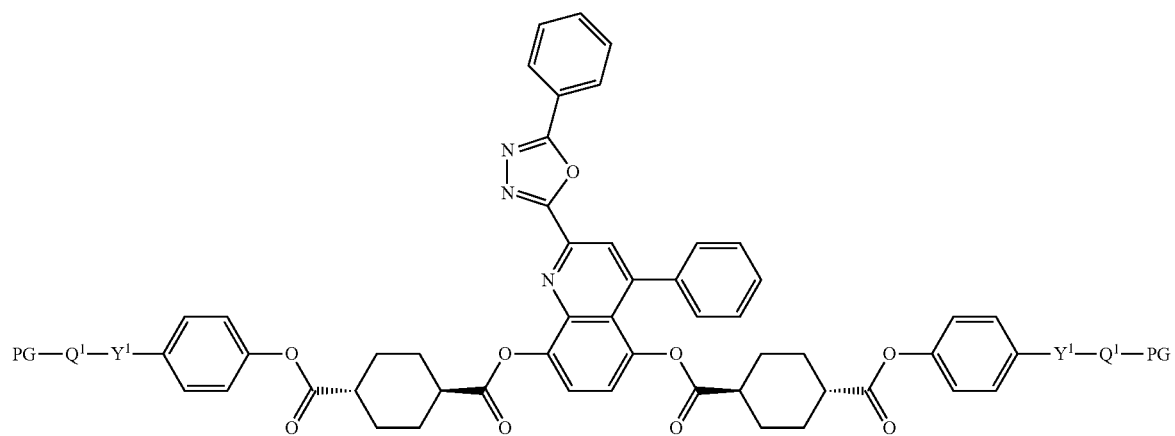

-continued
(1-3-1)
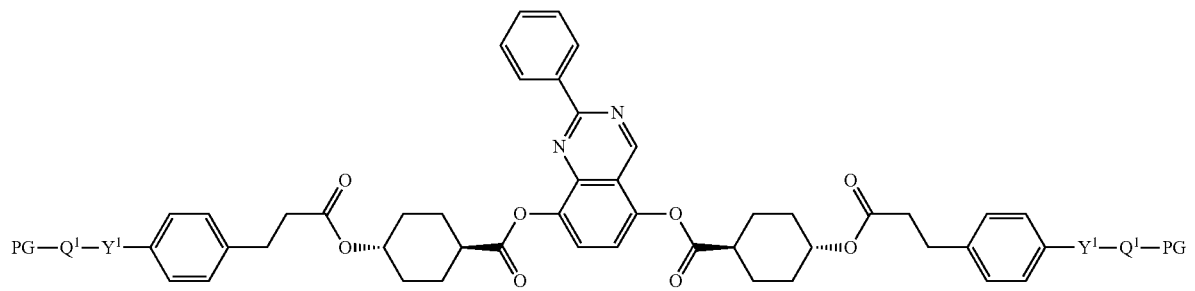
(1-3-2)
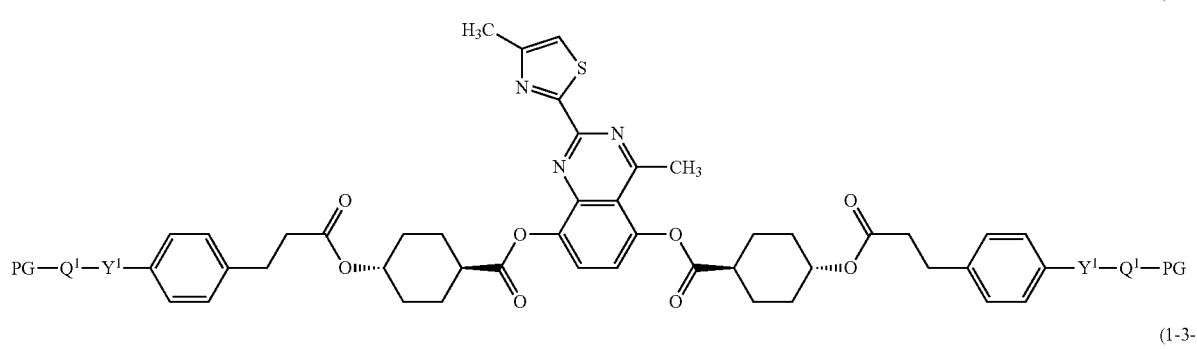
(1-3-3)
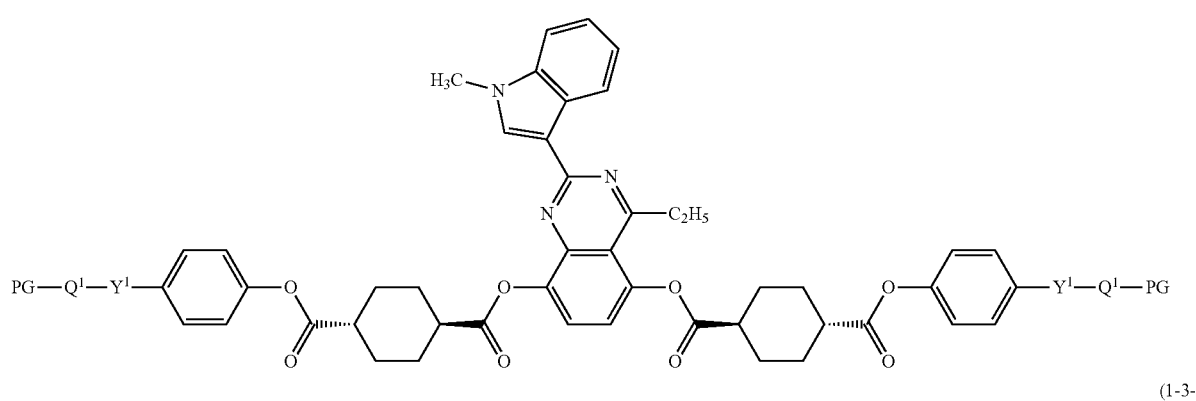
(1-3-4)
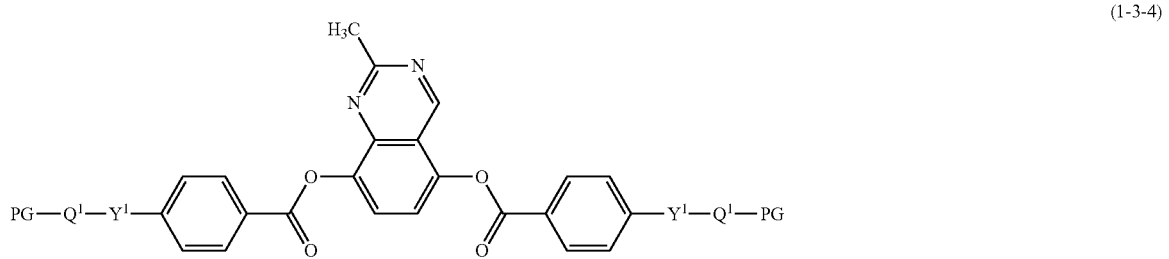
(1-3-5)
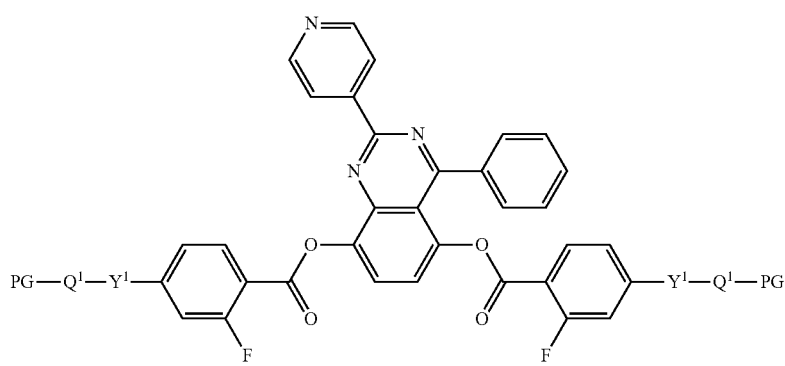

-continued
(1-4-1)
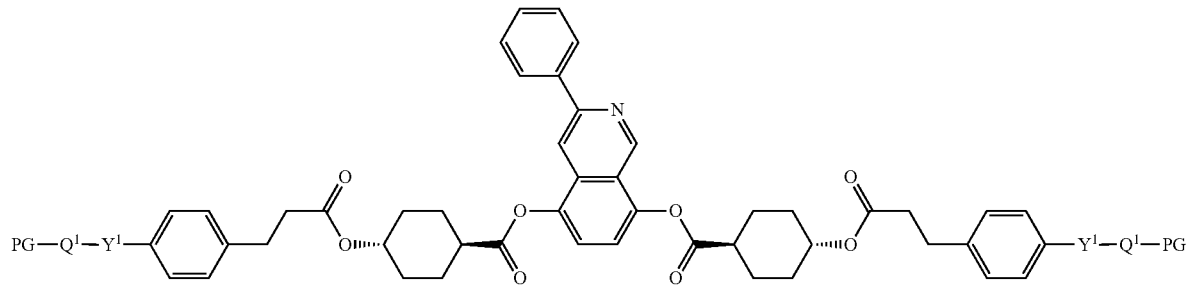
(1-4-2)
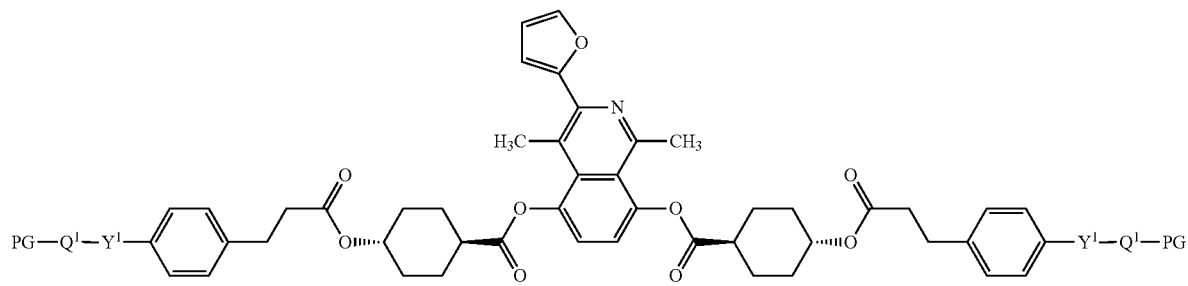
(1-4-3)
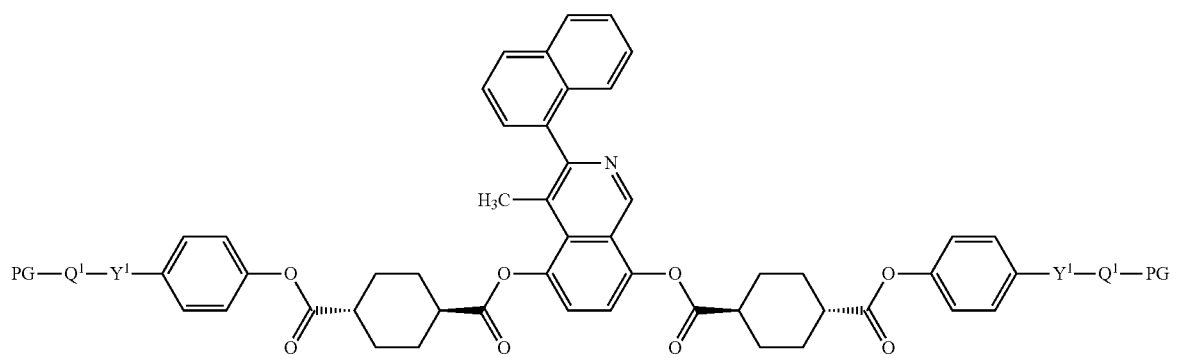
(1-4-4)
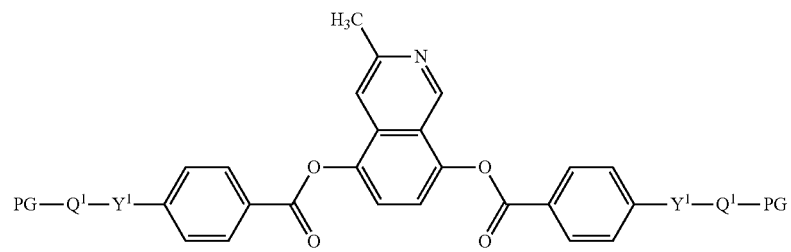
(1-4-5)
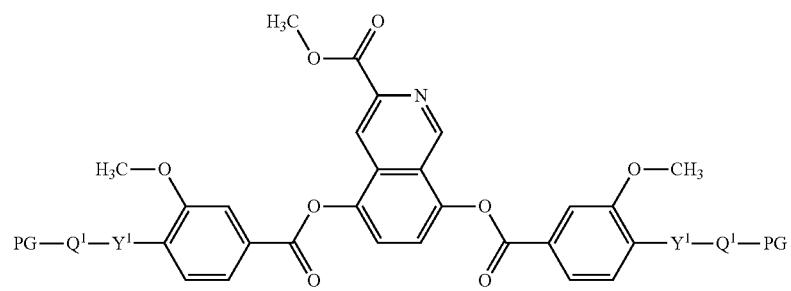

-continued
(1-4-6)
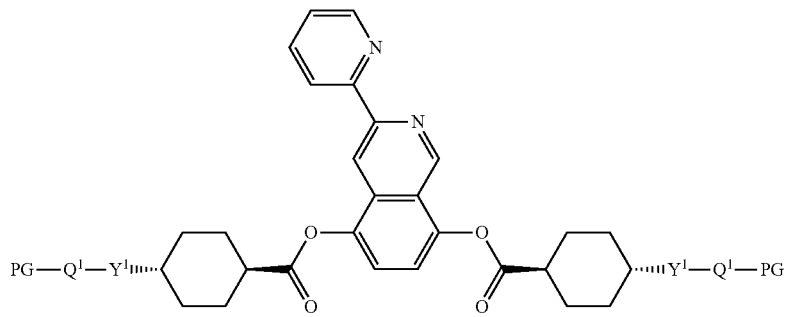
(1-4-7)
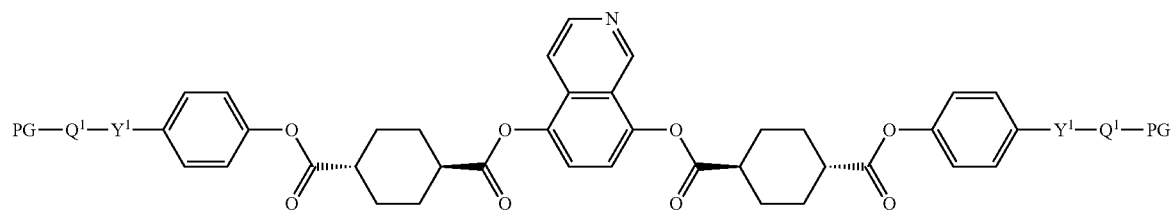
(1-5-1)
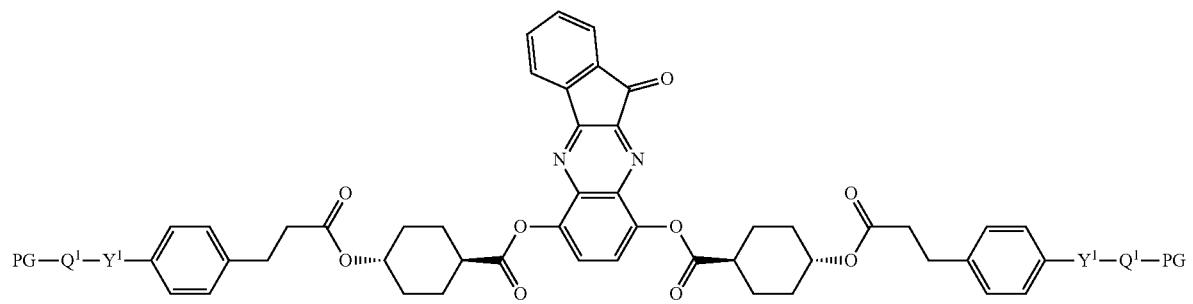
(1-5-2)
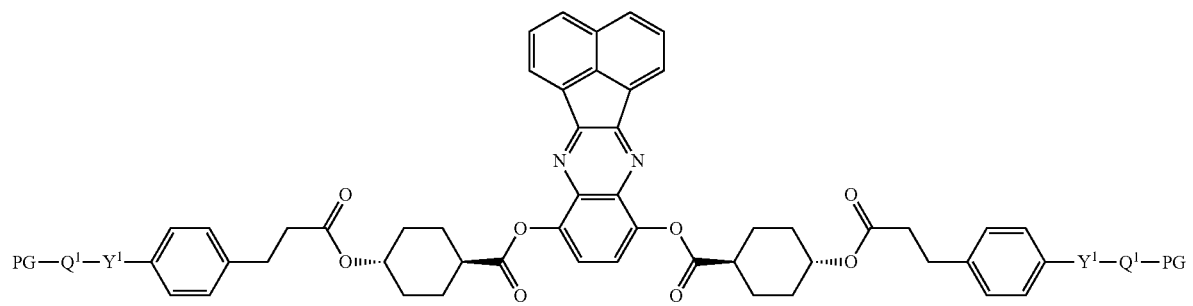
(1-5-3)
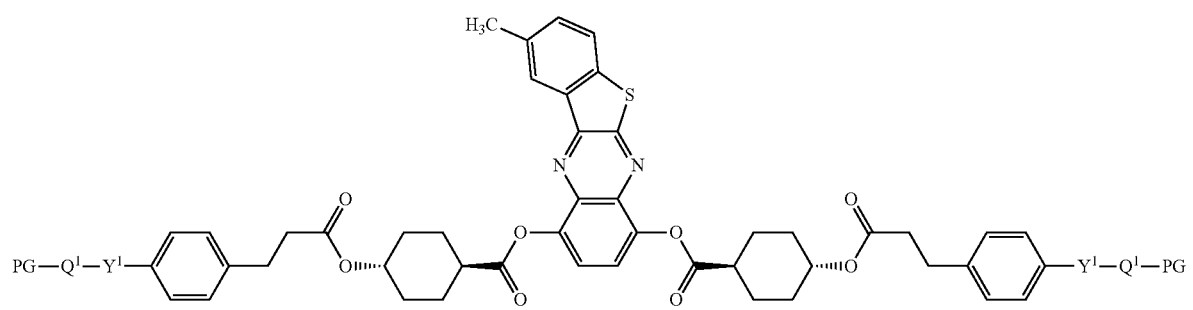

(1-5-4)
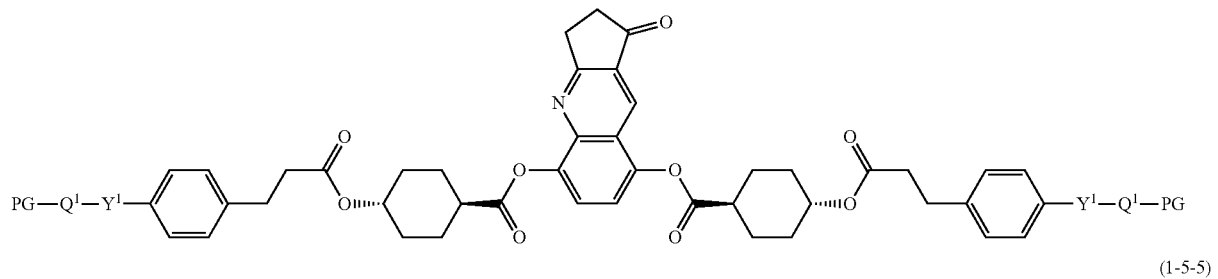
(1-5-5)
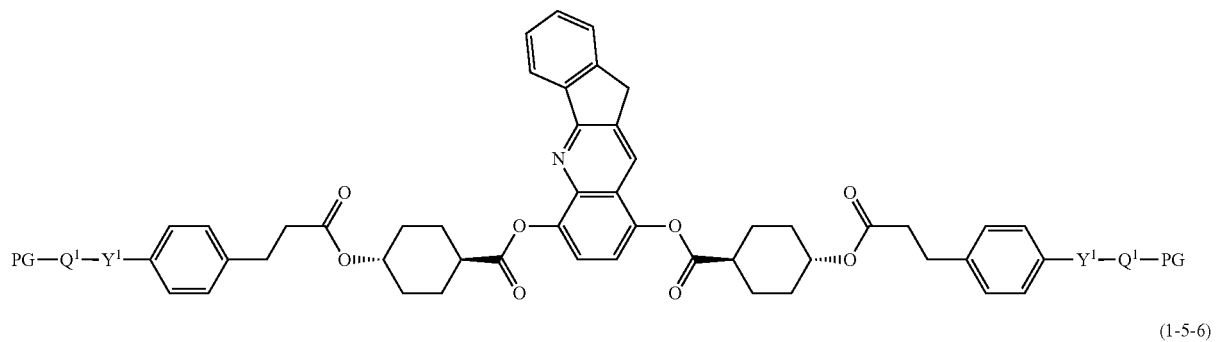
(1-5-6)
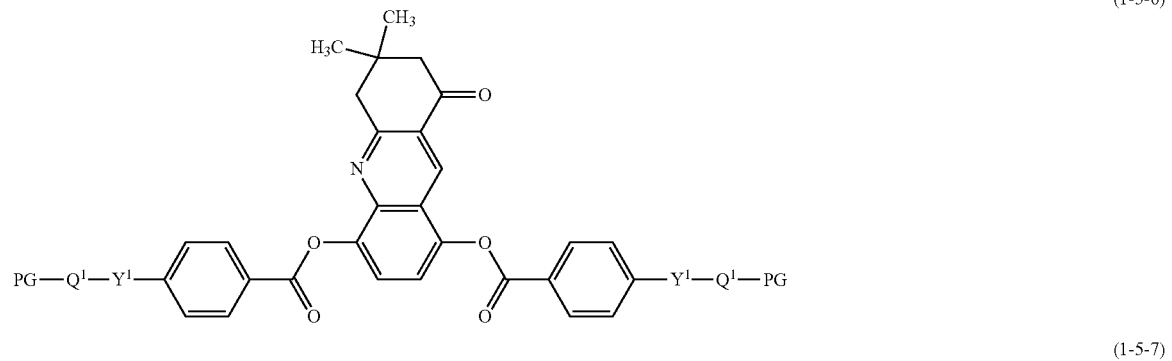
(1-5-7)
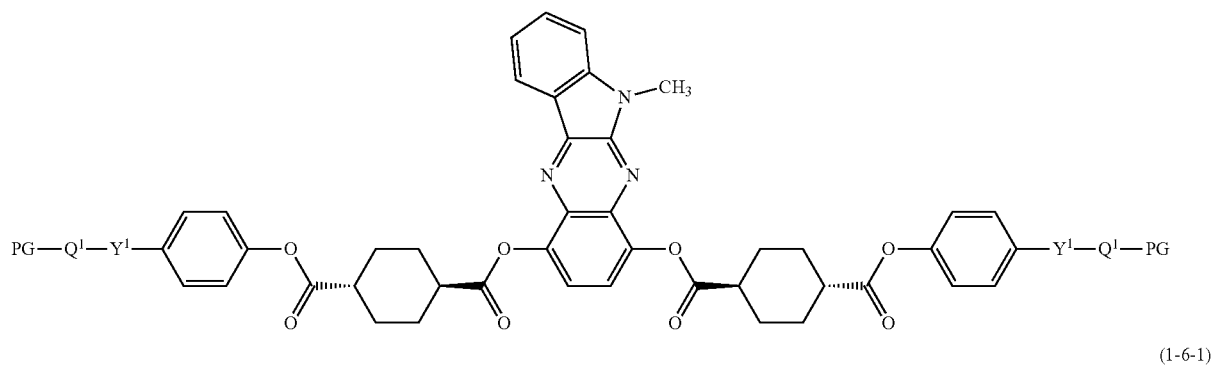
(1-6-1)
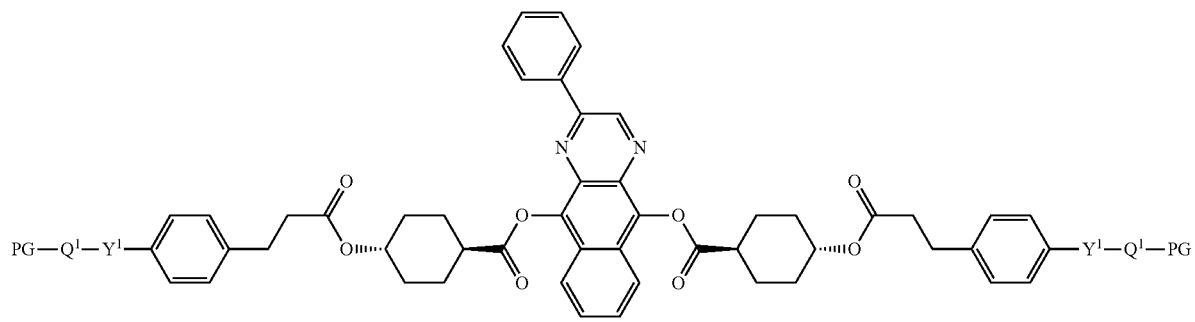

-continued

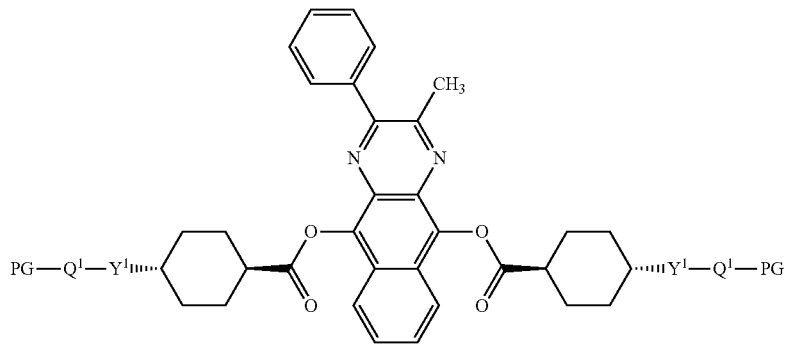

(1-6-2)

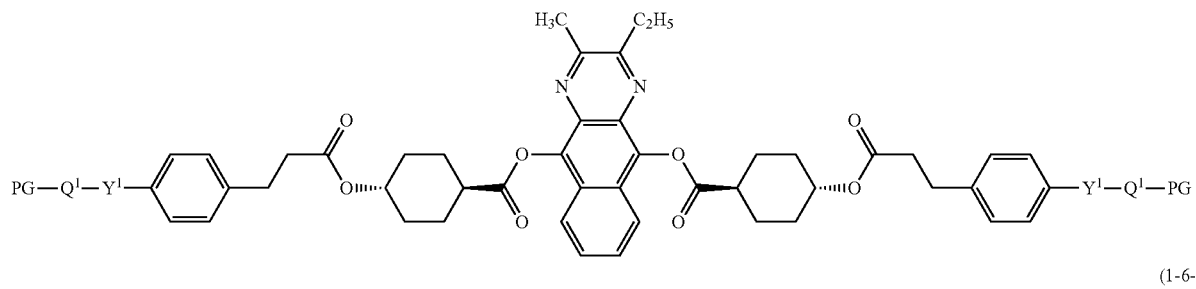

(1-6-3)

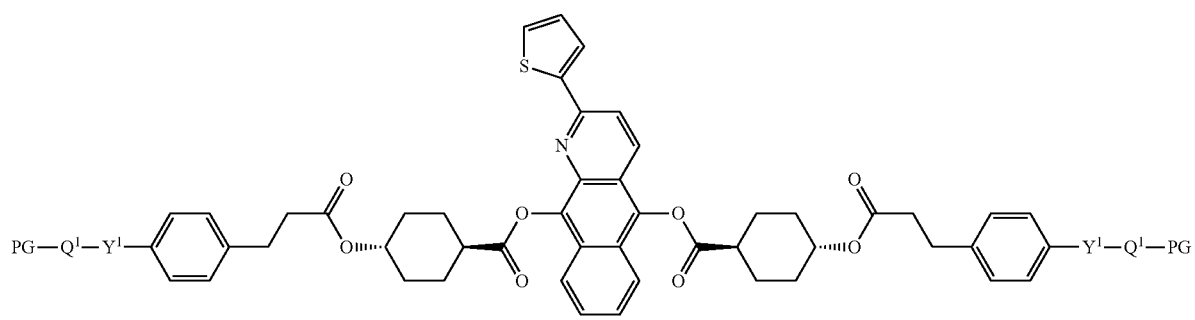

(1-6-4)

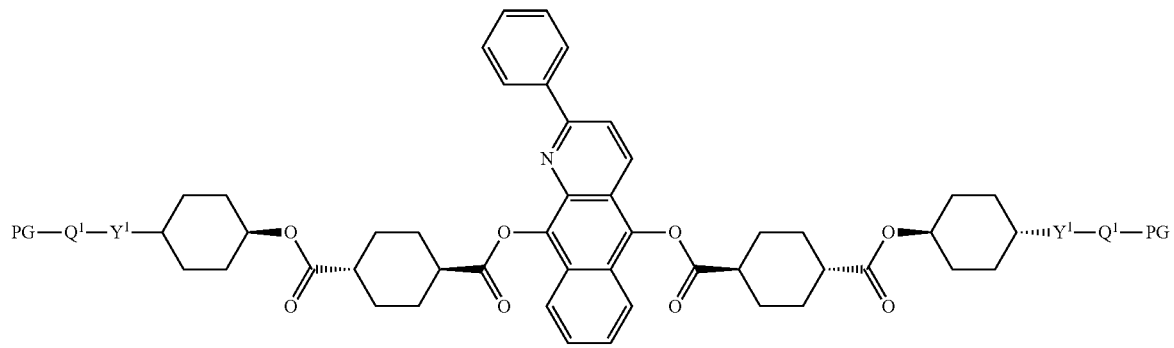

(1-6-5)

In formula (1-1-1) to formula (1-1-12), formula (1-2-1) to formula (1-2-14), formula (1-3-1) to formula (1-3-5), formula (1-4-1) to formula (1-4-7), formula (1-5-1) to formula (1-5-7) and formula (1-6-1) to formula (1-6-5), $Y^1$ is independently a single bond, —O—, —COO—, —OCO— or —OCOO—, $Q^1$ is independently a single bond or alkylene having 1 to 20 carbons, and in the alkylene, at least one piece of —CH$_2$— may be replaced by —O—, —COO— or —OCO—, and PG is independently any one of polymerizable groups represented by formula (PG-1) to formula (PG-9).

Synthesis of Compound (1)

The polymerizable liquid crystal compound represented by formula (1) can be synthesized by combining publicly-known techniques in synthetic organic chemistry. Methods of introducing an objective terminal group, ring, and bonding group to a starting material are described in books such as Houben-Wyle, Methods of Organic Chemistry, Georg Thieme Verlag, Stuttgart, Organic Syntheses, John Wily & Sons, Inc., Organic Reactions, John Wily & Sons Inc., Comprehensive Organic Synthesis, Pergamon Press and New Experimental Chemistry Course (Shin Jikken Kagaku Koza in Japanese) (Maruzen).

When a structure of G in compound (1) has a quinoxaline skeleton, compound (1) can be synthesized through a condensation reaction of an o-phenylenediamine derivative, with α-ketoaldehydes or α-diketones. Specifically, an intermediate of compound (1) can be synthesized through reaction steps represented by the formula described below.

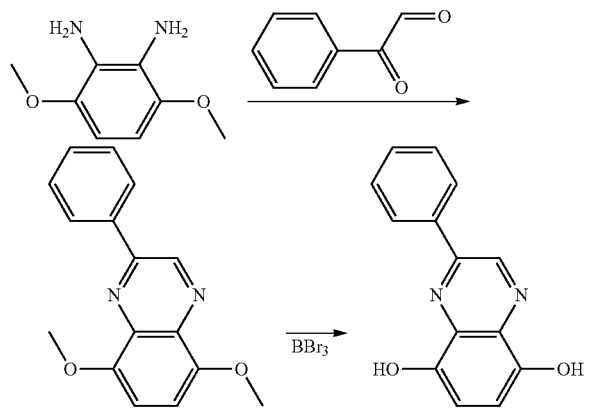

Compound (1) can be synthesized by deprotecting a dimethoxyquinoxaline compound obtained by a reaction of 1,2-diamino-3,6-dimethoxybenzene with phenylglyoxal, and subsequently diesterifying the resulting material.

When the structure of G in compound (1) has a quinoline skeleton, through a method such as a method of Friedlander synthesis, Pfitzinger synthesis, Skraup synthesis, Doebner-von Miller synthesis, Knorr synthesis, Combe synthesis, and Conrad-Limpach synthesis, compound (1) can be synthesized. When the structure of G in compound (1) has an isoquinoline skeleton, through a method of Pomeranz-Fritsch synthesis, Schlitter-Muller synthesis, Bischler-Napieralski synthesis or the like, compound (1) can be synthesized. When the structure of G of compound (1) is a quinazoline skeleton, through a method of Niementowski synthesis or the like, compound (1) can be synthesized.

As in the reaction formula described below, 4-cyclohexylene can be introduced thereto by using 4-hydroxycyclohexanecarboxylic acid or the like.

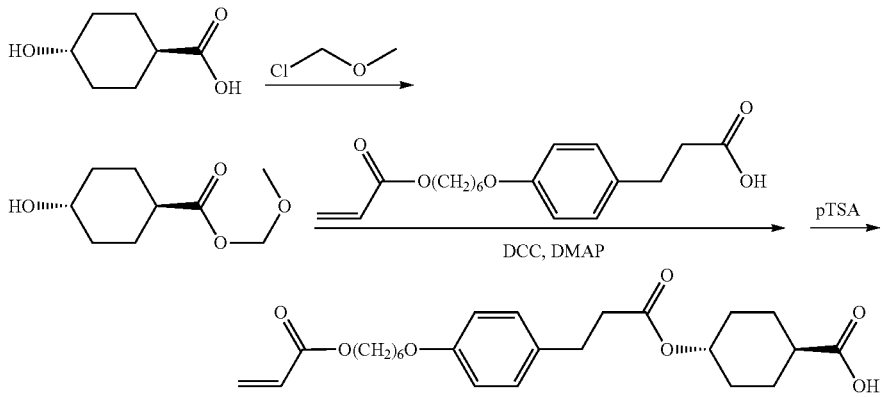

Here, in the above-described formula, r is an integer from 2 to 20.

Polymerizable Liquid Crystal Composition

The polymerizable liquid crystal composition of the invention has the liquid crystal phase of a nematic phase or a smectic phase at room temperature.

Film formation on which surface is subjected to alignment treatment on a plastic substrate subjected to alignment treatment such as rubbing treatment, after the polymerizable liquid crystal composition of the invention, induces homogeneous alignment or tilt alignment of non-substrate-embedded liquid crystal polymerization film which material is the polymerizable liquid crystal composition.

Addition of an optically active compound to the polymerizable liquid crystal composition of the invention induces twist alignment of the non-substrate-embedded liquid crystal polymerization film made of the polymerizable liquid crystal composition as the raw material.

Addition of a compound having a cardo structure to the polymerizable liquid crystal composition of the invention induces, homeotropic alignment of the non-substrate-embedded liquid crystal polymerization film prepared made of polymerizable liquid crystal composition as the raw material.

Addition of a compound having a polar group at a terminal to the polymerizable liquid crystal composition of the invention induces, homeotropic alignment of the non-substrate-embedded liquid crystal polymerization film made of the polymerizable liquid crystal composition as the raw material. Here, the polar group means a hydroxyl group, a carboxyl group, an amino group, a thiol group, a sulfonate group, an ester group, an amide group, an ammonium group and other hydrophilic groups.

For the purpose of reducing positive chromatic dispersion characteristics and preventing phase separation with the organic solvent, compound (1) is preferably contained, from about 4 wt % to 50 wt % based on the total weight of the polymerizable liquid crystal composition as the raw material of the liquid crystal polymerization film-kind.

The polymerizable liquid crystal composition of the invention can contain compounds (M1), (M2) and/or (M3).

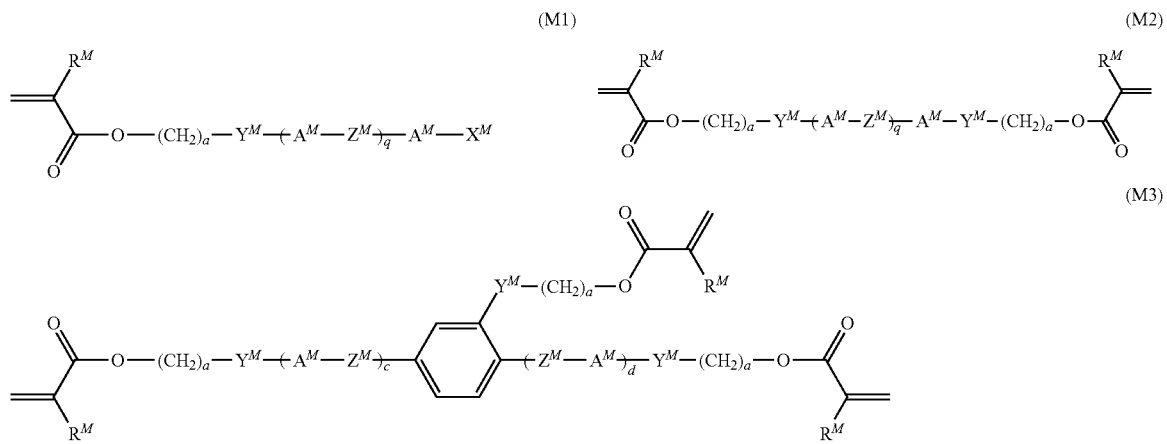

In formulas (M1), (M2) and (M3), $A^M$ are independently divalent group selected from 1,4-phenylene, 1,4-cyclohexylene, 1-cyclohexene-1,4-ylene, 2-cyclohexene-1,4-ylene, pyridine-2,5-diyl, 1,3-dioxane-2,5-diyl, naphthalene-2,6-diyl or fluorene-2,7-diyl, and in the divalent group, at least one hydrogen may be replaced by fluorine, chlorine, cyano, hydroxy, formyl, trifluoroacetyl, difluoromethyl, trifluoromethyl, alkyl having 1 to 5 carbons, alkoxy having 1 to 5 carbons, alkoxycarbonyl having 1 to 5 carbons or alkanoyl having 1 to 5 carbons, $Z^M$ are independently a single bond, —OCH₂—, —CH₂O—, —COO—, —OCO—, —COS—, —SCO—, —OCOO—, —CONH—, —NHCO—, —CF₂O—, —OCF₂—, —CH₂CH₂—, —CF₂CF₂—, —CH=CHCOO—, —OCOCH=CH—, —CH₂CH₂COO—, —OCOCH₂CH₂—, —CH=CH—, —N=CH—, —CH=N—, —N=C(CH₃)—, —C(CH₃)=N—, —N=N—, —C≡C— or —C≡C—C≡C—, $X^M$ is hydrogen, fluorine, chlorine, trifluoromethyl, trifluoromethoxy, cyano, alkyl having 1 to 20 carbons, alkenyl having 2 to 20 carbons, alkoxy having 1 to 20 carbons or alkoxycarbonyl having 1 to 20, q is an integer from 1 to 4, c and d are independently an integer from 0 to 3, and satisfy an expression 1≤c+d≤4, a is an integer from 0 to 20, $R^M$ is hydrogen or methyl, and $Y^M$ is a single bond, —O—, —COO—, —OCO— or —OCOO—.

Compounds (M1-1) to (M1-13) are examples of compound (M1).

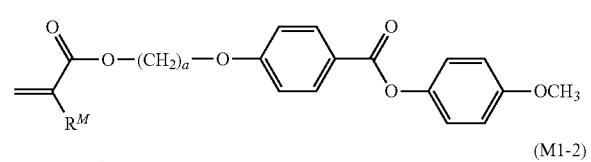
(M1-1)

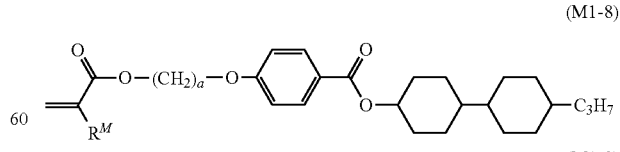
(M1-2)

-continued

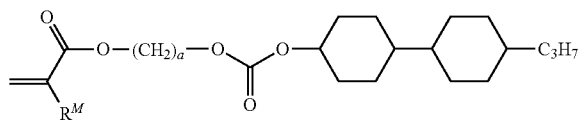
(M1-3)

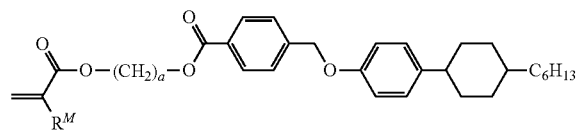
(M1-4)

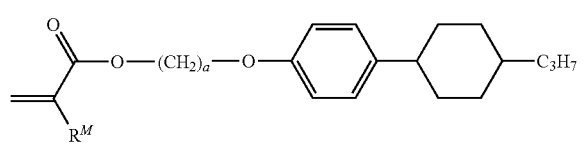
(M1-5)

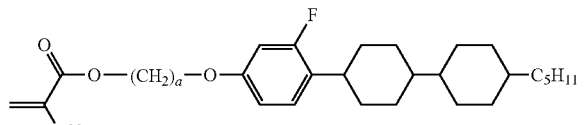
(M1-6)

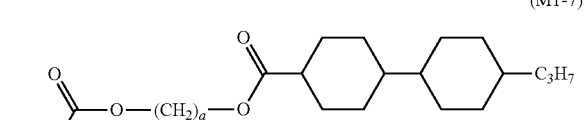
(M1-7)

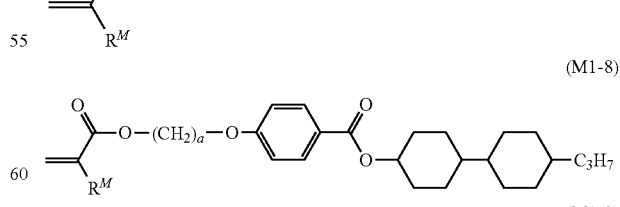
(M1-8)

(M1-9)

(M1-10)
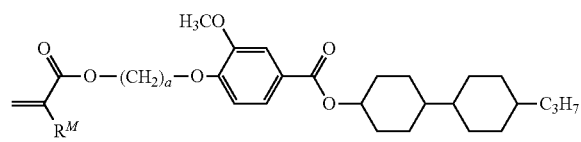
(M1-11)
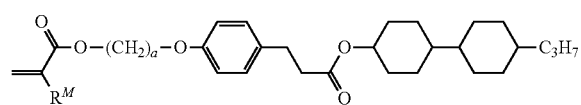
(M1-12)
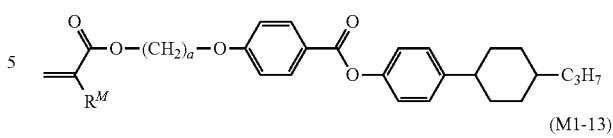
(M1-13)
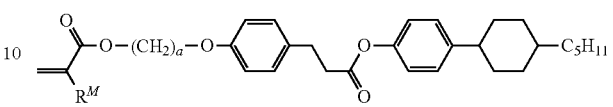
In formulas (M1-1) to (M1-13), $R^M$ is hydrogen or methyl, and a is an integer from 1 to 12.
Compounds (M2-1) to (M2-10) are examples of compound (M2).
(M2-1)
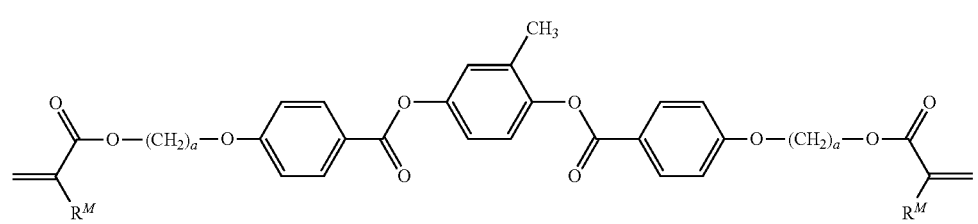
(M2-2)
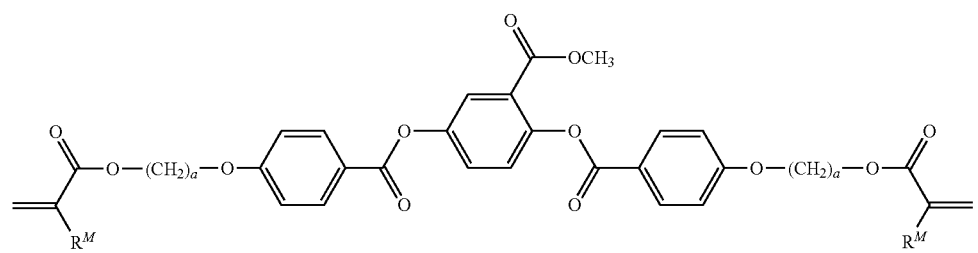
(M2-3)
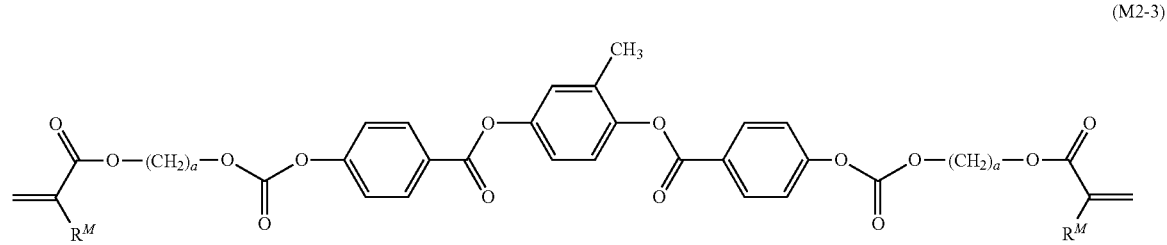
(M2-4)
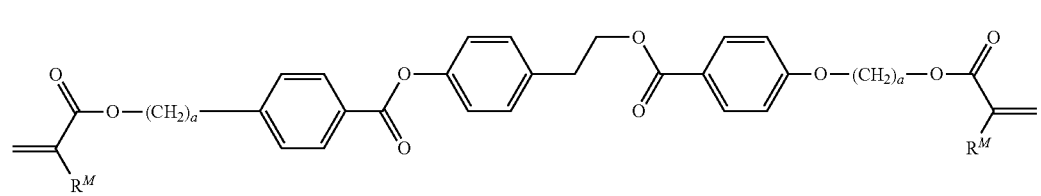
(M2-5)
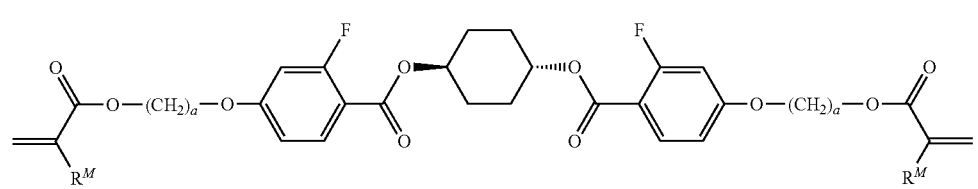

(M2-6)
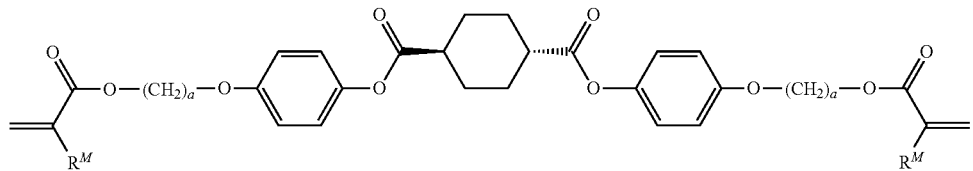
(M2-7)
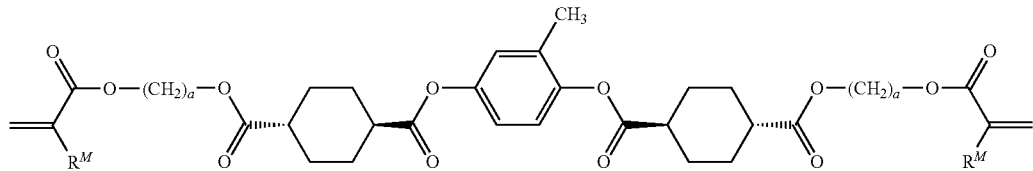
(M2-8)
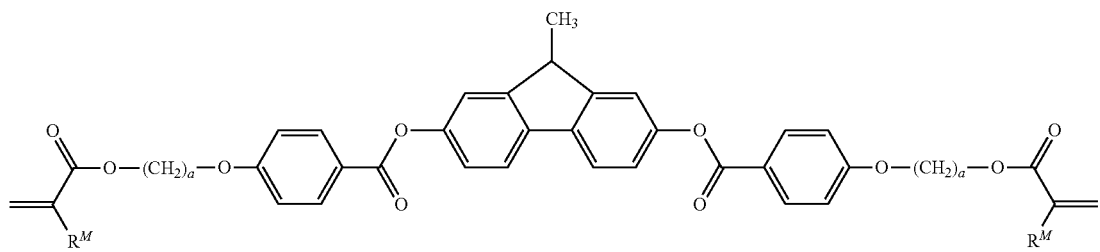
(M2-9)
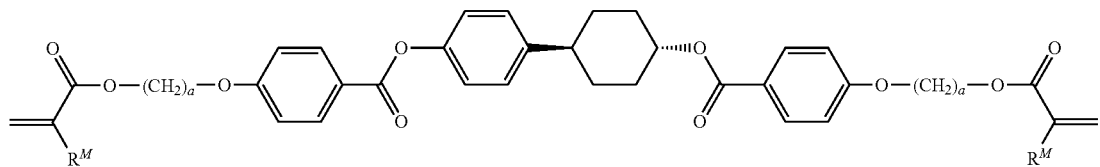
(M2-10)
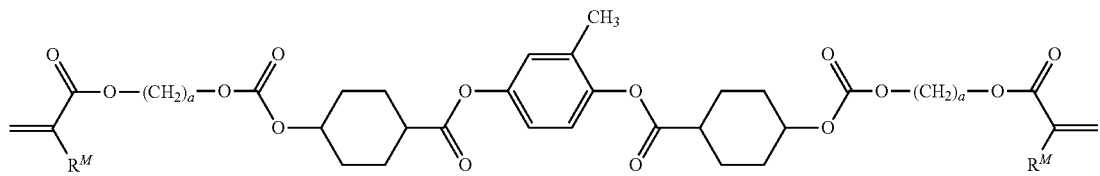
In formulas (M2-1) to (M2-10), $R^M$ are independently hydrogen or methyl, and a are independently an integer from 1 to 12.
Compounds (M3-1) to (M3-10) are examples of compound (M3).
(M3-1)
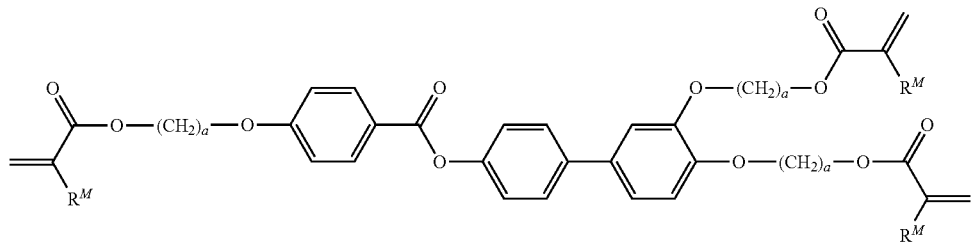

(M3-2)
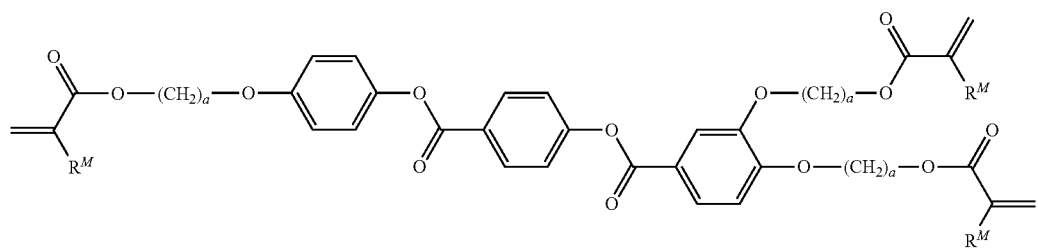
(M3-3)
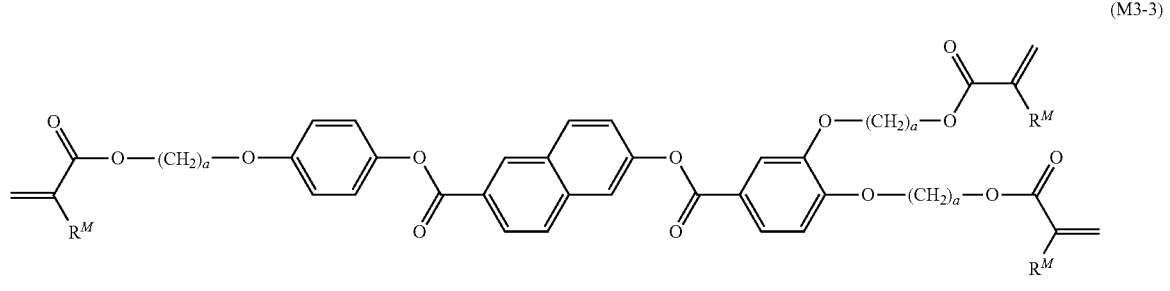
(M3-4)
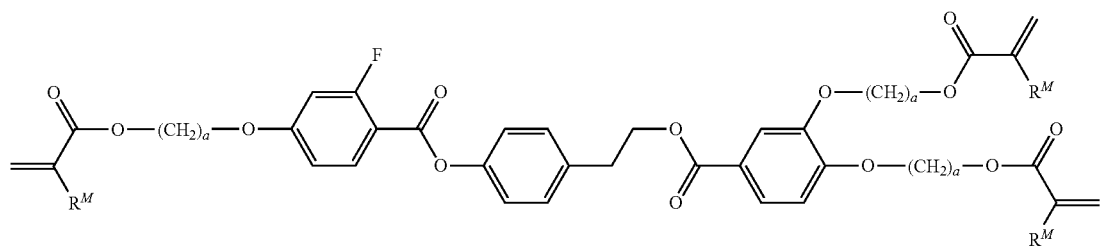
(M3-5)
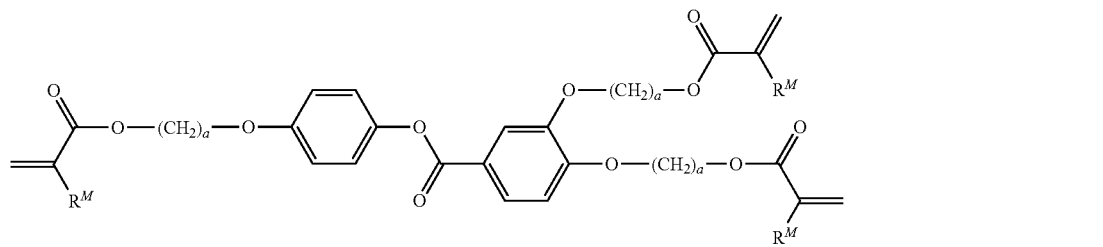
(M3-6)
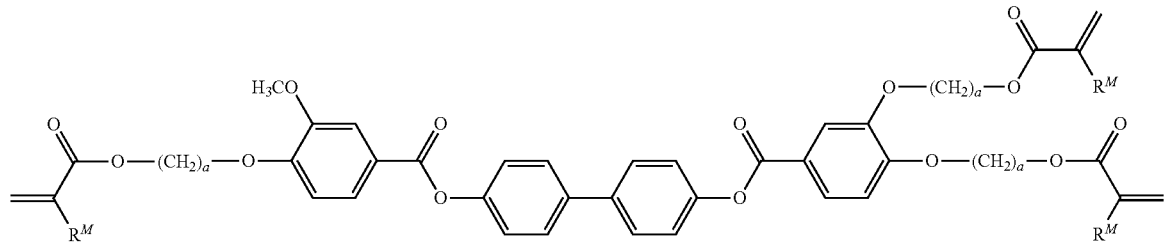
(M3-7)
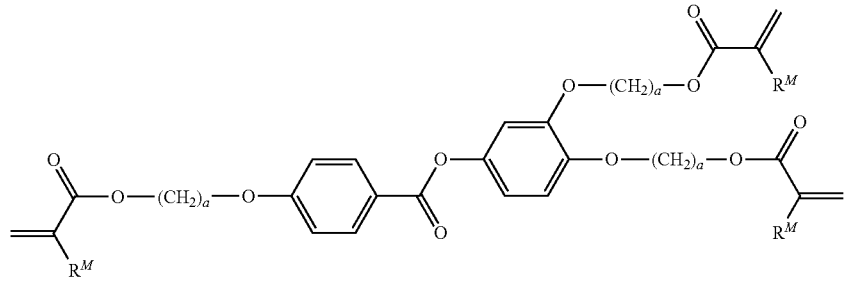

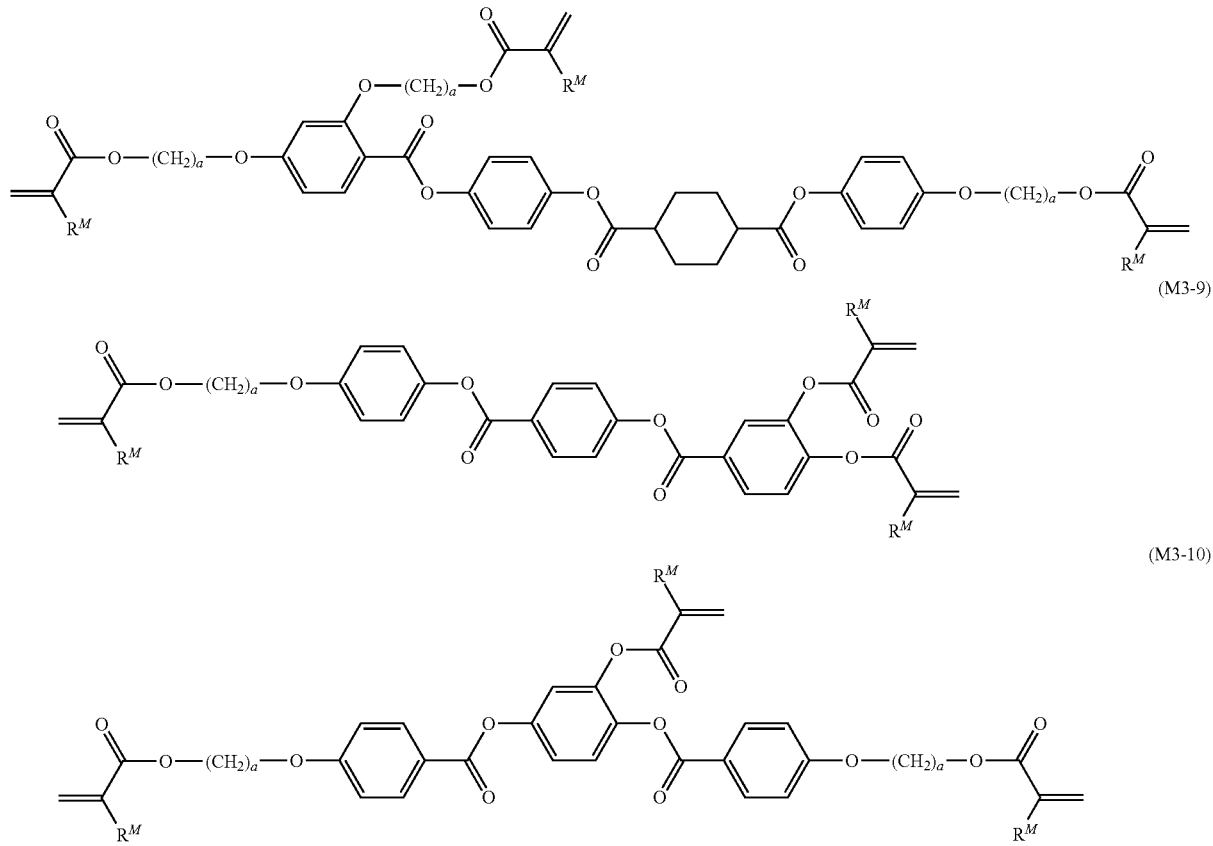

In formulas (M3-1) to (M3-10), $R^M$ is independently hydrogen or methyl, and a are independently an integer from 1 to 12.

The liquid crystal composition of the invention may contain a polymerizable liquid crystal compound having no polymerizable group. The polymerizable liquid crystal compound having no polymerizable group can be selected from compounds described in LiqCryst, LCI Publisher GmbH, Hamburg, Germany, being a database of the liquid crystal compounds. Specific examples thereof include a compound represented by formula (LC) below.

In formula (LC), $A^2$ is independently divalent group selected from 1,4-phenylene, 1,4-cyclohexylene, pyridine-2,5-diyl, 1,3-dioxane-2,5-diyl and naphthalene-2,6-diyl, and in the divalent group, at least one of hydrogen may be replaced by fluorine, chlorine, cyano, hydroxy, formyl, trifluoroacetyl, difluoromethyl, trifluoromethyl, alkyl having 1 to 5 carbons, alkoxy having 1 to 5 carbons, alkoxycarbonyl having 1 to 5 carbons or alkanoyl having 1 to 5 carbons, $Z^2$ is independently a single bond or alkylene having 1 to 20 carbons, and in the alkylene, at least one of —CH$_2$— may be replaced by —O—, —CO—, —COO—, —OCO—, —CH=CH—, —CF=CF— or —C≡C—, and in the alkylene, at least one piece of hydrogen may be replaced by halogen, b is an integer from 1 to 5, $R^3$ is independently hydrogen, fluorine, chlorine, cyano, hydroxy, formyl, trifluoroacetyl, difluoromethyl, trifluoromethyl, alkyl having 1 to 10 carbons or alkoxy having 1 to 10 carbons, and in the alkyl, at least one piece of —CH$_2$— may be replaced by —O— or —CH=CH—.

In a viewpoint of hardness of the liquid crystal polymerization film, a content of compound (LC) in the polymerizable liquid crystal composition of the invention is preferably from about 0 to about 50 wt % based on the total weight of the polymerizable liquid crystal composition as the raw material of the liquid crystal polymerization film-kind.

Compound or the Like to be Added to Polymerizable Liquid Crystal Composition

At least one kind of the polymerizable liquid crystal composition of the invention can be added for each function.

The polymerizable liquid crystal composition of the invention may contain a surfactant. The surfactant is classified into an ionic surfactant or a nonionic surfactant. The nonionic surfactant improves smoothness of the liquid crystal polymerization film. The nonionic surfactant is effective in suppressing tilt alignment of the liquid crystal polymerization film on the air interface side. Consequently, addition of the nonionic surfactant to the polymerizable liquid crystal composition is preferred. the nonionic surfactant as a silicone-based nonionic surfactant, a fluorine-based nonionic surfactant, a vinyl-based nonionic surfactant and a hydrocarbon-based nonionic surfactant are the nonionic surfactants.

For easily forming uniform alignment of liquid crystal polymerization film, and for improving applicability of painting of the polymerizable liquid crystal composition, based on the total weight of the polymerizable liquid crystal composition, 0.0001 to about 0.5 wt % of surfactant in the polymerizable liquid crystal composition is preferred.

The ionic surfactant as a titanate-based compound, and a compound of imidazoline, quaternary ammonium salt, alkylamine oxide, a polyamine derivative, a polyoxyethylene-polyoxypropylene condensate, polyethyleneglycol and an ester thereof, sodium lauryl sulfate, ammonium lauryl sulfate, lauryl sulfate amines, alkyl-substituted aromatic sulfonate, alkyl phosphate, an aliphatic or aromatic sulfonic acid-formalin condensate, laurylamide propylbetaine, lauryl aminoacetic betaine, polyethyleneglycol fatty acid esters, polyoxyethylene alkylamine, perfluoroalkyl sulfonate or perfluoroalkyl carboxylate are the ionic surfactant.

Linear polymer having a siloxane bonds, which introduced an organic group such as polyether and long-chain alkyl into side chain and/or at a terminal thereof, or the like, is silicone-based nonionic surfactant Compounds having perfluoroalkyl group or perfluoroalkenyl group, which groups have 2 to 7 carbons, or the like are fluorine-based nonionic surfactant.

(Meth)acryl-based polymers having from about 1,000 to about 1,000,000 as weight average molecular weight, or the like, are the vinyl-based nonionic surfactant.

For avoiding excessively-localized distribution of the polymerizable liquid crystal compound, the surfactant may have a polymerizable group. The polymerizable group introduced into the surfactant is preferably a UV reaction type functional group from a viewpoint of reactivity with the polymerizable liquid crystal compound.

For improving hardness of liquid crystal polymerization film, addition of the surfactant having the polymerizable group is preferred.

The polymerizable liquid crystal composition of the invention may also contain a non-liquid crystalline polymerizable compound. For maintaining the liquid crystal phase, About 30 wt % or less of the non-liquid crystalline polymerizable compound in the polymerizable liquid crystal composition, based on the total weight of the polymerizable liquid crystal composition, is preferred.

Specific examples of the non-liquid crystalline polymerizable compounds include compounds such as and the compound having no liquid crystallinity which are vinyl derivatives, styrene derivatives, (meth)acrylic acid derivatives, oxirane derivatives, oxetane derivatives, sorbic acid derivatives, a fumaric acid derivatives and an itaconic acid derivatives.

From viewpoints of improving of mechanical strength of the liquid crystal polymerization film, or of chemical resistance, or both thereof, addition of a compound having two or more polymerizable groups to the polymerizable liquid crystal composition is preferred. From a viewpoint of an improvement of adhesion between the liquid crystal polymerization film and the substrate, addition of a non-liquid crystalline polymerizable compound having a polar group in a side chain and/or at a terminal, to the polymerizable liquid crystal composition, is preferred.

Styrene, nucleus-substituted styrene, acrylonitrile, vinyl chloride, vinylidene chloride, vinyl pyridine, N-vinyl pyrrolidone, vinylsulfonic acid, fatty acid vinyl ester, α,β-ethylenic unsaturated carboxylic acid, alkyl ester of (meth)acrylic acid in which the number of carbons of alkyl is 1 to 18, hydroxyalkyl ester of (meth)acrylic acid in which the number of carbons of hydroxyalkyl is 1 to 18, aminoalkyl ester of (meth)acrylic acid in which the number of carbons of aminoalkyl is 1 to 18, ether oxygen-containing alkyl ester of (meth)acrylic acid in which the number of carbons of ether oxygen-containing alkyl is 3 to 18, N-vinylacetamide, p-t-butyl vinyl benzoate, N,N-dimethylaminovinyl benzoate, vinyl benzoate, vinyl pivalate, 2,2-dimethylbutane acid vinyl, vinyl 2,2-dimethylpentanoate, vinyl 2-methyl-2-butanoate, vinyl propionate, vinyl stearate, vinyl 2-ethyl-2-methylbutanate, dicyclopentanyloxylethyl (meth)acrylate, isobornyloxylethyl (meth)acrylate, isobornyl (meth)acrylate, adamanthyl (meth)acrylate, dimethyladamanthyl (meth)acrylate, dicyclopentanyl (meth)acrylate, dicyclopentenyl (meth)acrylate, 2-acryloyloxyethyl succinate, 2-acryloyloxyethylhexahydrophthalic acid, 2-acryloyloxyethyl phthalic acid, 2-acryloyloxyethyl-2-hydroxyethyl phthalic acid, 2-acryloyloxyethyl acid phosphate, 2-methacryloyloxyethyl acid phosphate, mono(meth)acrylate, polypropylene glycol, which has a polymerization degree of 2 to 100, and which is capped by di(meth)acrylate ester or an alkyl group having 1 to 6 carbons, and mono(meth)acrylate ester of a copolymer of polyethylene glycol and, ethylene oxide and polypropylene oxide, and the like are the non-liquid crystalline polymerizable compounds being the monofunctional compound. Vinyl acetate and the like are "fatty acid vinyl ester" herein.

Acrylic acid, methacrylic acid, maleic acid, fumaric acid and itaconic acid are "α,β-ethylenic unsaturated carboxylic acid" herein.

Methoxyethyl ester, ethoxyethyl ester, methoxypropyl ester, methylcarbitol ester, ethylcarbitol ester, butylcarbitol ester and the like are "ether oxygen-containing alkyl ester of (meth)acrylic acid in which the number of carbons of ether oxygen-containing alkyl is 3 to 18" herein.

Such a material is the non-liquid crystalline polymerizable compound being a difunctional compound as 1,4-butanediol diacrylate, 1,6-hexanediol diacrylate, 1,9-nonanediol diacrylate, neopentyl glycol diacrylate, dimethylol tricyclodecane diacrylate, triethylene glycol diacrylate, dipropylene glycol diacrylate, tripropylene glycol diacrylate, tetraethylene glycol diacrylate, bisphenol A EO-added diacrylate, bisphenol A glycidyl diacrylate, polyethyleneglycol diacrylate and a methacrylate compound of compounds described above.

Such a material is the non-liquid crystalline polymerizable compound being a trifunctional or higher-functional polyfunctional compound as pentaerythritol triacrylate, trimethylolpropane triacrylate, trimethylol EO-added triacrylate, trisacryloyloxyethyl phosphate, tris(acryloyloxyethyl)isocyanurate, alkyl-modified dipentaerythritol triacrylate, EO-modified trimethylolpropane triacrylate, PO-modified trimethylolpropane triacrylate, pentaerythritol tetraacrylate, alkyl-modified dipentaerythritol tetraacrylate, ditrimethylolpropanetetraacrylate, dipentaerythritol hexaacrylate, dipentaerythritolmonohydroxypentaacrylate, alkyl-modified dipentaerythritol pentaacrylate, pentaerythritol tri(meth)acrylate, trimethylolpropane tri-(meth)acrylate, trimethylol EO-added tri(meth)acrylate, tris(meth)acryloyloxy ethyl phosphate, tris(meth)acryloyloxy ethyl, isocyanurate, alkyl-modified dipentaerythritol tri(meth)acrylate, EO-modified trimethylolpropane tri(meth)acrylate, PO-modified trimethylolpropane tri(meth)acrylate, pentaerythritol tetra(meth)acrylate, alkyl-modified dipentaerythritol tetra (meth)acrylate, ditrimethylol propanetetra (meth)acrylate, dipentaerythritol hexa(meth)acrylate dipentaerythritolmonohydroxy penta methacrylate and alkyl-modified dipentaerythritol pentamethacrylate.

Addition of the non-liquid crystalline polymerizable compound having a bisphenol structure or cardo structure to the polymerizable liquid crystal composition results in inducing an improvement of hardness of the liquid crystal polymerization film, and homeotropic alignment in the liquid crystal polymerization film. Compounds (α-1) to (α-3) and so forth each are a polymerizable fluorene derivative having a cardo structure.

causing homocleavage of hydrogen in a molecule, a polymerization initiator having a triazine structure, and a polymerization initiator having an oxadiazole structure.

Such a material is the polymerization initiator having the acetophenone structure as 2-hydroxy-2-methyl-1-phenyl-propane-1-one, 1-hydroxycyclohexylphenyl ketone, 2,2-dimethoxy-1,2-diphenylethane-1-one, 2-methyl-1-[4-(methyl-

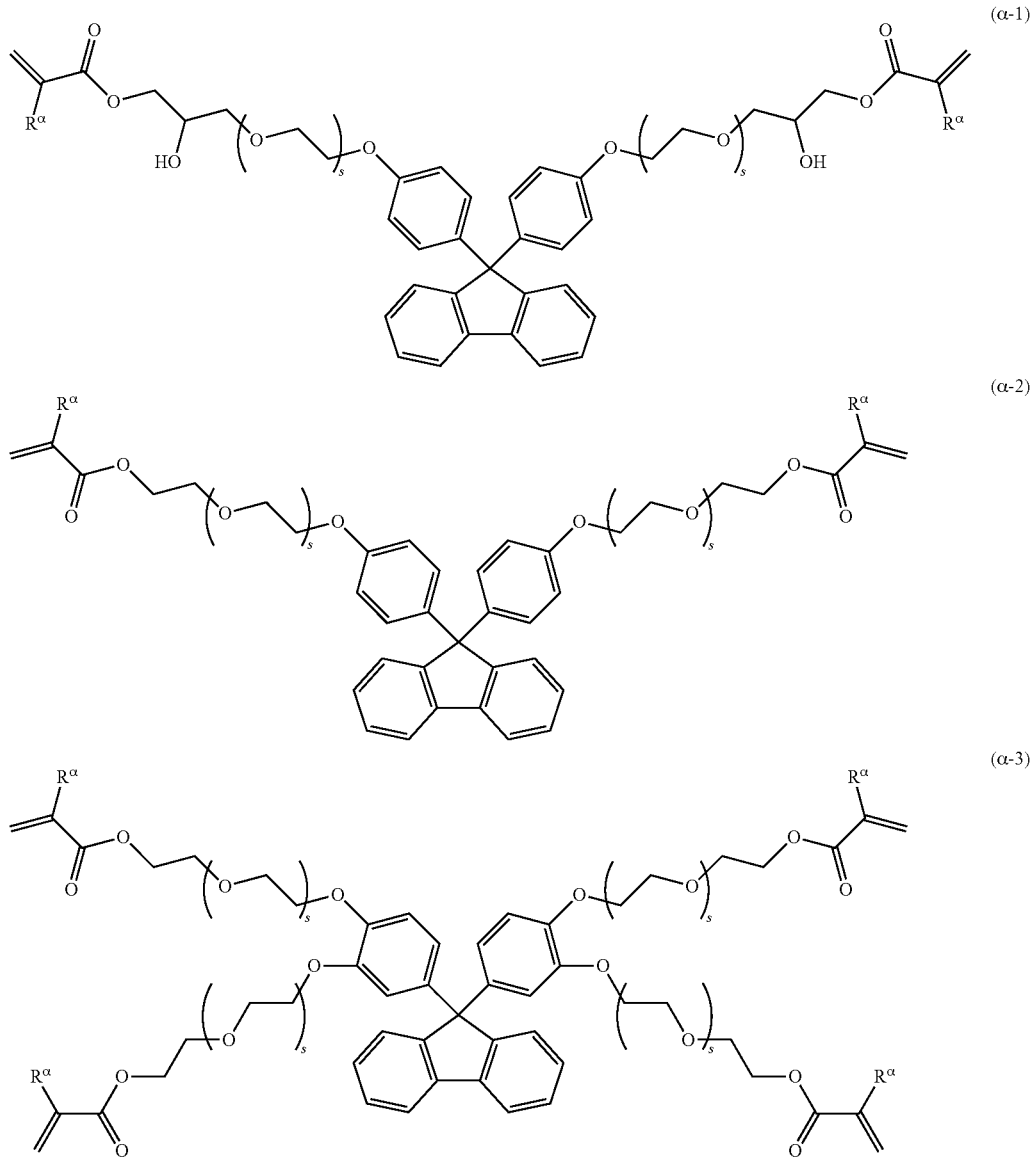

In formulas (α-1) to (α-3), $R^\alpha$ is independently hydrogen or methyl, and s is independently an integer from 0 to 4.

Addition of a polymerization initiator optimizes the rate of polymerization of the polymerizable liquid crystal composition. A photoradical initiator or the like is the polymerization initiator.

Such a material is the photoradical initiator as a polymerization initiator having an acetophenone structure, a polymerization initiator having an acylphosphine oxide structure, a polymerization initiator having an O-acyloxime ester structure, a polymerization initiator having a feature of thio)phenyl]-2-morpholinopropane-1-one, and 2-benzyl-2-dimethylamino-4'-morpholinobutyrophenone.

Such a material is the polymerization initiator having the acylphosphine oxide structure as bis(2,4,6-trimethylbenzoyl)-phenylphosphine oxide and 2,4,6-trimethylbenzoyl-diphenyl-phosphine oxide.

Such a material is the polymerization initiator having the O-acyloxime ester structure as 1-[4-(phenylthio)phenyl]-1,2-octanedione 2-(O-benzoyloxime), 1-[9-ethyl-6-(2-methyl-benzoyl)9H-carbazole-3-yl]ethanone 1-(O-acetyloxime)

and 1,2-propanedione, 1-[4-[[4-(2-hydroxyethoxy)phenyl]thio]phenyl]-,2-(O-acetyloxime).

Such a material is the polymerization initiator having the triazine structure as p-methoxyphenyl-2,4-bis(trichloromethyl)triazine.

Such a material is the polymerization initiator having the oxadiazole structure as 2-(p-butoxystyryl)-5-trichloromethyl-1,3,4-oxadiazole.

A total of weight in a content of the photoradical polymerization initiator in the polymerizable liquid crystal composition is preferably about 0.01 to about 20% by weight, and further preferably about 0.1 to about 10% by weight, based on the total amount of the polymerizable liquid crystal composition. The reason is that both of an improvement of uniformity of alignment in the liquid crystal polymerization film and the improvement of hardness of the liquid crystal polymerization film are satisfied.

A sensitizer may be added to the polymerizable liquid crystal composition together with the photoradical polymerization initiator. Such a material is the sensitizer as isopropyl thioxanthone, diethyl thioxanthone, ethyl-4-dimethylaminobenzoate and 2-ethylhexyl-4-dimethylaminobenzoate.

Addition of one kind or more kinds of chain transfer agents to the polymerizable liquid crystal composition causes control of a reaction rate and a chain length of the obtained liquid crystal polymerization film. An increase of amount of addition of the chain transfer agent causes reduction of a polymerization reaction rate and reduction of a polymer chain length. Such a material is the chain transfer agent as a thiol compound or styrene dimer.

The thiol-based chain transfer agent includes a monofunctional thiol derivative and a polyfunctional thiol derivative. Such a material is the monofunctional thiol derivative as dodecanethiol and 2-ethylhexyl 3-mercaptopropionate.

Such a material is the polyfunctional thiol as trimethylolpropane tris(3-mercaptopropionate), pentaerythritol tetrakis(3-mercaptopropionate), 1,4-bis(3-mercaptobutyryloxy)butane, pentaerythritol tetrakis(3-mercaptobutyrate) and 1,3,5-tris(3-mercaptobutyloxyethyl)-1,3,5-triazine-2,4,6(1H,3H,5H)-trione.

Such a material is a styrene dimer-based chain transfer agent as 4-diphenyl-4-methyl-1-pentene and 2,4-diphenyl-1-butene.

Addition of a polymerization inhibitor to the polymerizable liquid crystal composition causes prevention of polymerization initiation during storage of the polymerizable liquid crystal composition. A phenol derivative, a benzothiazine derivative, a phenothiazine derivative or a compound containing a nitroso group serves as the polymerization inhibitor.

Such a material is the phenol derivative as 2,5-di(t-butyl) hydroxytoluene, hydroquinone, o-hydroxybenzophenone and diphenylpicryl hydrazide.

Such a material is the benzothiazine derivative as 2H-1,3-benzothiazine-2,4-(3H)dione. Such a material is the phenothiazine derivative as phenothiazine and methylene blue. Such a material is the compound containing having the nitroso group being the polymerization inhibitor as N,N-dimethyl-4-nitrosoaniline.

Addition of the polymerization inhibitor to the polymerizable liquid crystal composition causes suppression of the polymerization reaction in the polymerizable liquid crystal composition by generation of radicals in the polymerizable liquid crystal composition. Addition of the polymerization inhibitor causes an improvement of storage stability of the polymerizable liquid crystal composition.

Specific examples of the polymerization inhibitor include (A) a phenol-based antioxidant, (B) a sulfur-based antioxidant, (C) a phosphoric acid-based antioxidant and (D) a hindered amine-based antioxidant. From viewpoints of compatibility with the polymerizable liquid crystal composition and transparency of the liquid crystal polymerization film-kind, a phenol-based antioxidant is preferred.

From a viewpoint of compatibility, as the phenol-based antioxidant, a compound having a t-butyl group in an ortho position of a hydroxy group is preferred.

An ultraviolet light absorber, a light stabilizer, an antioxidant and a silane coupling material may be added to the liquid crystal composition.

Addition of the ultraviolet light absorber to the polymerizable liquid crystal composition causes an improvement of weather resistance of the polymerizable liquid crystal composition. Addition of the light stabilizer to the polymerizable liquid crystal composition causes an improvement of weather resistance of the polymerizable liquid crystal composition. Addition of the antioxidant to the polymerizable liquid crystal composition causes an improvement of weather resistance of the polymerizable liquid crystal composition. Addition of the silane coupling agent to the polymerizable liquid crystal composition causes an improvement of adhesion between the substrate and the liquid crystal polymerization film.

In order to facilitate coating, a solvent is preferably added to the polymerizable liquid crystal composition.

Such a material may be a component of the solvent as ester, an amide-based compound, alcohol, ether, glycol monoalkyl ether, aromatic hydrocarbon, halogenated aromatic hydrocarbon, aliphatic hydrocarbon, halogenated aliphatic hydrocarbon, alicyclic hydrocarbon, ketone and acetate.

The amide-based compound means a compound having an amide group, and serving as the component of the solvent. The acetate-based solvent means a compound having an acetate structure, and serving as the component of the solvent.

Such a material is the ester as alkyl acetate, ethyl trifluoroacetate, alkyl propionate, alkyl butyrate, dialkyl malonate, alkyl glycolate, alkyl lactate, monoacetin, γ-butyrolactone and γ-valerolactone.

From a viewpoint of solubility, use of an amide-based solvent, an aromatic hydrocarbon-based solvent or a ketone-based solvent is preferred.

In consideration of a boiling point of the solvent, addition of an ester-based solvent, an alcohol-based solvent, an ether-based solvent or a glycolmonoalkyl ether-based solvent is preferred.

A case where the plastic substrate is used as the substrate requires reduction of a drying temperature in order to prevent deformation of the substrate, and avoidance of corrosion of the substrate by the solvent. In such a case, an aromatic hydrocarbon-based solvent, a ketone-based solvent, an ester-based solvent, an ether-based solvent, an alcohol-based solvent, an acetate-based solvent, a glycol monoalkylether-based solvent or the like is preferred.

From a viewpoint of compatibility with the polymerizable liquid crystal compound, a content of the solvent in the polymerizable liquid crystal composition is preferably about 30 to about 96% by weight, further preferably about 50 to about 90% by weight, and still further preferably about 50 to about 80% by weight, based on the total amount of the polymerizable liquid crystal composition.

The polymerizable liquid crystal composition of the invention may contain a compound having optical activity.

Addition of the compound having optical activity to the liquid crystal composition results in inducing twist alignment. The liquid crystal polymerization film-kind can be used as a selective reflection film and a negative C-plate in the wavelength region of about 300 to about 2,000 nanometers.

Such a material is the compound having optical activity as a compound having asymmetrical carbon, an axial chirality compound having a binaphtyl structure, a helicene structure or the like, and a plane chirality compound having a cyclophane structure or the like. From a viewpoint of immobilizing a helical pitch of twist alignment, the compound having optical activity in the above case is preferably a polymerizable compound.

The polymerizable liquid crystal composition of the invention may contain a dichroic dye. The liquid crystal polymerization film-kind in which a composite with the dichroic dye is formed can be used in the form of an absorptive polarizing plate.

The dichroic dye is preferably a material having a maximal absorption wavelength in the range of about 300 to about 700 nanometers. An acridine dye, an oxazine dye, a cyanine dye, naphthalene dye, an azo dye, an anthraquinone pigment or the like can be utilized. As the azo dye, such a material is the dichroic dye as a monoazo dye, a bisazo dye, a trisazo dye, a tetrakisazo dye or a stilbeneazo dye.

The polymerizable liquid crystal composition of the invention may contain a fluorescent dye. The liquid crystal polymerization film-kind in which a composite with the fluorescent dye is formed can be used in the form of a polarizing light-emitting film and a wavelength conversion film.

Production of Substrate-Embedded Liquid Crystal Polymerization Film

A substrate-embedded liquid crystal polymerization film according to the invention is obtained through steps described below.

(1) A polymerizable liquid crystal composition is coated onto a substrate, and when necessary, the resulting material is dried to form a coating film.

(2) The polymerizable liquid crystal composition is polymerized by means such as light, heat or a catalyst to obtain a substrate-embedded liquid crystal polymerization film.

Thus, the polymerizable liquid crystal composition in the coating film is immobilized while the liquid crystal state is kept.

Replacement of Substrate in Substrate-Embedded Liquid Crystal Polymerization Film As a method of replacing the substrate of the substrate-embedded liquid crystal polymerization film, methods described below are known.

(1) The substrate-embedded liquid crystal polymerization film and the substrate having an adhesive layer are laminated in such a manner that the liquid crystal polymerization film in the substrate-embedded liquid crystal polymerization film is brought into contact with the adhesive layer, and (2) the laminated material in such a manner that the liquid crystal polymerization film is brought into contact with the adhesive layer is peeled off between a substrate part of the substrate-embedded liquid crystal polymerization film, and the liquid crystal polymerization film of the substrate-embedded liquid crystal polymerization film.

For coating of the polymerizable liquid crystal composition onto the substrate, various coating methods are applied. From a viewpoint of uniformity of the film thickness of the polymerizable liquid crystal composition on the substrate, a spin coating method, a microgravure coating method, a gravure coating method, a wire-bar coating method, a dip coating method, a spray coating method, a meniscus coating method and a die coating method are preferred.

In order to form the substrate-embedded liquid crystal polymerization film, during drying, heat treatment is preferred. A hot plate, a drying oven, blowing warm air or hot air, and the like are available for the heat treatment.

A temperature of the heat treatment is from room temperature to about 120° C. For further improving alignment uniformity, the heat treatment in the range of temperature from about NI point minus 15° C. to about NI point is preferred, wherein NI point is of the polymerizable liquid crystal composition. A period of heat treatment is from about 20 seconds to about 30 minutes. The number of times of heat treatment is able to be one or more.

In process from the polymerizable liquid crystal composition to the liquid crystal polymerization film, a means such as an electron beam, ultraviolet light, visible light and infrared light can be utilized. The range of wavelength of the light to be irradiated in order to obtain the liquid crystal polymerization film is from about 150 to about 500 nanometers. The preferred range of the wavelength of the light is from about 250 to about 450 nanometers, and The further preferred range is from about 300 to about 400 nanometers.

As a light source of the light, a low pressure mercury lamp, a high-pressure discharge lamp, a short arc discharge lamp and the like are available. A bactericidal lamp, a fluorescent chemical lamp a black light and the like are the low pressure mercury lamps. A high pressure mercury lamp, a metal halide lamp and the like are the high-pressure discharges lamps. An ultra-high pressure mercury lamp, a Xenon lamp a Mercury-Xenon lamp and the like are the short arc discharge lamps.

A thickness of the liquid crystal polymerization film is depended on required retardation. A typical thickness of the liquid crystal polymerization film is from about 0.1 to about 50 m. From a viewpoint of thinning the display device, thickness about 0.5 to about 10 micrometers of the liquid crystal polymerization film is preferred.

A polarizing plate having a function such as optical compensation can be produced by using the polarizing plate as the substrate and forming the liquid crystal polymerization film on the substrate. For example, a circular polarizing plate can be produced by combining the liquid crystal polymerization film having retardation of a ¼ wavelength plate with the polarizing plate.

Specific examples of the polarizing plate include an absorptive polarizing plate doped by iodine or a dichroic dye, and a reflective polarizing plate such as a wire grid polarizing plate.

In an organic electroluminescence display, for the purpose of preventing outside light reflection, the circular polarizing plate made of the ¼ wavelength plate and of the polarizing plate is used on the viewing side. In order to induce an antireflection function relative to a total wavelength in a visible region effectively, control of the chromatic dispersion characteristics of the ¼ wavelength plate is required.

When using the liquid crystal polymerization film-kind as a phase difference plate for the ¼ wavelength plate, a ½ wavelength plate or the like, having $Re_{450}/Re_{550} \leq 1.05$ is preferred because uneven color and visibility such as viewing angle characteristics are improved. Moreover, Moreover, for improving blue viewing angle characteristics when setting green to optimum retardation, chromatic dispersion characteristics $0.75 \leq Re_{450}/Re_{550} \leq 1.05$ of the liquid crystal polymerization film-kind is further preferred.

Moreover, for improving red viewing angle characteristics when setting green to the optimum retardation, the characteristics $0.97 \leq Re_{650}/Re_{550} \leq 1.24$ is preferred.

For the reasons described above, in the view of the chromatic dispersion characteristics, the smaller value of $Re_{450}/Re_{550}$ of the liquid crystal polymerization film-kind, and the larger value of $Re_{650}/Re_{550}$ is preferred.

Compound (1) can provide the polymerizable liquid crystal compound serving as the raw material of the liquid crystal polymerization film-kind having an advantage of ease of handling owing to high compatibility with the organic solvent, the liquid crystal composition serving as the raw material of the liquid crystal polymerization film-kind, the device having the liquid crystal polymerization film-kind, and the method of producing the device.

Compound (1) can provide the polymerizable liquid crystal compound serving as the raw material of the liquid crystal polymerization film-kind having the advantage of ease of handling owing to a long period of time of holding the liquid crystal phase under room temperature, the liquid crystal composition serving as the raw material of the liquid crystal polymerization film-kind, the device including the liquid crystal polymerization film-kind, and the method of producing the device.

The liquid crystal polymerization film-kind having low chromatic dispersion characteristics can be easily obtained by using the polymerizable liquid crystal compound and the polymerizable liquid crystal composition containing the compound according to the invention. Accordingly, in the obtained liquid crystal polymerization film-kind, uniform polarization conversion can be achieved in a wide wavelength band. For example, the liquid crystal polymerization film-kind of the invention are preferred for a film formed of an optically anisotropic film or a display device having a device, such as a phase difference film, an optical compensation film, a reflection film, a selective reflection film, an antireflection film, a viewing angle compensation film, a liquid crystal alignment film, a polarizing device, a circularly polarizing device and an elliptically polarizing device.

EXAMPLES

The invention is not limited only to Examples.

In Examples of the invention, "DCC" means 1,3-dicyclohexylcarbodiimide.

In Examples of the invention, "DMAP" means 4-dimethylaminopyridine.

In Examples of the invention, "IPA" means 2-propanol.

In Examples of the invention, "pTSA" means p-toluenesulfonic acid.

In Examples of the invention, "THF" means tetrahydrofuran.

In Examples of the invention, "Irg-907" means Irgacure (trademark) 907 made by BASF Japan Ltd.

In Examples of the invention, "FTX-218" means Futargent (trademark) FTX-218 made by Neos Co., Ltd.

In Examples of the invention, "NCI-930" means ADEKA cruise (trademark) NCI-930 made by ADEKA Corporation.

In Examples of the invention, "PF No. 75" means Polyflow (trademark) No. 75 of Kyoeisha Chemical Co., Ltd.

In Examples of the invention, "PIA-5370" means Lixon Aligner PIA-5370 made by JNC Corporation.

In Examples of the invention, "TF370" means TEGO-Flow (trademark) 370 of Evonik Japan, Inc.

Confirmation of Structure of Compound

A structure of a compound was confirmed by 500 MHz proton NMR measurement. Measurement was performed by dissolving, into $CDCl_3$, a compound to be measured. A position of a peak measured was expressed excluding a unit of ppm, and s, d, t and m stand for a singlet, a doublet a triplet and a multiplet, respectively. For proton NMR measurement, DRX-500 made by Bruker Corporation was used.

Phase Transition Temperature sample were placed on a hot plate in a melting point apparatus equipped with a polarizing microscope, and a temperature at transition of phases of the sample occurred was measured while the sample was heated at a rate of 3° C. per minute. Some of sample were placed on a hot plate in a melting point apparatus equipped with a polarizing microscope, and temperatures at which transition of phases of samples to another phase occurred was measured while samples were cooled at 3° C. per minute.

Polymerization Conditions for Polymerizable Liquid Crystal Composition

Under a nitrogen atmosphere, a sample was irradiated by light at room temperature by using an ultra-high pressure mercury lamp to polymerize a polymerizable liquid crystal composition. The ultra-high pressure mercury lamp was Multilight-250 made by Ushio Inc.

An amount of light irradiation was adjusted to be 500 $mJ/cm^2$ on the surface to be irradiated.

Intensity of the light irradiation was measured by using UIT-150-A being an ultraviolet intensity meter made by Ushio Inc. and UVD-S365 being a photodetector made by Ushio Inc.

Evaluation of Alignment (1) Preparation of Glass Substrate with an Alignment Film Subjected to Rubbing Treatment A glass substrate with an alignment film subjected to rubbing treatment was prepared according to the following procedures:

(i) a coating film was prepared on a glass substrate by spin coating PIA-5370;

(ii) a solvent was removed therefrom by placing the glass substrate on a hot plate at 80° C.;

(iii) the glass substrate was calcined in an oven at 230° C. for 30 minutes; and (iv) the coating film on the glass substrate was subjected to rubbing treatment by wiping the coating film in one direction by using a rayon cloth.

(2) Visual Observation Method

Observation was made by interposing, between two polarizing plates arranged in a crossed Nicol state, a substrate-embedded liquid crystal polymerization film, and rotating the substrate in a horizontal plane to confirm a light and dark state. The substrate-embedded liquid crystal polymerization film was observed by a polarizing microscope to confirm existence or non-existence of alignment defects.

(3) Measurement by Ellipsometer

Retardation of the substrate-embedded liquid crystal polymerization film was measured by using OPTIPRO Ellipsometer made by Shintech, Inc. The measurement was performed by irradiating a film surface of the substrate-embedded liquid crystal polymerization film with light having wavelengths of 450 nm, 550 nm and 650 nm. The retardation was measured while an incident angle of the irradiation light on the film surface was increased by 5 degrees from −50 degrees to 50 degrees.

Measurement of Film Thickness

A film thickness of the liquid crystal polymerization film was measured according to the following procedures:

(1) a layer of a liquid crystal polymerization film was shaved off from the liquid crystal film with the substrate, and (2) a depth of level difference caused by shaving off described above was measured by using a High-Resolution Surface Profiler.

Here, the High-Resolution Surface Profiler is Alpha-Step IQ made by KLA-Tencor Corporation.

Calculation of Δn(550)

Then, Δn(550) was calculated by: dividing $Re_{550}$ of a substrate-embedded liquid crystal polymerization film having homogeneous alignment, by a film thickness.

Example 1

Compound (1-1-1-1) was prepared according to procedures described below.

Then, 1,2-diamino-3,6-dimethoxybenzene was prepared according to Org. Lett. 13, 10, 2642 (2011).

To 58 mL of ethanol, 5.8 g of 1,2-diamino-3,6-dimethoxybenzene and 4.6 g of phenylglyoxal were added, and the resulting mixture was stirred at room temperature under a nitrogen atmosphere, and 0.7 g of aminosulfuric acid was added thereto little by little. Then, the resulting mixture was stirred at room temperature for 8 hours. Water and ethyl acetate were further added thereto, an organic layer was extracted, washed with water, and dried over anhydrous magnesium sulfate. A solvent was distilled off under reduced

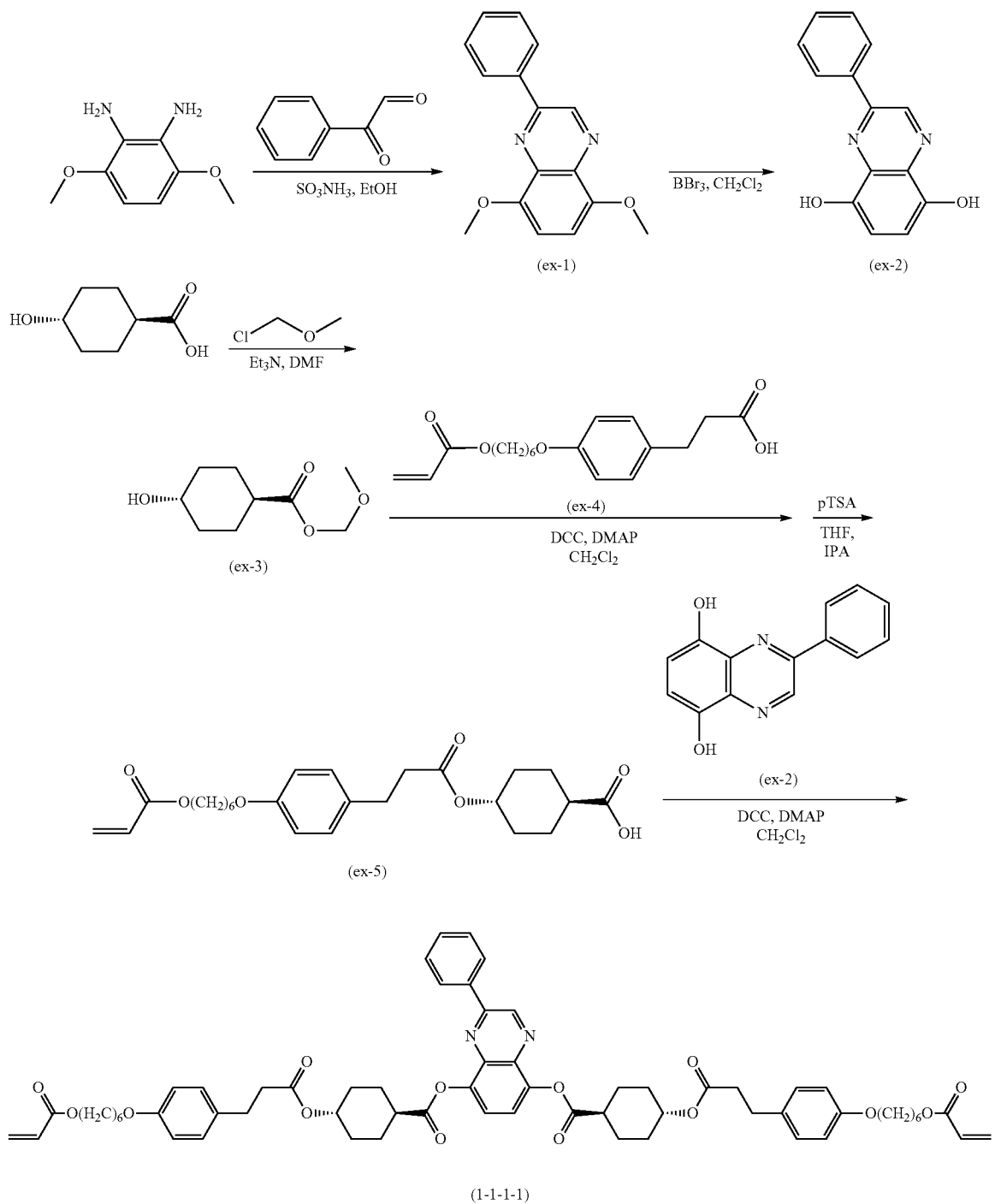

pressure, and the resulting residue was recrystallized in a mixed solution of toluene/heptane to obtain 9.2 g of compound (ex-1), in which a volume ratio of the mixed solution of toluene/heptane was 15:1.

To 80 mL of dichloromethane, 7.9 g of compound (ex-1) was added, and the resulting mixture was stirred while being cooled at −60° C. or lower under a nitrogen atmosphere. Then, 16.4 g of BBr$_3$ was added dropwise thereto. After dropwise addition, the resulting mixture was stirred at −60° C. or lower for 1 hour, and then stirred at room temperature for 16 hours. The reaction mixture was poured into ice water and quenched, ethyl acetate was further added thereto, and an organic layer was extracted. The organic layer was washed with saturated aqueous solution of sodium hydrogencarbonate, and further washed with water. The resulting organic layer was dried over magnesium sulfate, then the solvent was distilled off under reduced pressure, and the resulting residue was dried under reduced pressure to obtain 3.3 g of compound (ex-2).

To 125 mL of dimethylformamide, 25.0 g of trans-4-hydroxycyclohexanecarboxylic acid and 26.3 g of triethylamine were added, and the resulting mixture was stirred while being cooled at 10° C. or lower under a nitrogen atmosphere. Then, 14.7 g of chloromethyl methyl ether was slowly added dropwise thereto. After dropwise addition, the resulting mixture was stirred at room temperature for 8 hours. Then, ethyl acetate and water were further added thereto, an organic layer was extracted, and the organic layer was washed with saturated aqueous solution of sodium hydrogencarbonate and water and dried over anhydrous magnesium sulfate. Ethyl acetate was distilled off under reduced pressure, and the resulting residue was purified by column chromatography and dried under reduced pressure to obtain 25.2 g of compound (ex-3), in which a column of column chromatography was a silica gel, and an eluent of the column chromatography was a mixture of toluene and ethyl acetate having a volume ratio of 2:1.

Compound (ex-4) was prepared by a method similar to the method in Example 1 in JP 2008-239873 A.

25.2 g of compound (ex-3), 42.9 g of compound (ex-4) and 3.3 g of DMAP were added to 430 mL of dichloromethane, and the resulting mixture was stirred while being cooled at 5° C. under a nitrogen atmosphere in an ice bath. Then, 60 mL of a dichloromethane solution of 29.0 g of 1,3-dicyclohexylcarbodiimide was added dropwise thereto. After dropwise addition, the resulting mixture was stirred at room temperature for 16 hours. After the precipitated deposits were filtered off, an organic layer was washed with a saturated aqueous solution of sodium hydrogencarbonate, washed with water, and dried over anhydrous magnesium sulfate. Dichloromethane was distilled off under reduced pressure, and the resulting residue was purified by column chromatography and dried under reduced pressure, in which a column of column chromatography was a silica gel, and an eluent of the column chromatography was a mixture of toluene and ethyl acetate having a volume ratio of 4:1.

To a mixed solution of 110 mL of THF and 55 mL of IPA, the obtained residue and 2.1 g of pTSA were added, and the resulting mixture was stirred at 40° C. for 8 hours. Then, ethyl acetate and water were further added thereto, an organic layer was extracted, and the organic layer was washed with saturated brine, and dried over anhydrous magnesium sulfate. A solvent was distilled off under reduced pressure, and the resulting residue was recrystallized in a mixed solution of ethyl acetate and heptane at 15:1 in a volume ratio to obtain 31.8 g of compound (ex-5).

To 50 mL of dichloromethane, 1.3 g of compound (ex-2), 5.0 g of compound (ex-5) and 0.3 g of DMAP were added, and the resulting mixture was stirred while being cooled at 5° C. under a nitrogen atmosphere in an ice bath. Then, 5 mL of a dichloromethane solution in which 2.4 g of DCC was dissolved was added dropwise thereto. After dropwise addition, the resulting mixture was stirred at room temperature for 16 hours. The precipitated deposits were filtered off, an organic layer was washed with water, and dried over anhydrous magnesium sulfate. Dichloromethane was distilled off under reduced pressure, and the resulting residue was purified by column chromatography, and recrystallized in methanol to obtain 3.8 g of compound (1-1-1-1), in which a column of column chromatography was a silica gel, and an eluent of the column chromatography was a mixture of toluene and ethyl acetate at 8:1 in a volume ratio.

When compound (1-1-1-1) was heated, It transited from a crystal phase to an isotropic liquid at 104° C. When compound (1-1-1-1) was cooled, It transited from the isotropic liquid to the nematic phase at 94° C.

Signals of proton NMR of compound (1-1-1-1) were as described below.

9.29 (s, 1H), 8.09 (d, 2H), 7.58-7.52 (m, 3H), 7.46 (d, 1H), 7.41 (d, 1H), 7.12 (d, 4H), 6.82 (d, 4H), 6.40 (d, 2H), 6.16-6.08 (m, 2H), 5.81 (d, 2H), 4.87-4.79 (m, 2H), 4.17 (t, 4H), 3.94 (t, 4H), 2.91 (t, 4H), 2.85-2.76 (m, 2H), 2.61 (t, 4H), 2.38-2.29 (m, 4H), 2.17-2.09 (m, 4H), 1.94-1.67 (m, 12H), 1.56-1.41 (m, 12H).

Example 2

Compound (1-1-2-1) was prepared by changing phenylglyoxal to 1-phenyl-1,3-propanedione in the procedures described in Example 1.

(1-1-2-1)

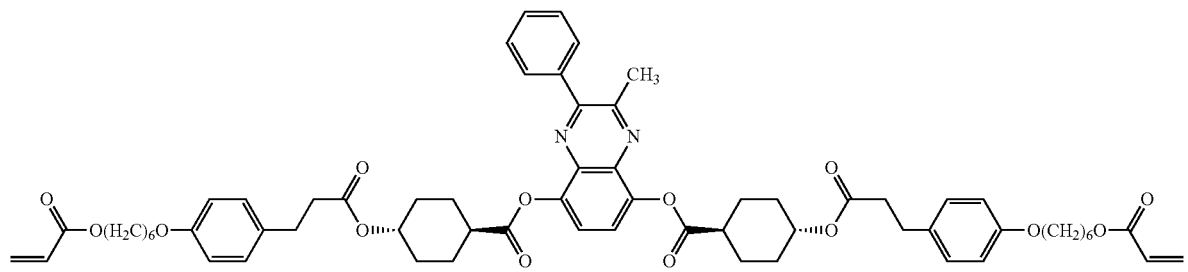

When compound (1-1-2-1) was heated, It transited from a crystal phase to a nematic phase at 71° C. When compound (1-1-2-1) was cooled, It transited from the nematic phase to an isotropic liquid at 89° C.

Signals of proton NMR of compound (1-1-2-1) were as described below.

7.64-7.59 (m, 2H), 7.53-7.48 (m, 3H), 7.40-7.35 (m, 2H), 7.11 (t, 4H), 6.85-6.79 (m, 4H), 6.40 (d, 2H), 6.16-6.08 (m, 2H), 5.81 (d, 2H), 4.88-4.82 (m, 1H), 4.77-4.69 (m, 1H), 4.17 (t, 4H), 3.93 (t, 4H), 2.93-2.86 (m, 4H), 2.83-2.67 (m, 5H), 2.63-2.55 (m, 4H), 2.35-2.29 (m, 2H), 2.24-2.10 (m, 4H), 2.07-2.00 (m, 2H), 1.94-1.67 (m, 10H), 1.57-1.37 (m, 12H).

Example 3

Compound (1-5-1-1) was prepared by changing phenylglyoxal to 1-phenyl-1,3-propanedione in the procedures described in Example 1.

(1-5-1-1)

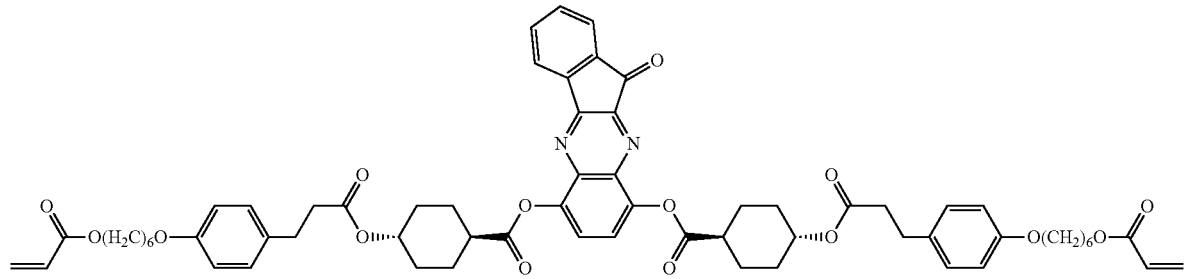

When compound (1-5-1-1) was heated, It transited from a crystal phase to a smectic phase at 89° C., from the smectic phase to a nematic phase at 137° C., and from the nematic phase to an isotropic liquid at 146° C.

Signals of proton NMR of compound (1-5-1-1) were as described below.

7.96 to 7.90 (m, 2H), 7.79 (t, 1H), 7.64 (m, 1H), 7.49 (d, 1H), 7.41 (d, 2H), 7.13 (d, 4H), 6.83 (d, 4H), 6.40 (d, 2H), 6.16-6.08 (m, 2H), 5.81 (d, 2H), 4.91-4.84 (m, 2H), 4.17 (t, 4H), 3.94 (t, 4H), 2.95-2.89 (m, 4H), 2.87-2.78 (m, 2H), 2.66-2.59 (m, 4H), 2.41-2.29 (m, 4H), 2.22-2.12 (m, 4H), 1.97-1.68 (m, 12H), 1.60-1.41 (m, 12H).

Example 4

Compound (1-2-1-1) was prepared according to procedures described below.

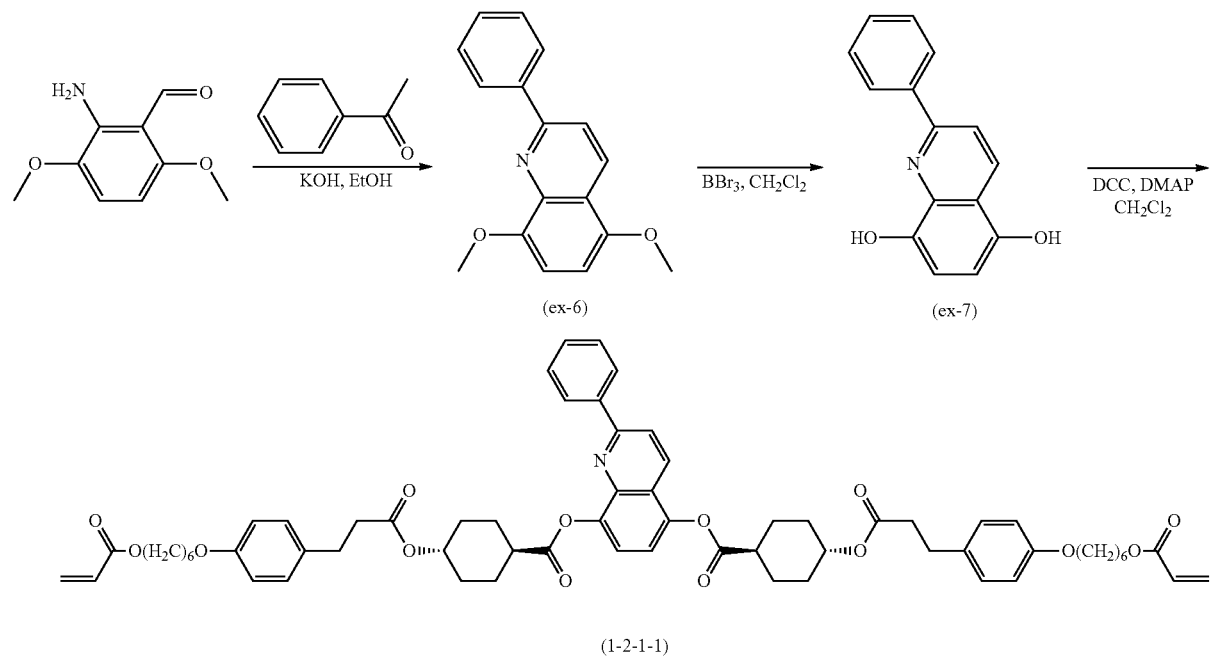

(1-2-1-1)

Then, 2-amino-3,6-dimethoxybenzaldehyde was prepared according to Heterocyclic communications. 8, 2, 135 (2002) and J. Org. Chem. 58, 7, 1666 (1993).

To 50 mL of ethanol, 5.0 g of 2-amino-3,6-dimethoxybenzaldehyde, 3.3 g of acetophenone and 1.7 g of potassium hydroxide were added, and the resulting mixture was refluxed while being stirred for 8 hours under a nitrogen atmosphere. After the resulting mixture was left to cool, water and ethyl acetate were further added thereto, an organic layer was extracted, and the organic layer was washed with water, and dried over anhydrous magnesium sulfate. A solvent was distilled off under reduced pressure, and the resulting residue was dried under reduced pressure to obtain 5.8 g of compound (ex-6).

To 80 mL of dichloromethane, 7.9 g of compound (ex-6) was added, and the resulting mixture was stirred while being cooled at −60° C. or lower in a dry ice bath under a nitrogen atmosphere. Then, 16.4 g of BBr₃ was added dropwise thereto. After dropwise addition, the resulting mixture was stirred at −60° C. or lower for 1 hour, and stirred at room temperature for 16 hours. The reaction mixture was poured into ice water and quenched, ethyl acetate was further added thereto, and an organic layer was extracted. The organic layer was washed with a saturated aqueous solution of sodium hydrogencarbonate, and then further washed with water. The resulting organic layer was dried over anhydrous magnesium sulfate, and a solvent was distilled off under reduced pressure, and the resulting residue was dried under reduced pressure to obtain 3.3 g of compound (ex-7).

To 50 mL of dichloromethane, 1.3 g of compound (ex-7), 5.0 g of compound (ex-5) and 0.3 g of DMAP were added, and the resulting mixture was stirred while being cooled at 5° C. under a nitrogen atmosphere in an ice bath. Then, 5 mL of a dichloromethane solution in which 2.4 g of DCC was dissolved was added dropwise thereto. After dropwise addition, the resulting mixture was stirred at room temperature for 16 hours.

The precipitated deposits were filtered off, an organic layer was washed with water, and dried over anhydrous magnesium sulfate. Dichloromethane was distilled off under reduced pressure, and the resulting residue was purified by column chromatography, and recrystallized in methanol to obtain 3.3 g of compound (1-2-1-1), in which a column of column chromatography was a silica gel, and an eluent of the column chromatography was a mixture of toluene and ethyl acetate at 8:1 in a volume ratio.

When compound (1-2-1-1) was heated, transition was caused from a crystal phase to a nematic phase at 107° C., and from the nematic phase to an isotropic liquid at 111° C.

Signals of proton NMR of compound (1-2-1-1) were as described below.

8.19 (d, 1H), 8.06 (d, 2H), 7.91 (d, 1H), 7.55-7.45 (m, 3H), 7.40 (d, 1H), 7.26 (d, 1H), 7.12 (d, 4H), 6.82 (d, 4H), 6.40 (d, 2H), 6.16-6.08 (m, 2H), 5.81 (d, 2H), 4.87-4.77 (m, 2H), 4.19-4.14 (m, 4H), 3.94 (t, 4H), 2.91 (t, 4H), 2.85-2.70 (m, 2H), 2.61 (t, 4H), 2.40-2.28 (m, 4H), 2.17-2.09 (m, 4H), 1.95-1.67 (m, 12H), 1.56-1.41 (m, 12H).

Example 5

Compound (1-2-4-1) was prepared by changing acetophenone to 2-acetylthiophene in the procedures described in Example 3.

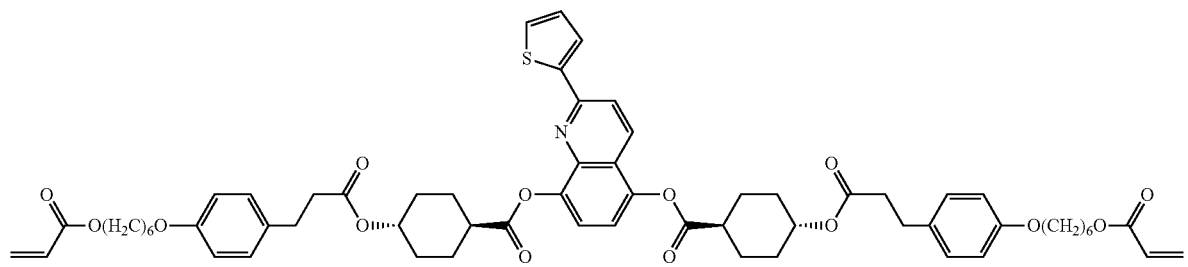

(1-2-4-1)

When compound (1-2-4-1) was heated, transition was caused from a crystal phase to a smectic phase at 84° C., and from the nematic phase to an isotropic liquid at 115° C.

Signals of proton NMR of compound (1-2-4-1) were as described below.

8.10 (d, 1H), 7.82 (d, 2H), 7.68 (d, 1H), 7.49 (d, 1H), 7.36 (d, 1H), 7.18 (d, 1H), 7.16-7.10 (m, 5H), 6.86-6.81 (m, 4H), 6.39 (d, 2H), 6.16-6.08 (m, 2H), 5.81 (d, 2H), 4.87-4.77 (m, 2H), 4.17 (t, 4H), 3.94 (t, 4H), 2.94-2.87 (m, 4H), 2.85-2.79 (m, 1H), 2.75-2.68 (m, 1H), 2.64-2.58 (m, 4H), 2.47-2.40 (m, 2H), 2.34-2.27 (m, 2H), 2.18-2.09 (m, 4H), 1.97-1.66 (m, 12H), 1.58-1.42 (m, 12H).

Example 6

Compound (1-2-5-1) was prepared by changing acetophenone to 2-acetyl benzothiophene in the procedures described in Example 3.

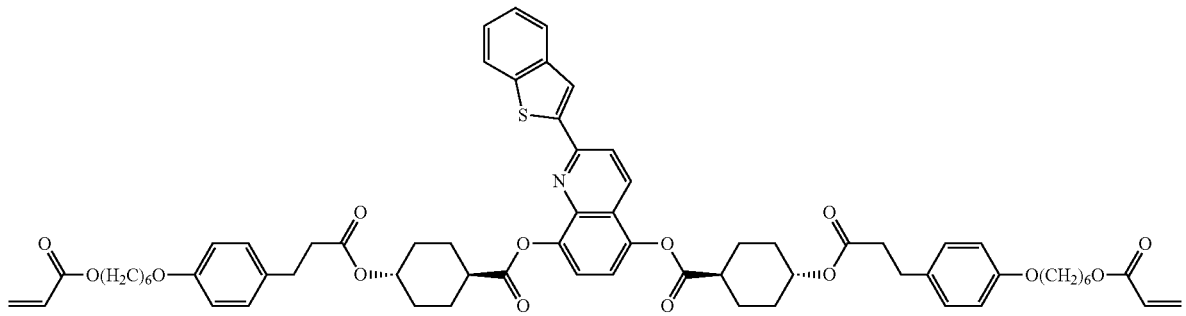

(1-2-5-1)

When compound (1-2-5-1) was heated, transition was caused from a crystal phase to a nematic phase at 108° C., and from the nematic phase to an isotropic liquid at 125° C.

Signals of proton NMR of compound (1-2-5-1) were as described below.

8.15 (d, 1H), 7.97 (d, 1H), 7.93 (s, 1H), 7.92 to 7.89 (m, 1H), 7.85 to 7.82 (m, 1H), 7.42 to 7.36 (m, 3H), 7.28 to 7.24 (m, 2H), 7.17 to 7.10 (m, 4H), 6.87 to 6.81 (m, 4H), 6.40 (d, 2H), 6.16 to 6.09 (m, 2H), 5.82 (d, 2H), 4.95 to 4.87 (m, 1H), 4.85 to 4.78 (m, 1H), 4.19 to 4.14 (m, 4H), 3.94 (t, 4H), 2.96 to 2.87 (m, 5H), 2.77 to 2.69 (m, 1H), 2.66 to 2.59 (m, 4H), 2.51 to 2.45 (m, 4H), 2.34 to 2.27 (m, 2H), 2.23 to 2.10 (m, 4H), 2.03 to 1.93 (m, 2H), 1.87 to 1.67 (m, 10H), 1.63 to 1.42 (m, 12H).

Example 7

Compound (1-1-10-1) was prepared by changing phenylglyoxal to 1,2-di-2-thienyl-1,2-ethanedione in the procedures described in Example 1.

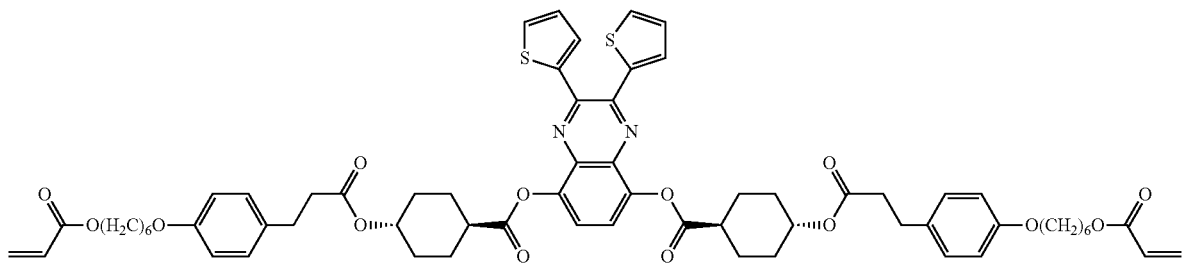

(1-1-10-1)

When compound (1-1-10-1) was heated, transition was caused from a crystal phase to an isotropic liquid at 139° C. Then, compound (1-1-10-1) was cooled, and transition was caused from the isotropic liquid to a nematic phase at 121° C.

Signals of proton NMR of compound (1-1-10-1) were as described below.

7.51 (d, 2H), 7.35 (s, 2H), 7.30 (d, 2H), 7.12 (d, 4H), 7.02-6.99 (m, 2H), 6.83 (d, 4H), 6.40 (d, 2H), 6.15-6.09 (m, 2H), 5.81 (d, 2H), 4.86-4.78 (m, 2H), 4.17 (t, 4H), 3.94 (t, 4H), 2.91 (t, 4H), 2.81-2.73 (m, 2H), 2.60 (t, 4H), 2.38-2.31 (m, 2H), 2.16-2.09 (m, 4H), 1.92-1.68 (m, 12H), 1.56-1.42 (m, 12H).

Example 8

Compound (1-1-12-1) was prepared by changing phenylglyoxal to 2,3-pentanedione in the procedures described in Example 1.

(1-1-12-1)
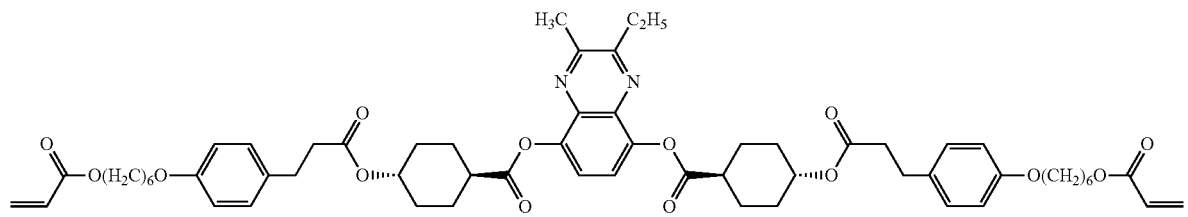
When compound (1-1-12-1) was heated, transition was caused from a crystal phase to a nematic phase at 80° C., and from the nematic phase to an isotropic liquid at 138° C.
Signals of proton NMR of compound (1-1-12-1) were as described below.
7.31 (s, 2H), 7.12 (d, 4H), 6.82 (d, 4H), 6.40 (d, 2H), 6.15-6.09 (m, 2H), 5.81 (d, 2H), 4.87-4.78 (m, 2H), 4.17 (t, 4H), 3.94 (t, 4H), 2.91 (t, 4H), 2.81-2.73 (m, 2H), 2.99-2.94 (m, 2H), 2.90 (t, 4H), 2.80-2.70 (m, 2H), 2.67 (s, 3H), 2.60 (t, 4H), 2.34-2.26 (m, 4H), 2.16-2.08 (m, 4H), 1.90-1.67 (m, 12H), 1.56-1.42 (m, 12H), 1.35 (t, 3H).
Example 9
Compound (1-6-1-1) was prepared according to procedures described below.
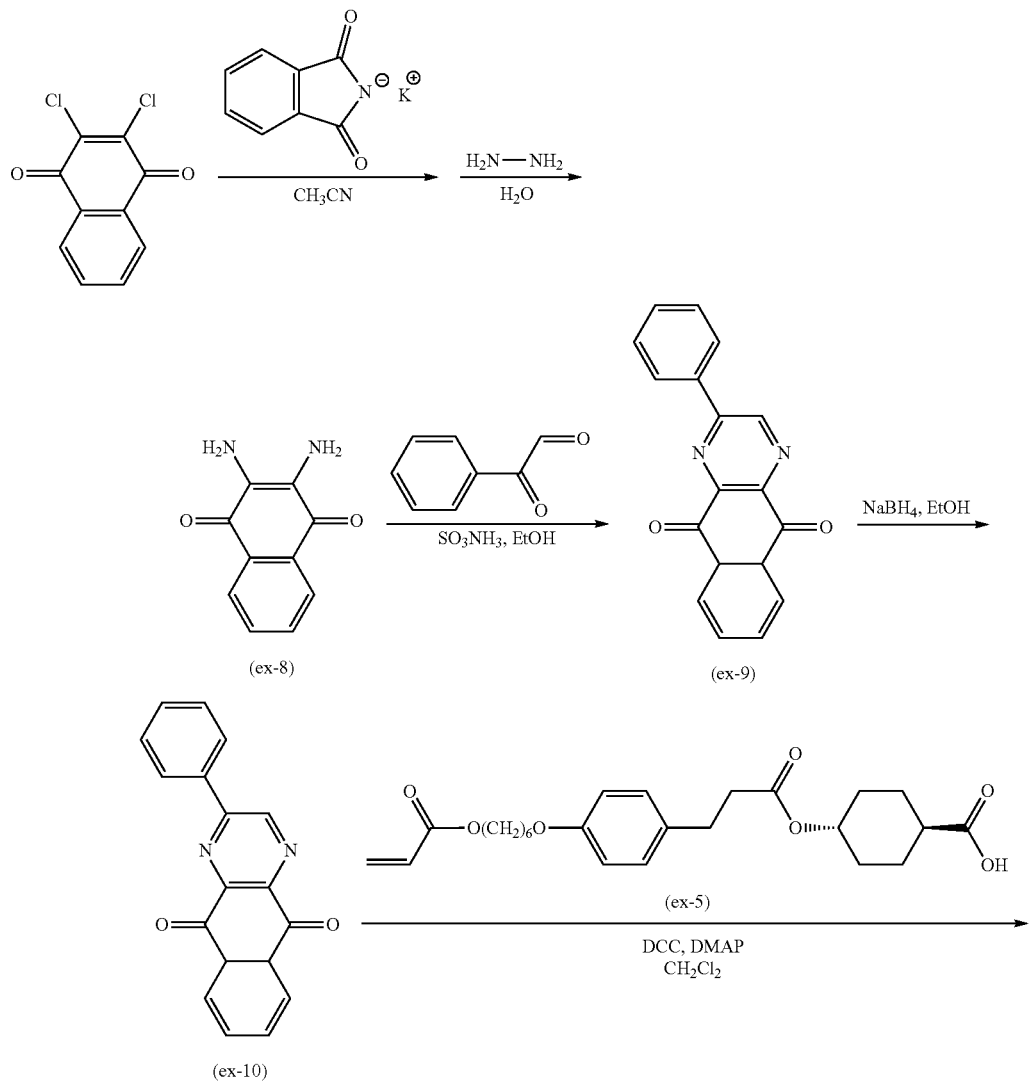

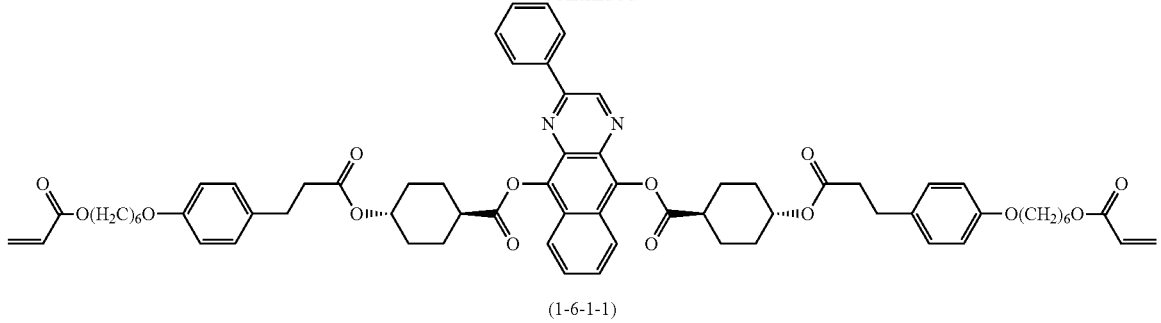

(1-6-1-1)

Compound (ex-8) was prepared according to Journal of Organometallic Chemistry, 750. (2014) pp. 98-106.

To 10 mL of methanol, 1.0 g of compound (ex-8) and 0.8 g of phenylglyoxal were added, and the resulting mixture was stirred at room temperature under a nitrogen atmosphere, and then 0.1 g of aminosulfuric acid was added thereto. Then, the resulting mixture was stirred at room temperature for 8 hours. Then, water was added to the reaction mixture, and deposits were filtered off. The obtained crystals were washed with water to obtain 1.5 g of compound (ex-9).

To 14 mL of ethanol, 1.4 g of compound (ex-9) was added, and the resulting mixture was cooled to 5° C. in an ice bath, and stirred under a nitrogen atmosphere. Then, 0.4 g of sodium borohydride was added thereto. Then, the resulting mixture was stirred at 5° C. for 3 hours. Then, a 1 N hydrochloric acid aqueous solution was slowly added dropwise until the mixture indicated acidity. Deposits were filtered off, and the obtained crystals were well washed with water to obtain 1.2 g of compound (ex-10)

To 35 mL of dichloromethane, 1.2 g of compound (ex-10), 3.8 g of compound (ex-5) and 0.2 g of DMAP were added, and the resulting mixture was cooled to 5° C. in an ice bath, and stirred under a nitrogen atmosphere. Then, 5 mL of a dichloromethane solution in which 1.9 g of DCC was dissolved was added dropwise. After dropwise addition, the resulting mixture was stirred at room temperature for 16 hours.

Deposits were filtered off, and water was added to the filtrate, and an organic layer was extracted, and dried over anhydrous magnesium sulfate. Dichloromethane was distilled off under reduced pressure, and the resulting residue was purified by column chromatography, and recrystallized in methanol to obtain 2.4 g of compound (1-6-1-1), in which a column of column chromatography was a silica gel, and an eluent of the column chromatography was a mixture of toluene and ethyl acetate at 8:1 in a volume ratio.

When compound (1-6-1-1) was heated, transition was caused from a crystal phase to an isotropic liquid at 122° C.

Signals of proton NMR of compound (1-6-1-1) were as described below.

9.33 (s, 1H), 8.18-8.10 (m, 4H), 7.65-7.55 (m, 5H), 7.13 (d, 4H), 6.83 (d, 4H), 6.40 (d, 2H), 6.16-6.08 (m, 2H), 5.81 (d, 2H), 4.92-4.85 (m, 2H), 4.17 (t, 4H), 3.94 (t, 4H), 3.04-2.96 (m, 2H), 2.92 (t, 4H), 2.62 (t, 4H), 2.52-2.43 (m, 4H), 2.24-2.17 (m, 4H), 2.07-1.94 (m, 4H), 1.83-1.67 (m, 12H), 1.63-1.42 (m, 12H).

Comparative Example 1

Compound (C-1) was prepared according to procedures described below.

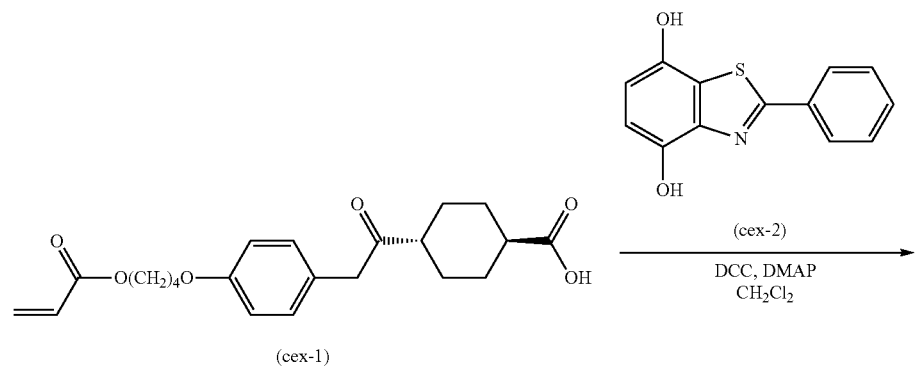

-continued

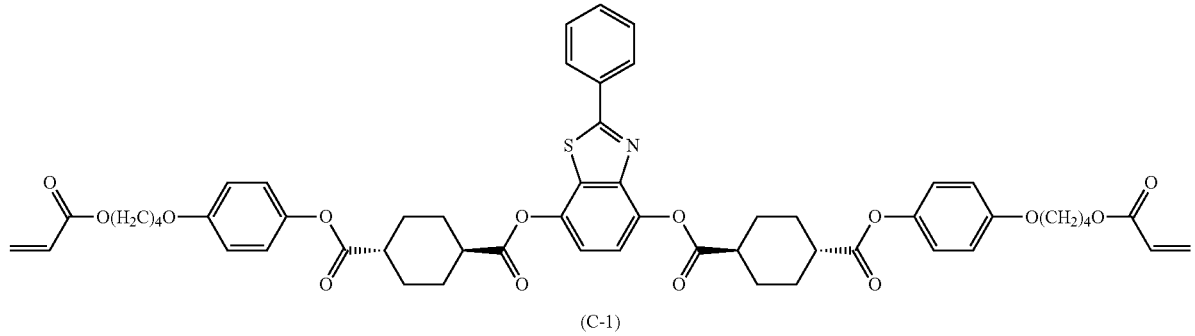

(C-1)

Compound (cex-1) was prepared by a method similar to the method in Example 1 in JP 2015-157776 A.

Compound (cex-2) was prepared by a method similar to the method in Example 1 in JP 2016-128403 A.

To 50 mL of dichloromethane, 5.0 g of compound (cex-1), 1.5 g of compound (cex-2) and 0.3 g of DMAP were added, and the resulting mixture was stirred while being cooled at 5° C. under a nitrogen atmosphere in an ice bath. Then, 5 mL of a dichloromethane solution in which 2.5 g of DCC was dissolved was added dropwise. After dropwise addition, the resulting mixture was stirred at room temperature for 16 hours. The precipitated deposits were filtered off, an organic layer was washed with water, and dried over anhydrous magnesium sulfate. Dichloromethane was distilled off under reduced pressure, and the resulting residue was purified by column chromatography, and recrystallized in methanol to obtain 3.8 g of compound (C-1), in which a column of column chromatography was a silica gel, in which an eluent of the column chromatography was a mixture of toluene and ethyl acetate at 4:1 in a volume ratio.

When compound (C-1) was heated, transition was caused from the crystal phase to the smectic phase at 104° C., and then transition was caused from the smectic phase to the nematic phase at 125° C. Polymerization was performed at around 220° C., and therefore no transition to the isotropic liquid was found.

Signals of proton NMR of compound (C-1) were as described below.

8.09 to 8.03 (m, 2H), 7.55 to 7.46 (m, 3H), 7.21 (s, 2H), 7.00 (d, 4H), 6.89 (d, 4H), 6.41 (d, 2H), 6.18-6.09 (m, 2H), 5.83 (d, 2H), 4.24 (t, 4H), 3.99 (t, 4H), 2.86-2.78 (m, 1H), 2.75-2.59 (m, 3H), 2.49-2.30 (m, 8H), 1.92-1.65 (m, 16H).

Compound (C-2) was prepared according to procedures described below.

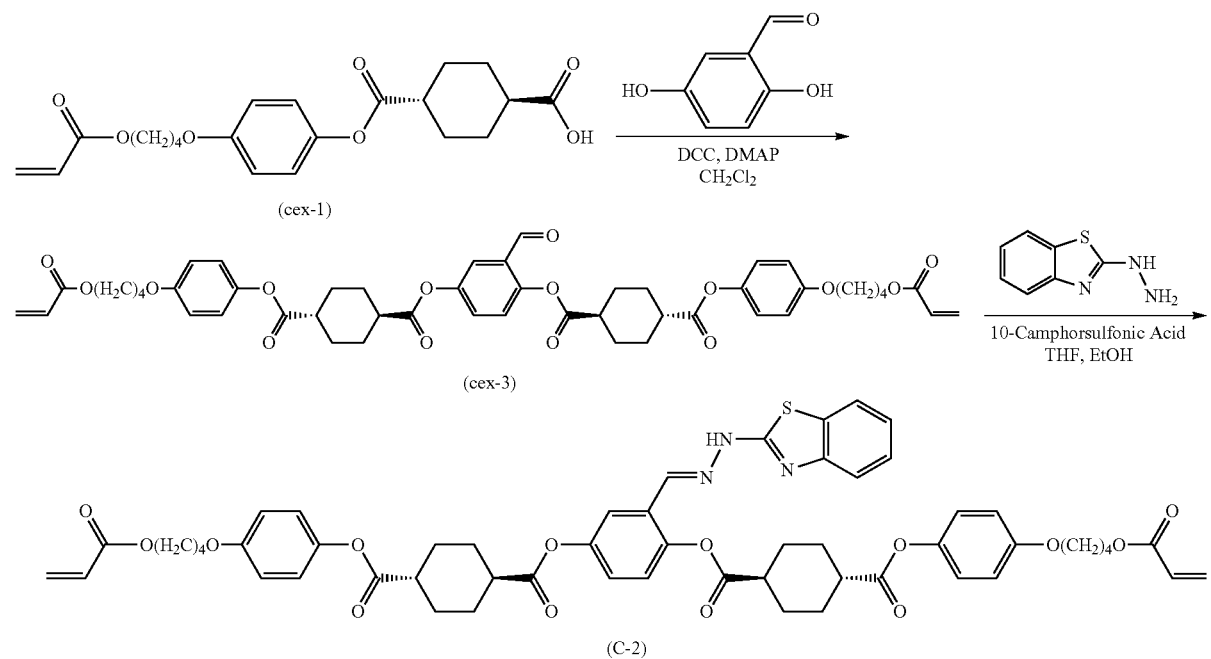

(C-2)

To 100 mL of dichloromethane, 10.0 g of compound (cex-1), 1.7 g of 2,5-dihydroxybenzaldehyde and 0.6 g of DMAP were added, and the resulting mixture was stirred while being cooled at 5° C. under a nitrogen atmosphere in an ice bath. Then, 10 mL of a dichloromethane solution in which 5.1 g of DCC was dissolved was added dropwise. After dropwise addition, the resulting mixture was stirred at room temperature for 16 hours.

The precipitated deposits were filtered off, an organic layer was washed with water, and dried over anhydrous magnesium sulfate. Dichloromethane was distilled off under reduced pressure, and the resulting residue was purified by column chromatography, and recrystallized in methanol to obtain 8.1 g of compound (cex-3), in which a column of column chromatography was a silica gel, and an eluent of the column chromatography was a mixture of toluene and ethyl acetate at 4:1 in a volume ratio.

To a mixed solvent of 100 mL of THF and 20 mL of ethanol, 5.0 g of compound (cex-3) and 0.2 g of (±)-10-camphorsulfonic acid were added, and the resulting mixture was stirred while being cooled at 5° C. under a nitrogen atmosphere in an ice bath. Then, 20 mL of a THF solution in which 1.1 g of 2-hydrazinobenzothiazole was dissolved was added dropwise thereto. Ethyl acetate and water were added thereto, and an organic layer was extracted, and dried over anhydrous magnesium sulfate.

A solvent was distilled off under reduced pressure, and the resulting residue was purified by column chromatography, and recrystallized in methanol to obtain 2.2 g of compound (C-2), in which an eluent of the column chromatography was a mixture of toluene and ethyl acetate at 5:1 in a volume ratio.

When compound (C-2) was heated, transition was caused from a crystal phase to a nematic phase at 174° C. When compound (C-2) was further heated, it was polymerized in the vicinity of 220° C., and therefore the transition to the isotropic liquid was not found.

Signals of proton NMR of compound (C-2) were as described below.

12.63 (s, 1H), 8.10 (s, 1H), 7.80 (d, 1H), 7.61 (d, 1H), 7.48 (s, 1H), 7, 35-7.21 (m, 3H), 7.14 (t, 1H), 6.99 (d, 4H), 6.88 (d, 4H), 6.41 (d, 2H), 6.16-6.09 (m, 4H), 5.83 (d, 2H), 4.18 (t, 4H), 3.95 (t, 4H), 2.53-2.67 (m, 2H), 2.64-2.57 (m, 2H), 2.38-2.28 (m, 8H), 1.84-1.65 (m, 16H).

Compound (M1-13-1) was prepared according to procedures described below.

stirred while being cooled at 5° C. under a nitrogen atmosphere in an ice bath. Then, 40 mL of a dichloromethane solution in which 20.3 g of DCC was dissolved was added dropwise. After dropwise addition, the resulting mixture was stirred at room temperature for 16 hours.

The precipitated deposits were filtered off, an organic layer was washed with water, and dried over anhydrous magnesium sulfate. Dichloromethane was distilled off under reduced pressure, and the resulting residue was purified by column chromatography, and recrystallized in methanol to obtain 36.8 g of compound (M1-13-1), in which a column of column chromatography was a silica gel, and an eluent of the column chromatography was a mixture of toluene and ethyl acetate at 40:1 in a volume ratio.

Compound (M1-13-1) caused transition from a crystal phase to a smectic phase at 39° C., during temperature rise, from the smectic phase to a nematic phase at 76° C., and from the nematic phase to an isotropic liquid at 86° C.

Signals of proton NMR of compound (M1-13-1) were as described below.

7.20-7.14 (m, 4H), 6.92 (d, 2H), 6.84 (d, 2H), 6.41 (d, 1H), 6.18-6.09 (m, 1H), 5.83 (d, 1H), 4.17 (t, 2H), 3.95 (t, 2H), 3.01 (t, 2H), 2.83 (t, 2H), 2.48-2.40 (m, 1H), 1.90-1.68 (m, 8H), 1.56-1.18 (m, 15H), 1.08-0.98 (m, 2H), 0.89 (t, 3H).

Compound (M2-3-1) was prepared by a method similar to the method in Example 6 in JP 4063873 B.

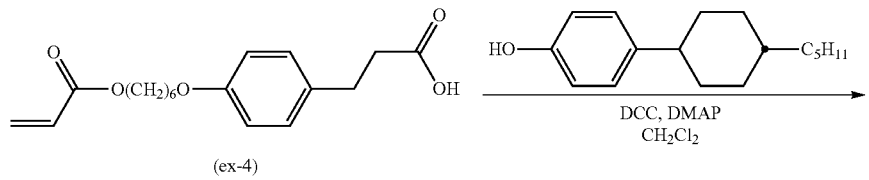

(ex-4)

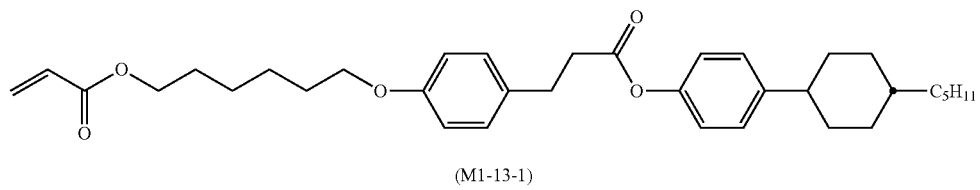

(M1-13-1)

To 300 mL of dichloromethane, 30.0 g of compound (ex-4), 23.1 g of trans-4-(4-pentylcyclohexyl)phenol and 2.3 g of DMAP were added, and the resulting mixture was Compound (M2-1-1) was prepared by a method similar to the method described in Makromolekulare Chemie (1991), 192 (1), pp. 59-74.

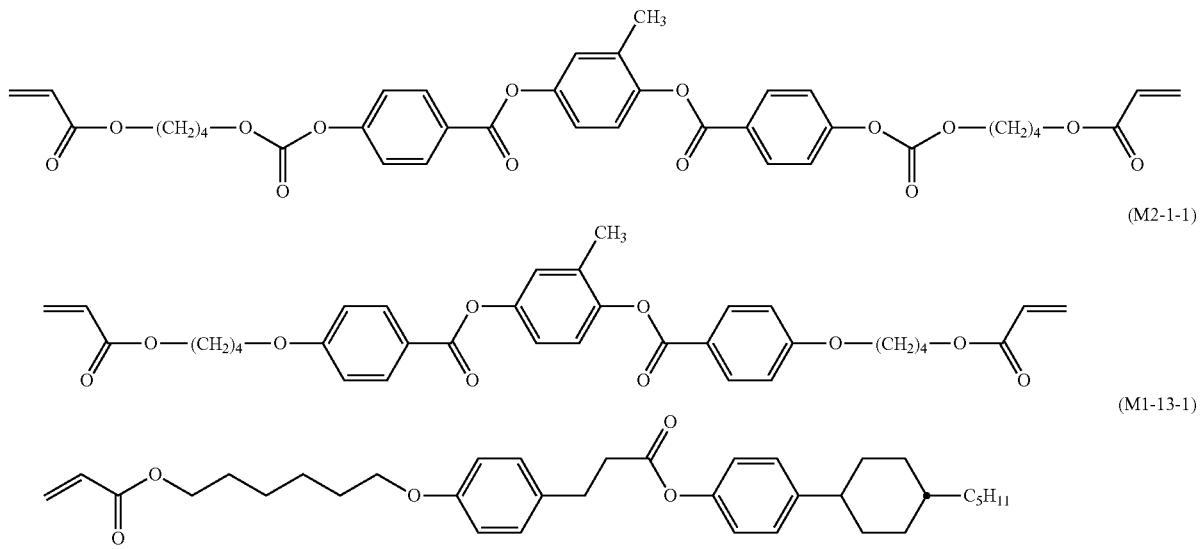

Example 10

Polymerizable liquid crystal compositions (S-1) to (S-11) each were prepared by mixing a compound, a polymerization initiator, a surfactant and cyclohexanone to satisfy a content shown in Table 1, in which "0" in Table 1 means that no material corresponding thereto was contained.

TABLE 1

| Name of Polymerizable liquid crystal composition | Content and name of Compound (1) | Content of Compound (M2-3-1) | Content of Compound (M2-1-1) | Content of Compound (M1-13-1) | Content and name of Polymerization initiator | Content and name of Surfactant | Content of Cyclohexanone |
|---|---|---|---|---|---|---|---|
| Polymerizable liquid crystal composition (S-1) | 12.5% by weight of Compound (1-1-1-1) | 12.5% by weight | 0 | 0 | 1.25% by weight of Irg-907 | 0.05% by weight of FTX-218 | 73.70% by weight |
| Polymerizable liquid crystal composition (S-2) | 28% by weight of Compound (1-1-1-1) | 0 | 0 | 0 | 1.4% by weight of NCI-930 | 0.06% by weight of FTX-218 | 70.54% by weight |
| Polymerizable liquid crystal composition (S-3) | 22.4% by weight of Compound (1-1-2-1) | 0 | 5.6% by weight | 0 | 1.7% by weight of Irg-907 | 0.14% by weight of TF370 | 70.16% by weight |
| Polymerizable liquid crystal composition (S-4) | 30% by weight of Compound (1-1-2-1) | 0 | 0 | 0 | 1.8% by weight of NCI-930 | 0.12% by weight of TF370 | 68.08% by weight |
| Polymerizable liquid crystal composition (S-5) | 8% by weight of Compound (1-5-1-1) | 6.0% by weight | 0 | 10% by weight | 1.4% by weight of NCI-930 | 0.07% by weight of TF370 | 74.53% by weight |
| Polymerizable liquid crystal composition (S-6) | 28% by weight of Compound (1-2-1-1) | 0 | 0 | 0 | 1.4% by weight of NCI-930 | 0.11% by weight of TF370 | 70.49% by weight |
| Polymerizable liquid crystal composition (S-7) | 28% by weight of Compound (1-2-4-1) | 0 | 0 | 0 | 1.4% by weight of NCI-930 | 0.06% by weight of FTX-218 | 70.54% by weight |
| Polymerizable liquid crystal composition (S-8) | 28% by weight of Compound (1-2-5-1) | 0 | 0 | 0 | 1.4% by weight of NCI-930 | 0.06% by weight of FTX-218 | 70.54% by weight |

TABLE 1-continued

| Name of Polymerizable liquid crystal composition | Content and name of Compound (1) | Content of Compound (M2-3-1) | Content of Compound (M2-1-1) | Content of Compound (M1-13-1) | Content and name of Polymerization initiator | Content and name of Surfactant | Content of Cyclohexanone |
|---|---|---|---|---|---|---|---|
| Polymerizable liquid crystal composition (S-9) | 10.4% by weight of Compound (1-1-10-1) | 0 | 10.4% by weight | 5.2% by weight | 1.6% by weight of NCI-930 | 0.13% by weight of PF No. 75 | 72.27% by weight |
| Polymerizable liquid crystal composition (S-10) | 28% by weight of Compound (1-1-12-1) | 0 | 0 | 0 | 1.7% by weight of NCI-930 | 0.14% by weight of PF No. 75 | 70.16% by weight |
| Polymerizable liquid crystal composition (S-11) | 12% by weight of Compound (1-1-10-1) | 6% by weight | 6% by weight | 0 | 1.2% by weight of NCI-930 | 0.07% by weight of TF370 | 74.73% by weight |

Polymerizable liquid crystal compositions (SC-1) to (SC-4) each were prepared by mixing a compound, a polymerization initiator, a surfactant and cyclohexane shown in Table 2 to satisfy a content shown in Table 2, in which "0" in Table 2 means that a material corresponding thereto was contained. Polymerizable liquid crystal compositions (SC-1) to (SC-4) are compositions in Comparative Examples.

TABLE 2

| Name of Polymerizable liquid crystal composition | Content of Compound (C-1) | Content of Compound (C-2) | Content of Compound (M2-3-1) | Content and name of Polymerization initiator | Content and name of Surfactant | Content of Cyclohexanone |
|---|---|---|---|---|---|---|
| Polymerizable liquid crystal composition (S-1) | 0 | 0 | 22% by weight | 1.1% by weight of Irg-907 | 0.04% by weight of FTX-218 | 76.86% by weight |
| Polymerizable liquid crystal composition (S-2) | 12% by weight | 0 | 12% by weight | 1.4% by weight of Irg-907 | 0.05% by weight of FTX-218 | 74.55% by weight |
| Polymerizable liquid crystal composition (S-3) | 28% by weight | 0 | 0 | 1.4% by weight of Irg-907 | 0.06% by weight of FTX-218 | 70.54% by weight |
| Polymerizable liquid crystal composition (S-4) | 0 | 28% by weight | 0 | 1.4% by weight of Irg-907 | 0.06% by weight of FTX-218 | 70.54% by weight |

Preparation of Substrate-Embedded Liquid Crystal Polymerization Film

Example 11

Liquid crystal polymerization film (F-1) with a substrate was prepared according to procedures described below.

Procedure (1): liquid crystal composition (S-1) was coated, by spin coating, onto a glass substrate with an alignment film subjected to rubbing treatment;

Procedure (2): the substrate was heated at 80 to 100° C. for 2 minutes by using a hot plate, and a solvent in the liquid crystal composition was removed;

Procedure (3): subsequently, a temperature of the hot plate was decreased, and the temperature was maintained at a constant level for 2 minutes at a temperature at which the liquid crystal composition of the substrate exhibited a liquid crystal phase.

Procedure (4): subsequently, the substrate was cooled to room temperature for 1 minute; and Procedure (5): the liquid crystal composition on the substrate was subjected to polymerization by irradiating with ultraviolet light in air.

Liquid crystal polymerization film (F-1) with the substrate was alignment defect-free.

Example 12

According to procedures described in Example 11, liquid crystal polymerization film-kind (F-2) to (F-11) with substrates were obtained by using polymerizable liquid crystal compositions (S-2) to (S-11) in place of polymerizable liquid crystal composition (S-1), respectively.

Liquid crystal polymerization film-kind (F-2) to (F-11) with substrates were alignment defect-free.

Comparative Example 2

According to procedures described in Example 11, liquid crystal polymerization film (CF-1) with a substrate and liquid crystal polymerization film (CF-2) with a substrate were obtained by using polymerizable liquid crystal compositions (SC-1) and (SC-2) in place of polymerizable liquid crystal composition (S-1), respectively.

Liquid crystal polymerization film-kind (CF-1) to (CF-2) with substrates were alignment defect-free.

Comparative Example 3

When an attempt was made on obtaining a substrate-embedded liquid crystal polymerization film by using polymerizable liquid crystal composition (SC-3) in place of polymerizable liquid crystal composition (S-1) according to procedures described in Example 11, crystals precipitated in a step of procedure (4). Accordingly, an alignment defect-free substrate-embedded liquid crystal polymerization film was difficult to obtain from polymerizable liquid crystal composition (SC-3).

Therefore, an alignment defect-free substrate-embedded liquid crystal polymerization film is obviously easier to be prepared from the liquid crystal polymerization film with the substrate prepared using the polymerizable liquid crystal composition containing compound (1) as the raw material, in comparison with the liquid crystal polymerization film with the substrate prepared using the polymerizable liquid crystal composition containing compound (C-1) as the raw material.

Comparative Example 4

When an attempt was made on obtaining a substrate-embedded liquid crystal polymerization film by using polymerizable liquid crystal composition (SC-4) in place of polymerizable liquid crystal composition (S-1) according to procedures described in Example 11, crystals precipitated in a step of procedure (3). Accordingly, an alignment defect-free substrate-embedded liquid crystal polymerization film was difficult to obtain from polymerizable liquid crystal composition (SC-4). The results show that, from compound (1), the alignment defect-free substrate-embedded liquid crystal polymerization film can be obtained, even with a higher amount of content, in comparison with compound (C-2).

Optical Characteristics of Optically Anisotropic Film

Table 3 shows results of chromatic dispersion characteristics of the liquid crystal polymerization film-kind with the substrate prepared as described above.

TABLE 3

| Name of liquid crystal polymer film with substrate | Name of Polymerizable liquid crystal composition | $Re_{550}$/ nm | Film thickness/ μm | Δn (550) | $Re_{450}/Re_{550}$ | $Re_{650}/Re_{550}$ |
|---|---|---|---|---|---|---|
| Liquid crystal polymer film with substrate (F-1) | Polymerizable liquid crystal composition (S-1) | 129.1 | 1.26 | 0.10 | 1.039 | 0.974 |
| Liquid crystal polymer film with substrate (F-2) | Polymerizable liquid crystal composition (S-2) | 139.2 | 1.72 | 0.08 | 0.990 | 1.001 |
| Liquid crystal polymer film with substrate (F-3) | Polymerizable liquid crystal composition (S-3) | 145.6 | 1.39 | 0.10 | 1.028 | 0.981 |
| Liquid crystal polymer film with substrate (F-4) | Polymerizable liquid crystal composition (S-4) | 132.5 | 1.78 | 0.07 | 0.992 | 0.998 |
| Liquid crystal polymer film with substrate (F-5) | Polymerizable liquid crystal composition (S-5) | 136.6 | 1.08 | 0.11 | 1.021 | 0.988 |
| Liquid crystal polymer film with substrate (F-6) | Polymerizable liquid crystal composition (S-6) | 145.1 | 1.67 | 0.09 | 1.016 | 0.986 |
| Liquid crystal polymer film with substrate (F-7) | Polymerizable liquid crystal composition (S-7) | 143.6 | 1.50 | 0.10 | 1.001 | 0.993 |
| Liquid crystal polymer film with substrate (F-8) | Polymerizable liquid crystal composition (S-8) | 136.1 | 1.45 | 0.09 | 1.015 | 0.989 |
| Liquid crystal polymer film with substrate (F-9) | Polymerizable liquid crystal composition (S-9) | 150.1 | 1.25 | 0.12 | 0.947 | 1.002 |
| Liquid crystal polymer film with substrate (F-10) | Polymerizable liquid crystal composition (S-10) | 146.8 | 1.63 | 0.09 | 1.015 | 0.981 |
| Liquid crystal polymer film with substrate (F-11) | Polymerizable liquid crystal composition (S-11) | 139.3 | 1.27 | 0.11 | 0.993 | 0.990 |

TABLE 3-continued

| Name of liquid crystal polymer film with substrate | Name of Polymerizable liquid crystal composition | $Re_{550}/$ nm | Film thickness/ μm | Δn (550) | $Re_{450}/Re_{550}$ | $Re_{650}/Re_{550}$ |
|---|---|---|---|---|---|---|
| Liquid crystal polymer film with substrate (CF-1) | Polymerizable liquid crystal composition (SC-1) | 142.9 | 0.97 | 0.15 | 1.098 | 0.955 |
| Liquid crystal polymer film with substrate (CF-2) | Polymerizable liquid crystal composition (SC-2) | 150.4 | 1.35 | 0.11 | 1.057 | 0.972 |

From Table 3, $Re_{450}/Re_{550}$ of liquid crystal polymerization film-kind (F-1) to (F-11) with the substrates each was found to be significantly smaller than $Re_{450}/Re_{550}$ of liquid crystal polymerization film-kind (CF-1) and (CF-2) each. On the other hand, $Re_{650}/Re_{550}$ of liquid crystal polymerization film-kind (F-1) to (F-11) with the substrates each was found to be significantly larger than $Re_{650}/Re_{550}$ of liquid crystal polymerization film-kind (CF-1) and (CF-2) each.

Thus, the liquid crystal polymerization film-kind in which a degree of increase of retardation in association with an increase of the wavelength in the visible light region is low was found to be able to be produced from the polymerizable liquid crystal compounds of the invention.

Solubility of Compound in Solvent

With regard to various solvents, a specific amount of compound (1-1-1-1) was added to various solvents each, and the resulting mixture was warmed in warm water at 40° C., and an aspect after 30 minutes was visually confirmed. A similar method was tried in compound (1-1-2-1), compound (C-1) and compound (C-2) in place of compound (1-1-1-1). Table 4 shows the results described above. An amount of the compound added as described in Table 4 is expressed in terms of a relative value when a total weight of the solvent and the compound is taken as 100% by weight. A term "Good" in Table 4 represents that the compound was completely dissolved, and a term "Poor" in Table 4 represents that an insoluble matter remained.

From data shown in Table 4, compound (1-1-1-1) or compound (1-1-2-1) was found to have a larger number of kinds of organic solvents in which the compound can be dissolved in comparison with compound (C-1) or compound (C-2). From data shown in Table 4, a larger amount of compound (1-1-1-1) or compound (1-1-2-1) was found to be dissolvable in the organic solvent in comparison with compound (C-1) or compound (C-2).

From the results described above, the number of printing methods that can be applied, for example, the number of options of printing machines that can be used obviously increases to contribute to an improvement of productivity of the liquid crystal polymerization film-kind. If compound (1-1-1-1) or compound (1-1-2-1) is used, formation with a thick film can be obviously made to facilitate to obtain a desired phase difference.

Stability of Liquid Crystal Phase

After procedure (4) of the method described in Example 11, the resulting material was left to stand at room temperature, and existence or non-existence of precipitation of crystals from the polymerizable composition was confirmed. Table 5 shows the results.

TABLE 4

| Name and content of Compound | Compound (1-1-1-1) | Compound (1-1-2-1) | Compound (C-1) | Compound (C-2) |
|---|---|---|---|---|
| When 15% by weight of compound was added to cyclohexanone | Good | Good | Good | Good |
| When 30% by weight of compound was added to cyclohexanone | Good | Good | Poor | Poor |
| When 15% by weight of compound was mixed with methoxybenzene | Good | Good | Good | Good |
| When 30% by weight of compound was mixed with methoxybenzene | Good | Good | Poor | Poor |
| When 15% by weight of compound was mixed with 2-acetoxy-1-methoxypropane | Poor | Good | Poor | Poor |
| When 30% by weight of compound was mixed with 2-acetoxy-1-methoxypropane | Poor | Poor | Poor | Poor |
| When 15% by weight of compound was mixed with 4-methyl-2-pentanone | Poor | Good | Poor | Poor |
| When 30% by weight of compound was mixed with 4-methyl-2-pentanone | Poor | Poor | Poor | Poor |

TABLE 5

| Name of Polymerizable liquid crystal composition | Results |
|---|---|
| Polymerizable liquid crystal composition (S-2) | Even after 30 minutes from the time in and after procedure (4), no precipitation was observed. |
| Polymerizable liquid crystal composition (S-4) | Even after 1 hour from the time in and after procedure (4), no precipitation was observed. |
| Polymerizable liquid crystal composition (S-6) | Even after 30 minutes from the time in and after procedure (4), no precipitation was observed. |
| Polymerizable liquid crystal composition (SC-3) | After 15 seconds from the time in and after procedure (4), precipitation was observed. |
| Polymerizable liquid crystal composition (SC-4) | At the end point of procedure (4), precipitation was already observed. |

From Table 5, the liquid crystal phase was obviously maintained for a long period of time even after procedure (4) upon preparing the liquid crystal polymerization film by using polymerizable liquid crystal composition (S-2), (S-4) or (S-6) as the raw material. In contrast, from Table 5, maintenance of the liquid crystal phase was obviously difficult after procedure (4) when polymerizable liquid crystal composition (SC-3) or (SC-4) was used as the raw material.

Thus, the compound of the invention is easy in handling of the liquid crystal polymerization film in the production process and other stages.

What is claimed is:

1. A polymerizable liquid crystal compound, represented by formula (1):

(1)

wherein, in formula (1), $A^1$ is independently 1,4-phenylene, 1,4-cyclohexylene, 1-cyclohexene-1,4-ylene, 2-cyclohexene-1,4-ylene, pyridine-2,5-diyl or naphthalene-2,6-diyl, and in the 1,4-phenylene or the naphthalene-2,6-diyl, at least one hydrogen may be replaced by fluorine, chlorine, trifluoromethyl, alkyl having 1 to 5 carbons, alkoxy having 1 to 5 carbons, alkoxycarbonyl having 1 to 5 carbons or alkanoyl having 1 to 5 carbons, $Z^1$ is independently a single bond, —OCH$_2$—, —CH$_2$O—, —COO—, —OCO—, —CF$_2$O—, —OCF$_2$—, —CH$_2$CH$_2$—, —CF$_2$CF$_2$—, —OCH$_2$CH$_2$O—, —CH=CHCOO—, —OCOCH=CH—, —CH$_2$CH$_2$COO—, —OCOCH$_2$CH$_2$—, —CH$_2$CH$_2$OCO—, —COOCH$_2$CH$_2$—, —CH=CH—, —N=CH—, —CH=N—, —N=C(CH$_3$)—, —C(CH$_3$)=N—, —N=N— or —C≡C—, m is each independently an integer from 0 to 3, in which at least one m is not 0, G is a divalent organic group that comprises a quinoline skeleton, an isoquinoline skeleton, benzoquinoline skeleton, a quinoxaline skeleton, a benzoquinoxaline skeleton or a quinazoline skeleton, wherein G has 10 to 24 π-electrons, and $R^1$ is independently hydrogen, fluorine, chlorine, trifluoromethyl, trifluoromethoxy, cyano, alkyl having 1 to 12 carbons, alkoxy having 1 to 12 carbons, alkenyl having 2 to 12 carbons, alkylester having 1 to 12 carbons or a group represented by formula (2), in which at least one $R^1$ is a group represented by formula (2);

—Y-Q$^1$-PG    (2)

wherein, in formula (2), $Y^1$ is a single bond, —O—, —COO—, —OCO— or —OCOO—, $Q^1$ is a single bond or alkylene having 1 to 20 carbons, and in the alkylene, at least one —CH$_2$— may be replaced by —O—, —COO—, —OCO—, —CH=CH— or C≡C—, and PG is a polymerizable group represented by any one of formula (PG-1) to formula (PG-9):

(PG-1)

(PG-2)

(PG-3)

(PG-4)

(PG-5)

(PG-6)

(PG-7)

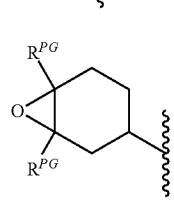

-continued

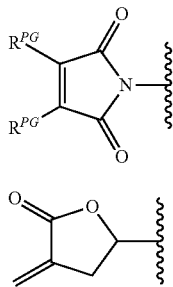
(PG-8)

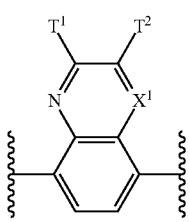
(PG-9)

wherein, in formula (PG-1) to formula (PG-9), $R^{PG}$ is independently hydrogen, halogen, methyl, ethyl or trifluoromethyl.

2. The polymerizable liquid crystal compound according to claim 1, wherein,

G is (A) a divalent functional group that has a quinoline skeleton, and is connected in 5-position and 8-position of the quinoline skeleton, respectively, (B) a divalent functional group that has an isoquinoline skeleton, and is connected in 5-position and 8-position of the isoquinoline skeleton, respectively, (C) a divalent functional group that has a quinoxaline skeleton, and is connected in 5-position and 8-position of the quinoxaline skeleton, respectively, or (D) a divalent functional group that has a quinazoline skeleton, and is connected in 5-position and 8-position of the quinazoline skeleton, respectively.

3. The polymerizable liquid crystal compound according to claim 1, wherein, $A^1$ is independently 1,4-phenylene, 1,4-cyclohexylene, 1-cyclohexene-1,4-ylene or 2-cyclohexene-1,4-ylene, and in the 1,4-phenylene, at least one hydrogen may be replaced by fluorine, chlorine, trifluoromethyl, alkyl having 1 to 5 carbons, alkoxy having 1 to 5 carbons, alkoxycarbonyl having 1 to 5 carbons or alkanoyl having 1 to 5 carbons, and $Z^1$ is independently a single bond, —OCH$_2$—, —CH$_2$O—, —COO—, —OCO—, —CF$_2$O—, —OCF$_2$—, —CH$_2$CH$_2$—, —OCH$_2$CH$_2$O—, —CH$_2$CH$_2$COO—, —OCOCH$_2$CH$_2$—, —CH$_2$CH$_2$OCO— or —COOCH$_2$CH$_2$—.

4. The polymerizable liquid crystal compound according to claim 1, wherein, both $R^1$ are a group represented by formula (2).

5. The polymerizable liquid crystal compound according to claim 1, wherein G is a group described in formula (G-1), formula (G-2) or formula (G-3):

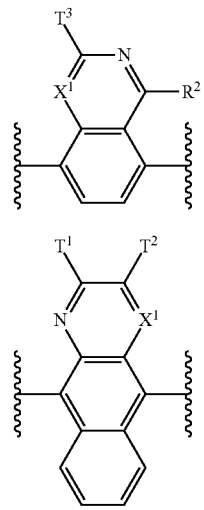
(G-1)
(G-2)
(G-3)

wherein, in formula (G-1), formula (G-2) and formula (G-3), $X^1$ is =C($R^3$)— or —N=, in which $R^3$ is independently hydrogen, fluorine, chlorine, trifluoromethyl, trifluoromethoxy, alkyl having 1 to 12 carbons or phenyl, and $T^1$, $T^2$ and $T^3$ are independently hydrogen, fluorine, chlorine, trifluoromethyl, trifluoromethoxy, alkyl having 1 to 12 carbons, alkoxy having 1 to 12 carbons, alkoxycarbonyl having 1 to 12 carbons, alkanoyl having 1 to 12 carbons or an aromatic ring having 6 to 18 i-electrons, and in the alkyl, the alkoxy, the alkoxycarbonyl and the alkanoyl, at least one or more —CH$_2$— may be replaced by —O—, —CO— or —S—, and $T^1$ and $T^2$ may be bonded to each other to form a ring, and $R^2$ is independently hydrogen, fluorine, chlorine, trifluoromethyl, trifluoromethoxy, alkyl having 1 to 12 carbons or phenyl.

6. The polymerizable liquid crystal compound according to claim 5, wherein, in formula (G-1) or formula (G-2), at least either $T^1$ or $T^2$, and $T^3$ are an aromatic ring described in any one of formula (T-1) to formula (T-9):

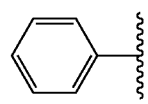
(T-1)

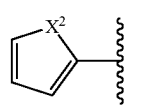
(T-2)

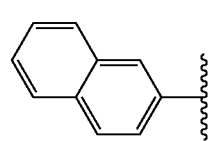
(T-3)

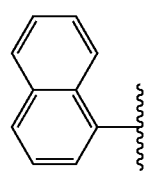
(T-4)

-continued

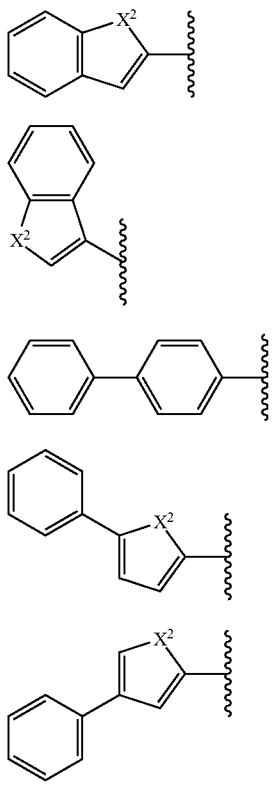

(T-5)

(T-6)

(T-7)

(T-8)

(T-9)

wherein, in formula (T-1) to formula (T-9), $X^2$ is —O—, —S— or in which $R^4$ is hydrogen, alkyl having 1 to 5 carbons, alkanoyl having 1 to 5 carbons or phenyl, wherein in aryl groups of T1-T9, at least one or more —CH= may be replaced by —N=, and at least one hydrogen may be replaced by fluorine, chlorine, cyano, trifluoromethyl, trifluoroacetyl, alkyl having 1 to 5 carbons, alkoxy having 1 to 5 carbons, alkylester having 1 to 5 carbons or alkanoyl having 1 to 5 carbons.

7. The polymerizable liquid crystal compound according to claim 5 or 6, wherein, in formula (G-1), $T^1$ and $T^2$ are bonded to each other to form a ring, and a structure of the ring is a condensed ring formed of a 5-membered ring, a six-membered ring or a combination of 5-membered ring and six-membered ring.

8. The polymerizable liquid crystal compound according to claim 1, wherein PG is a polymerizable group represented by formula (PG-1), and $R^{PG}$ is hydrogen or methyl.

9. The polymerizable liquid crystal compound according to claim 1, wherein at least one $A^1$ is 1,4-cyclohexylene.

10. The polymerizable liquid crystal compound according to claim 1, wherein at least one $Z^1$ is —CH$_2$CH$_2$COO— or —OCOCH$_2$CH$_2$—, and both m's are 2.

11. A polymerizable liquid crystal composition, comprising at least one polymerizable liquid crystal compound according to claim 1.

12. The polymerizable liquid crystal composition according to claim 11, wherein a total of content of the polymerizable liquid crystal compound according to claim 1 is 4 to 50% by weight.

* * * * *